(12) United States Patent
Zhou

(10) Patent No.: US 12,090,330 B2
(45) Date of Patent: Sep. 17, 2024

(54) BUNDLE BRANCH PACING DEVICES AND METHODS

(71) Applicant: Medtronic, Inc., Minneapolis, MN (US)

(72) Inventor: Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 816 days.

(21) Appl. No.: 16/162,945

(22) Filed: Oct. 17, 2018

(65) Prior Publication Data

US 2019/0111264 A1 Apr. 18, 2019

Related U.S. Application Data

(60) Provisional application No. 62/617,059, filed on Jan. 12, 2018, provisional application No. 62/581,486, (Continued)

(51) Int. Cl.
*A61N 1/368* (2006.01)
*A61B 5/00* (2006.01)
(Continued)

(52) U.S. Cl.
CPC ............ *A61N 1/3686* (2013.01); *A61B 5/283* (2021.01); *A61B 5/349* (2021.01); *A61B 5/366* (2021.01);
(Continued)

(58) Field of Classification Search
None
See application file for complete search history.

(56) References Cited

U.S. PATENT DOCUMENTS 4,374,382 A 2/1983 Markowitz
4,624,265 A * 11/1986 Grassi .................. A61N 1/056
607/123

(Continued)

FOREIGN PATENT DOCUMENTS

EP 1234597 A2 8/2002
WO WO 2006/069215 A2 6/2006
(Continued)

OTHER PUBLICATIONS

U.S. Appl. No. 61/819,946, filed May 6, 2013.
(Continued)

*Primary Examiner* — Michael W Kahelin
(74) *Attorney, Agent, or Firm* — Mueting Raasch Group

(57) ABSTRACT

The present disclosure relates generally to pacing of cardiac tissue, and more particularly to adjusting delivery of His bundle or bundle branch pacing in a cardiac pacing system to achieve synchronized ventricular activation. A left bundle branch (LBB) cathode electrode may be implanted a left side of the septum of the patient's heart proximate to the LBB, and a right bundle branch (RBB) cathode electrode may be implanted on a right side of the septum of the patient's heart proximate to the RBB. One or both cathode electrodes may be used to deliver synchronized left and right bundle-branch pacing based on one or both of an atrial event and a ventricular event. A device for bundle branch pacing may be implanted based on determining whether an LBB block pattern or an RBB block pattern is present in monitored electrical activity.

22 Claims, 30 Drawing Sheets

Related U.S. Application Data filed on Nov. 3, 2017, provisional application No. 62/573,685, filed on Oct. 17, 2017.

(51) Int. Cl.

| | | |
|---|---|---|
| *A61B 5/24* | (2021.01) | |
| *A61B 5/283* | (2021.01) | |
| *A61B 5/349* | (2021.01) | |
| *A61B 5/363* | (2021.01) | |
| *A61B 5/366* | (2021.01) | |
| *A61N 1/05* | (2006.01) | |
| *A61N 1/362* | (2006.01) | |
| *A61N 1/365* | (2006.01) | |
| *A61N 1/37* | (2006.01) | |
| *A61N 1/372* | (2006.01) | |
| *A61N 1/375* | (2006.01) | |
| *A61N 1/39* | (2006.01) | |

(52) U.S. Cl.
CPC .......... *A61B 5/7235* (2013.01); *A61B 5/7282* (2013.01); *A61N 1/36507* (2013.01); *A61N 1/36585* (2013.01); *A61N 1/3682* (2013.01); *A61N 1/3684* (2013.01); *A61N 1/3704* (2013.01); *A61N 1/3956* (2013.01); *A61B 5/24* (2021.01); *A61B 5/363* (2021.01); *A61B 5/686* (2013.01); *A61B 5/6869* (2013.01); *A61N 1/056* (2013.01); *A61N 1/3627* (2013.01); *A61N 1/3688* (2013.01); *A61N 1/37211* (2013.01); *A61N 1/37264* (2013.01); *A61N 1/37282* (2013.01); *A61N 1/37288* (2013.01); *A61N 1/3756* (2013.01)

(56) References Cited

U.S. PATENT DOCUMENTS

| | | |
|---|---|---|
| 5,117,824 A | 6/1992 | Keimel et al. |
| 5,174,286 A | 12/1992 | Chirife |
| 5,545,186 A | 8/1996 | Olson et al. |
| 5,728,140 A | 3/1998 | Salo et al. |
| 5,755,736 A | 5/1998 | Gillberg et al. |
| 5,800,467 A | 9/1998 | Park et al. |
| 6,453,192 B1 | 9/2002 | Ding et al. |
| 6,556,866 B2* | 4/2003 | Dal Molin ............ A61N 1/3627 607/9 |
| 6,609,027 B2 | 8/2003 | Kroll et al. |
| 6,711,443 B2 | 3/2004 | Osypka |
| 6,718,206 B2 | 4/2004 | Casvant |
| 6,738,674 B2 | 5/2004 | Osypka |
| 6,768,923 B2 | 7/2004 | Ding et al. |
| 6,804,555 B2* | 10/2004 | Warkentin ............ A61N 1/3684 607/9 |
| 6,988,007 B1 | 1/2006 | Morgan et al. |
| 7,177,704 B2 | 2/2007 | Laske et al. |
| 7,647,124 B2 | 1/2010 | Williams |
| 7,729,782 B2 | 6/2010 | William et al. |
| 7,738,954 B1 | 6/2010 | Kroll et al. |
| 7,792,580 B2 | 9/2010 | Borowitz et al. |
| 7,801,624 B1* | 9/2010 | Flannery ............ A61N 1/0573 607/116 |
| 7,815,577 B2 | 10/2010 | Krishnan |
| 8,013,133 B2 | 9/2011 | Sharma et al. |
| 8,078,287 B2 | 12/2011 | Liu et al. |
| 8,112,160 B2 | 2/2012 | Foster |
| 8,321,014 B2 | 11/2012 | Maskara et al. |
| 8,406,899 B2 | 3/2013 | Reddy et al. |
| 8,560,068 B2 | 10/2013 | Forslund et al. |
| 8,565,880 B2 | 10/2013 | Dong et al. |
| 8,588,907 B2 | 11/2013 | Arcot-krishnamurthy et al. |
| 8,606,369 B2 | 12/2013 | Williams et al. |
| 8,688,234 B2 | 4/2014 | Zhu et al. |
| 8,761,880 B2 | 6/2014 | Maskara et al. |
| 8,834,384 B2 | 9/2014 | Krishnan |
| 8,874,237 B2 | 10/2014 | Schilling |
| 8,942,805 B2 | 1/2015 | Shuros et al. |
| 8,954,147 B2 | 2/2015 | Arcot-krishnamurthy et al. |
| 9,162,066 B2 | 10/2015 | Hedberg et al. |
| 9,168,382 B2 | 10/2015 | Shuros et al. |
| 9,550,058 B2 | 1/2017 | Foster |
| 9,789,319 B2 | 10/2017 | Sambelashvili |
| 10,850,107 B2 | 12/2020 | Li et al. |
| 10,850,108 B2 | 12/2020 | Li et al. |
| 2003/0199938 A1 | 10/2003 | Smits et al. |
| 2003/0199956 A1 | 10/2003 | Struble et al. |
| 2004/0153127 A1 | 8/2004 | Gordon et al. |
| 2006/0206153 A1 | 9/2006 | Libbus et al. |
| 2007/0016261 A1 | 1/2007 | Dong et al. |
| 2007/0078490 A1 | 4/2007 | Cowan et al. |
| 2008/0072136 A1 | 4/2008 | Gaudiani |
| 2008/0177344 A1* | 7/2008 | Maskara ............ A61N 1/36842 607/25 |
| 2008/0288008 A1 | 11/2008 | Lee |
| 2010/0069983 A1 | 3/2010 | Peacock et al. |
| 2011/0319956 A1 | 12/2011 | Zhu et al. |
| 2012/0101539 A1 | 4/2012 | Zhu et al. |
| 2013/0079861 A1* | 3/2013 | Reinert ................ A61N 1/3756 607/126 |
| 2013/0090701 A1 | 4/2013 | Liu et al. |
| 2013/0158621 A1 | 6/2013 | Ding et al. |
| 2014/0107723 A1 | 4/2014 | Hou et al. |
| 2014/0107724 A1 | 4/2014 | Shuros et al. |
| 2014/0277239 A1 | 9/2014 | Maskara et al. |
| 2015/0045811 A1 | 2/2015 | Schilling |
| 2015/0217110 A1 | 8/2015 | Ollivier |
| 2016/0339248 A1 | 11/2016 | Schrock et al. |
| 2017/0304624 A1 | 10/2017 | Friedman et al. |
| 2017/0340887 A1 | 11/2017 | Engels et al. |
| 2018/0256904 A1 | 9/2018 | Li et al. |
| 2019/0022378 A1 | 1/2019 | Prillinger et al. |
| 2019/0111264 A1 | 4/2019 | Zhou |
| 2019/0111265 A1 | 4/2019 | Zhou |
| 2019/0111270 A1 | 4/2019 | Zhou |
| 2019/0126040 A1 | 5/2019 | Shuros et al. |
| 2019/0126049 A1 | 5/2019 | Casavant et al. |
| 2019/0126050 A1 | 5/2019 | Shuros et al. |
| 2019/0134404 A1 | 5/2019 | Sheldon et al. |
| 2019/0134405 A1 | 5/2019 | Sheldon et al. |
| 2019/0192092 A1 | 6/2019 | Hahn et al. |
| 2019/0192860 A1 | 6/2019 | Ghosh et al. |
| 2019/0201698 A1 | 7/2019 | Herrmann et al. |
| 2019/0217097 A1 | 7/2019 | Thakur et al. |
| 2019/0275329 A1 | 9/2019 | Brisben et al. |
| 2021/0085986 A1 | 3/2021 | Li et al. |

FOREIGN PATENT DOCUMENTS

| | | |
|---|---|---|
| WO | WO 2010/071849 A2 | 6/2010 |
| WO | WO 2014/055692 A2 | 4/2014 |
| WO | WO 2017/192892 A2 | 11/2017 |
| WO | 2020/010001 | 1/2020 |

OTHER PUBLICATIONS

International Search Report and Written Opinion for PCT/US2018/056242, mailed Feb. 11, 2019, 16 pages.

International Preliminary Report on Patentability for PCT/US2018/056242, mailed Apr. 30, 2020, 9 pages.

International Search Report and Written Opinion for PCT/US2018/056257, mailed Jan. 3, 2019, 16 pages.

International Preliminary Report on Patentability for PCT/US2018/056257, mailed Apr. 30, 2020, 9 pages.

International Search Report and Written Opinion for PCT/US2018/056292, mailed Jan. 30, 2019, 16 pages.

International Preliminary Report on Patentability for PCT/US2018/056292, mailed Apr. 30, 2020, 9 pages.

International Search Report and Written Opinion for PCT/US2018/056295, mailed Dec. 19, 2018, 18 pages.

International Preliminary Report on Patentability for PCT/US2018/056295, mailed Apr. 30, 2020, 9 pages.

(56) References Cited

OTHER PUBLICATIONS

International Search Report and Written Opinion for PCT Application No. PCT/US2020/016468 dated May 7, 2020, 10 pages.

International Search Report and Written Opinion for PCT Application No. PCT/US2020/016369 dated May 26, 2020, 10 pages.

Abdelrahman et al., "Clinical Outcomes of His Bundle Pacing Compared to Right Ventricular Pacing," *J Am Coll Cardiol.*, May 22, 2018; 71(20):2319-2330.

Ahmed et al., "Right Ventricular Apical Pacing-induced Left Ventricular Dyssynchrony is Associated with a Subsequent Decline in Ejection Fraction," *Heart Rhythm*, Apr. 2014; 11(4):602-608.

Ajijola et al., "Permanent His-bundle pacing for cardiac resynchronization therapy: Initial feasibility study in lieu of left ventricular lead," *Heart Rhythm*, Sep. 2017; 14(9):1353-1361.

Al-Hesayen et al., "Adverse effects of atrioventricular synchronous right ventricular pacing on left ventricular sympathetic activity, efficiency, and hemodynamic status," *Am J Physiol Heart Circ Physiol.*, 2006; 291(5):H2377-H2379.

Anderson et al., "Wilhelm His Junior and his bundle," *J Electrocardiol.*, 2016; 49:637-643.

Babu et al., "Three-dimensional echocardiography with left ventricular strain analyses helps earlier prediction of right ventricular pacing-induced cardiomyopathy," *J Saudi Heart Assoc.*, Apr. 2018;30(2):102-107.

Barba-Pichardo et al., "Permanent His-Bundle Pacing in patients with Infra-Hisian Atrioventricular Block," *Revista Espanola de Cardiologia*, Jun. 2006; 59(6):553-558.

Cantù et al., "Validation of Criteria for Selective His Bundle and Para-Hisian Permanent Pacing," *Pacing & Clinical Electrophysiology*, Dec. 2006; 29(12):1326-1333.

Catanzari et al., "Permanent His-Bundle Pacing Maintains Long-Term Ventricular Synchrony and Left Ventricular Performance, Unlike Conventional Right Ventricular Apical Pacing," *EP Europace*, Apr. 2013; 15(4):546-553.

Chang et al., "Tricuspid Valve Dysfunction Following Pacemaker or Cardioverter-Defibrillator Implantation," *J Am Coll Cardiol.*, May 9, 2017; 69(18): 2331-2341.

Cho et al., Cerclage parahisian septal pacing through the septal perforator branch of the great cardiac vein: Bedside-to-bench development of a novel technique and lead, *Heart Rhythm Society*, Dec. 2019; 16(12): 1834-1840.

Chon et al., "TCT-18: Novel Concept of Catheter-Based Treatment for Tricuspid Regurgitation(Cerclage-TR block)," Pusan National University Yangsan Hospital, Yangsan, South Korea NHLBI, NIH, USA Sep. 21, 2018.

Choy et al., "Right ventricular pacing impairs endothelial function in man," *Europace*, Jun. 2011; 13(6):853-858.

Dandamudi et al., "My Approach to Choosing Ventricular Pacing Sites in Patients With Severe Heart Failure," *J Cardio Electrophysiol.*, Jul. 2011; 22(7):813-817.

Dandamudi et al., "How to perform permanent His bundle pacing in routine clinical practice," *Heart Rhythm Society*, Jun. 2016; 13(6):1362-1366.

Dandamudi et al., "The Complexity of the His Bundle: Understanding Its Anatomy and Physiology through the Lens of the Past and the Present," Sep. 2016, DOI: 10.1111/pace.12925.

De Sisti et al., "Adverse Effects of Long-Term Right Ventricular Apical Pacing and Identification of Patients at Risk of Atrial Fibrillation and Heart Failure," PACE, Aug. 2012; 35(8):1035-1043.

Deshmukh et al., "Permanent, Direct His-Bundle Pacing: A Novel Approach to Cardiac Pacing in Patients With Normal Hus-Purkinje Activation," *Circulation*, Feb. 29, 2000, 101(8):869-877.

Deshmukh et al., "Direct His-Bundle Pacing: Present and Future," *PACE*, Jun. 2004; 27 [6 Pt.2]:862-70.

Deshmukh et al., "Direct His-Bundle Triple Site Pacing: A Novel Alternative to Bi-Ventricular Pacing," Heart Rhythm 2009, Presentation Abstract, May 14, 2009.

Deshmukh et al., "Comparison of Direct His Bundle and Biventricular Pacing," Heart Rhythm 2009, Poster Session V, May 15, 2009.

Deshmukh et al., "His bundle pacing: Initial experience and lessons learned," *J Electrocardiol.*, 2016; 49:658-663.

Dreger et al., "Pacing-induced cardiomyopathy in patients with right ventricular stimulation for >15 years," *EP Europace*, Feb. 2012; 14(2):238-242.

El-Sherif et al., "Normalization of Bundle Branch Block Patterns by Distal His Bundle Pacing. Clinical and Experimental Evidence of Longitudinal Dissociation in the Pathologic His Bundle," *Circulation*, Mar. 1978; 57:473-83.

Friedman et al., "Intermittent Capture of the Left Bundle With Permanent His Bundle Pacing: Mechanistic Insights and Implications for an Emerging Field," Aug. 1, 2016. doi: 10.1111/jce.13057.

Fröhlig et al., "His-bundle Stimulation and Alternative RV Stimulation Sites," Mar. 2008; 19(1):30-40, German.

Garrote et al., "His Bundle Pacing: Great in Theory, But Difficult in Practice," Revista Española de Cardiología, 2006; 59(6):534-6.

Gierula et al., "Pacing-associated left ventricular dysfunction? Think reprogramming first!" *Heart*, May 2014; 100(10):765-769.

Gierula et al., "Patients with long-term permanent pacemakers have a high prevalence of left ventricular dysfunction," *J Cardiovasc Med*, Nov. 2015; 16(11):743-750.

Gillis et al., "Atrial Fibrillation After DDDR Pacemaker Implantation," *J Cardiovasc Electrophysiol.*, Jun. 2002;13(6):542-547.

Gula et al., "Feasibility of His Bundle Pacing as an Alternative Pacing Site: Measurement of His Refractoriness," *J Interv Card Electrophysiol.*, 2005; 12: 69-73.

Hayashi et al., "Impact of simple electrocardiogramarkers as predictors for deterioration of left ventricular function in patients with frequent right ventricular apical pacing," *Heart Vessels*, Sep. 26, 2017; 33(3):299-308.

"His-Bundle Pacing Papers" http://www.his-pacing.org/the-list-his-bundle-pacing-papers/, 15 pages.

Hoyt et al., "Reversal of Left Ventricular Dysfunction with Biventricular or His-bundle Pacing Upgrade Late after A-V Nodal Ablation/block," Heart Rhythm 2008 29th Scientific Sessions.

Hoyt et al., "Hemodynamic Evaluation of Direct His-Bundle and Parahisian Pacing," Heart Rhythm 2009, Poster Session V, May 15, 2009.

Huang et al., "Benefits of Permanent His Bundle Pacing Combined With Atrioventricular Node Ablation in Atrial Fibrillation Patients With Heart Failure With Both Preserved and Reduced Left Ventricular Ejection Fraction," *J Am Heart Assoc.*, Apr. 1, 2017; 6(4). pii: e005309.

Huang et al., "Feasibility of His Bundle Pacing in Correct Left Bundle Branch Block in Heart Failure Patients," Journal of the American College of Cardiology, vol. 70, No. 16, Suppl C, 2017, GW28-e1237, 1 page.

Karpawich et al., "Septal His-Purkinje Ventricular Pacing in Canines: A New Endocardial Electrode Approach," *Pacing Clinical Electrophysiology*, 1992; 15:2011-5.

Karpawich et al., "Altered Cardiac Histology Following Apical Right Ventricular Pacing in Patients with Congenital Atrioventricular Block," *Pacing Clin Electrophysiol.*, Sep. 1999; 22(9):1372-7.

Khoo et al., "Right Ventricular Pacing as Backup to His Bundle Pacing to Minimize Battery Drain," Heart Rhythm Society, Scientific Sessions, 2013.

Kiehl et al., "Incidence and predictors of right ventricular pacing-induced cardiomyopathy in patients with complete atrioventricular block and preserved left ventricular systolic function," *Heart Rhythm*, Dec. 2016; 13(12):2272-2278.

Kim et al., "Trans-coronary sinus intraseptal para-Hisian pacing: Cerclage pacing," *Heart Rhythm*, Apr. 2016, 13(4):992-6.

Kim, "Mitral Loop Cerclage a catheter-based treatment of functional mitral regurgitation (CSTV)," JCR 2019, EuroPCR 2018.

Kronborg et al., "Left Ventricular Performance during para-His Pacing in Patients with High-degree Atrioventricular Block: an acute study," *Europace*, Jun. 2014; 14(6):841-6. Epub Dec. 14, 2011.

Kronborg et al., "His or para-His Pacing Preserves Left Ventricular Function in AV Block: a Double-blind, Randomized, Crossover Study," *Europace*, Aug. 2014; 16(8): 1189-96.

(56) References Cited

OTHER PUBLICATIONS

Kronborg et al., "Left ventricular regional remodeling and lead position during cardiac resynchronization therapy," *Heart Rhythm*, Apr. 17, 2018; 15(10):1542-1549.
Kronborg et al., "His Bundle Pacing: Techniques and Outcomes," *Curr Cardiol Rep.*, Jul. 2016;18(8):76.
Laske et al., "Excitation of the Intrinsic Conduction System Through His and Interventricular Septal Pacing," *PACE*, Apr. 2006; 29(4):397-405.
Lederman et al., "Mitral Cerclage Annuloplasty," Cadiovascular Intervention Program at NHLBI, Update 2017.
Lindsay, "Deleterious Effects of Right Ventricular Pacing," *The New England Journal of Medicine*, Nov. 15, 2009; 361:2183-2185.
Lustgarten et al., "Direct His Bundle Pacing vs. BiVentricular Pacing in CRT Patients—A Cross-over Design Comparison," *Heart Rhythm*, 2013.
Lustgarten et al., "His-Bundle vs Biventricular Pacing in Resynchronization Therapy," *Heart Rhythm*, Jul. 2015; 12(7):1548-1557.
Lustgarten et al., "Step-wise Approach to Permanent His Bundle Pacing," *The Journal of Innovations in Cardiac Rhythm Management*, 2016; 7:2313-2321.
Mabo et al., "A Technique For Stable His-bundle Recording and Pacing: Electrophysiological and Hemodynamic Correlates," *Pacing Clinical Electrophysiology*, 1995; 18:1894-901.
Mazza et al., "Incidence and Predictors of Heart Failure Hospitalization and Death in Permanent Pacemaker Patients: a Single-Center Experience over Medium-term Follow-up," Europace (2013) 15. 1267-1272.
Naperkowski et al., "Direct Implantation of Permanent His Bundle Pacing Lead in Patients with Complete Heart Block Without a Mapping Catheter or a Back-up Right Ventricular Lead: Feasibility and One year Follow-up," *Heart Rhythm*, Scientific Sessions, 2013.
Narula, "Longitudinal Dissociation in the His Bundle," *Circulation*, Dec. 1977; 56(6):996-1006.
Niazi et al., "Comparison of Lead Placement Strategies for Permanent His Bundle Pacing," Supplement, May 2011; 8(5).
Occhetta et al., "Prevention of Ventricular Desynchronization by Permanent Para-Hisian Pacing after Atrioventricular Node Ablation in Chronic Atrial Fibrillation," *Journal of the American College of Cardiology*, May 16, 2006; 47(10):1938-45.
Occhetta et al., "Future Easy and Physiological Cardiac Pacing," *Journal of Cardiology*, Jan. 26, 2011; 31(1):32-39.
Padeletti et al., "Rate Stabilization By Right Ventricular Apex or His Bundle Pacing in Patients With Atrial Fibrillation," *Europace*, 2005; 7:454-459.
Pastore et al., "Hisian area and Right Ventricular Apical Pacing Differently Affected Left Atrial Function: an Intra-patient Evaluation," *Europace*; 2013.
Pastore et al., "The Risk of Atrial Fibrillation during Right Ventricular Pacing," *Europace*, Mar. 2016; 18(3):353-8.
Scheinman et al., "Long-term His-Bundle Pacing and Cardiac Function," *Circulation* Feb. 29, 2000; 101:836-837.
Scherlag et al., "Functional aspects of His bundle physiology and pathophysiology: Clinical implications," *J Electrocardiol.*, Jan.-Feb. 2017; 50(1)151-155.
Sharma et al., "Permanent His-bundle Pacing is Feasible, Safe, and Superior to Right Ventricular Pacing in Routine Clinical Practice," *Heart Rhythm*, Feb. 2015; 12(2):305-312.
Sharma, "His Bundle Pacing Or Biventricular Pacing For Cardiac Resynchronization Therapy In Heart Failure: Discovering New Methods For An Old Problem," *J Atr Fibrillation*, Dec. 31, 2016.
Sharma et al., "Permanent His Bundle Pacing for Cardiac Resynchronization Therapy in Patients With Heart Failure and Right Bundle Branch Block," *Circ Arrhythm Electrophysiol.*, Sep. 2018;11(9):e006613.
Sharma et al., "Safety and Feasibility of Permanent His Bundle Pacing Without a Guiding Mapping Catheter or a Back-Up Right Ventricular Lead in Routine Clinical Practice", *Heart Rhythm*, vol. 10, No. 5, May 2013, 1 page.
Su et al., "Pacing and sensing optimization of permanent His-bundle pacing in cardiac resynchronization therapy/implantable cardioverter defibrillators patients: value of integrated bipolar configuration," *EP Europace*, 18(9):1399-1405.
Sweeney et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction," *Circulation*, Jun. 17, 2003; 107(23):2932-2937.
Teng et al., "Physiological mechanisms of QRS narrowing in bundle branch block patients undergoing permanent His bundle pacing," *J Electrocardiol.*, 2016; 49(5):644-648.
Teng et al., "Usefulness of His Bundle Pacing to Achieve Electrical Resynchronization in Patients With Complete Left Bundle Branch Block and the Relation Between Native QRS Axis, Duration, and Normalization," *American Journal of Cardiology*, May 28, 2016; 118(4):527-534.
Thambo et al., "Detrimental ventricular remodeling in patients with congenital complete heart block and chronic right ventricular apical pacing," *Circulation*, Dec. 21, 2004; 110(25):3766-72.
Vijayaraman et al., "Permanent His Bundle Pacing in Patients with Advanced Heart Block: Single Center Experience in Unselected Patients Without Mapping Catheter or Back-Up RV Pacing Lead," Heart Rhythm Society, Scientific Sessions, 2014.
Vijayaraman et al., "Anatomical approach to permanent His bundle pacing: Optimizing His bundle capture," *J Electrocardiol.*, 2016; 49: 649-657.
Vijayaraman et al., "How to Perform Permanent His Bundle Pacing: Tips and Tricks," *Pacing Clin Electrophysiol.*, Dec. 2016; 39(12):1298-1304.
Vijayaraman et al., "The Continued Search for Physiological Pacing Where Are We Now?" *Journal of the American College of Cardiology*, Jun. 27, 2017; 69(25):3099-3114.
Vijayaraman et al., "His Bundle Injury Current during Implantation of Permanent His Bundle Pacing Lead Predicts Excellent Pacing Outcomes," Heart Rhythm Society, Scientific Sessions, 2014.
Vijayaraman et al., "Acute His-Bundle Injury Current during Permanent His-Bundle Pacing Predicts Excellent Pacing Outcomes," Pacing Clinical Electrophysiology, Jan. 14, 2015. doi: 10.1111/pace. 12571.
Vijayaraman et al., "Electrophysiologic Insights Into Site of Atrioventricular Block: Lessons From Permanent His Bundle Pacing," *JACC: Clinical Electrophysiology*, Dec. 2015; 1(6):571-581.
Vijayaraman et al., "Permanent His bundle pacing: Electrophysiological and echocardiographic observations from long-term follow-up," *PACE*, Jul. 2017; 40:883-891.
Vijayaraman et al., "Permanent His Bundle Pacing (HBP): Recommendations From A Multi-Center HBP Collaborative Working Group For Standardization Of Definitions, Implant Measurements And Follow-Up," Oct. 2017; DOI: http://dx.doi.org/10.1016/j.hrthm.
Vijayaraman et al., "His Bundle Pacing," *Journal of the American College of Cardiology*, Aug. 2018; 72(8).
Wilson et al., "Strategically targeting calcium: Altering activation sequence to reverse remodel the failing ventricle," *Heart Rhythm*, Oct. 2018; 15(10):1550-1551.
Worsnick et al., "Direct His Bundle Pacing in a Patient with Complete Heart Block Requiring Implantable Defibrillator," *The Journal of Innovation in Cardiac Rhythm Management*, Aug. 2013; 492.
Yamauchi et al., "Permanent His-Bundle Pacing After Atrioventricular Node Ablation in a Patient With Chronic Atrial Fibrillation and Mitral Regurgitation," *Circ J*, 2005; 69:510-514.
Zanon et al., "A Feasible Approach for Direct His-Bundle Pacing Using a new Steerable Catheter to Facilitate Precise Lead Placement," *JCE*, Jan. 2006; 17:29-33.
Zanon et al., "Direct His Bundle Pacing Preserves Coronary Perfusion Compared With Right Ventricular Apical Pacing: a Prospective, Cross-over Mid-term Stud," *Europace*; May 2008;10(5):580-7.
Zanon et al., "Safety and Performance of a System Specifically Designed for Selective Site Pacing," *Pacing and Clinical Electrophysiology*, Mar. 2011; 34(3):339-347.

(56) References Cited

OTHER PUBLICATIONS

Zanon et al., "Direct His bundle and Parahisian Cardiac Pacing," *A.N.E.*, Apr. 2012; 17(2):70-8.
Znojkiewicz et al., "Direct His-bundle Pacing in Patients Following AV Node Ablation," Heart Rhythm, May 2011; 8(5):Supplement.
Office Action from U.S. Appl. No. 16/162,998 dated Feb. 11, 2021, 7 pages.
Office Action issued in China for Application No. 201880067917.X dated Sep. 29, 2023 (5 pages). English translation included.
Office Action issued in Europe for Application No. 18799938.8 dated Jul. 11, 2023 (6 pages).
Office Action issued in Europe for Application No. 18800375.0 dated Apr. 4, 2023 (4 pages).

\* cited by examiner

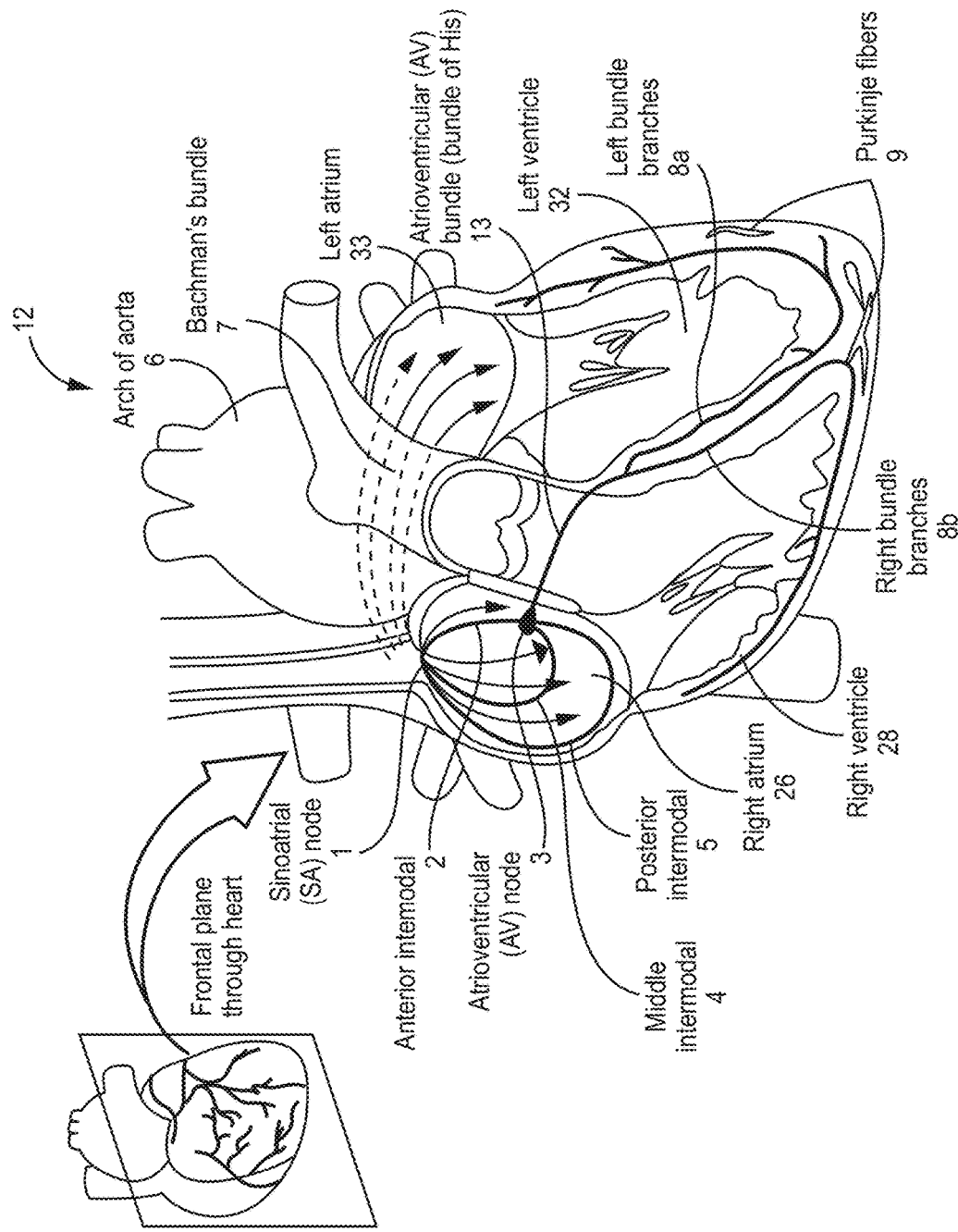

Intrinsic (native)

LBBB

His pacing at Proximal His Bundle

LBBB

His pacing at increase pacing output

Intrinsic (native)

LBBB

His pacing at low pacing output

Intrinsic (native)

LBBB

Pacing with AV delay 40ms

RBBB

Pacing with AV delay 100ms

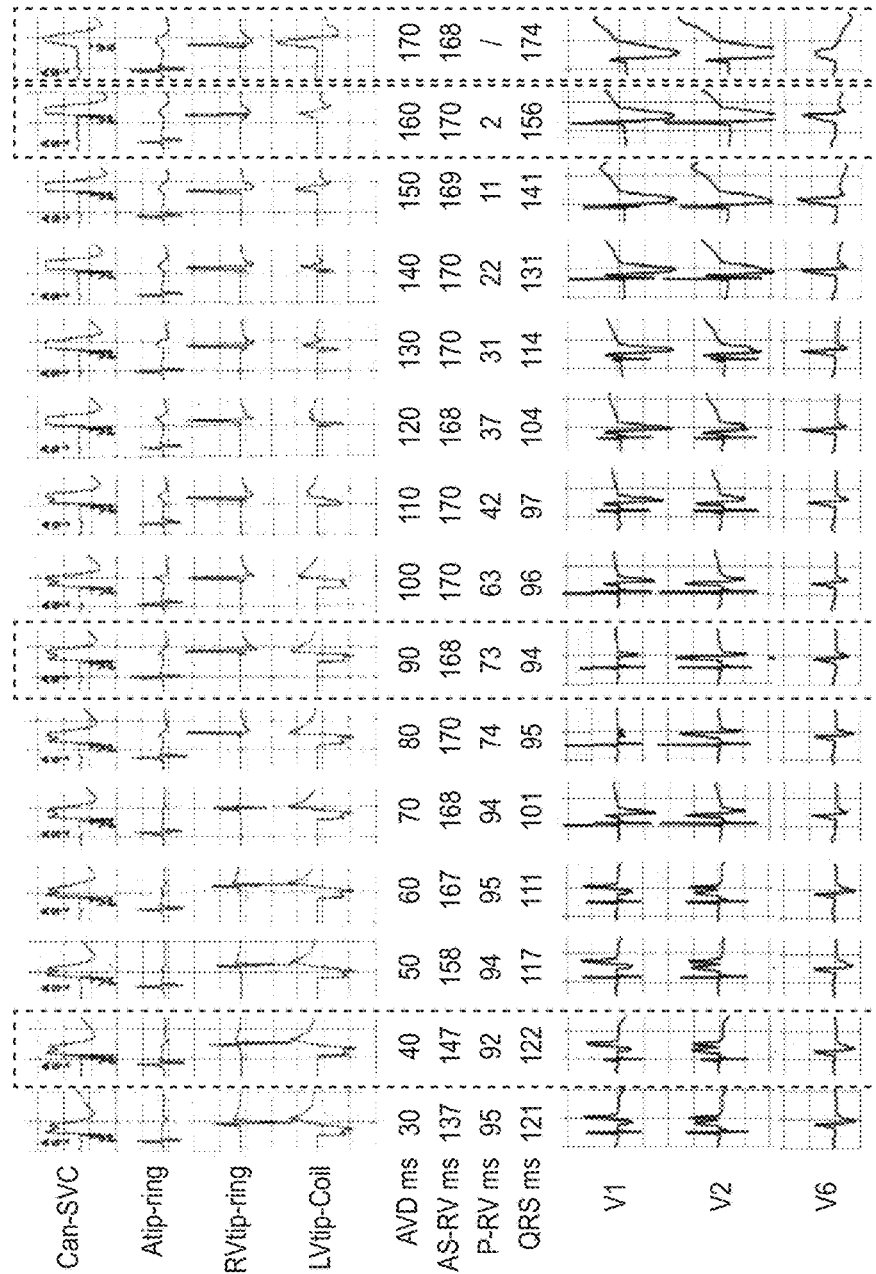

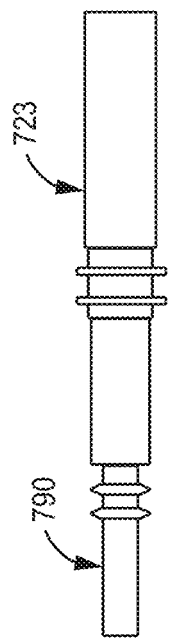
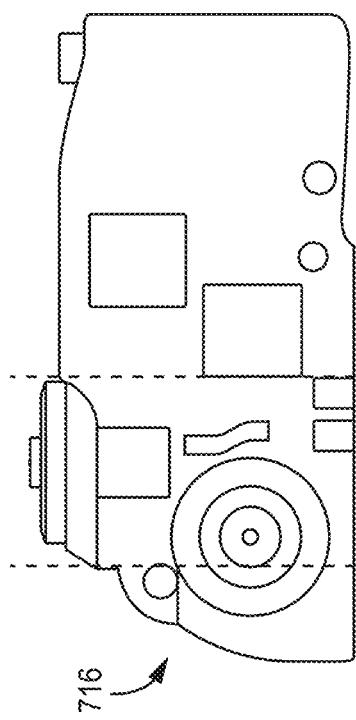
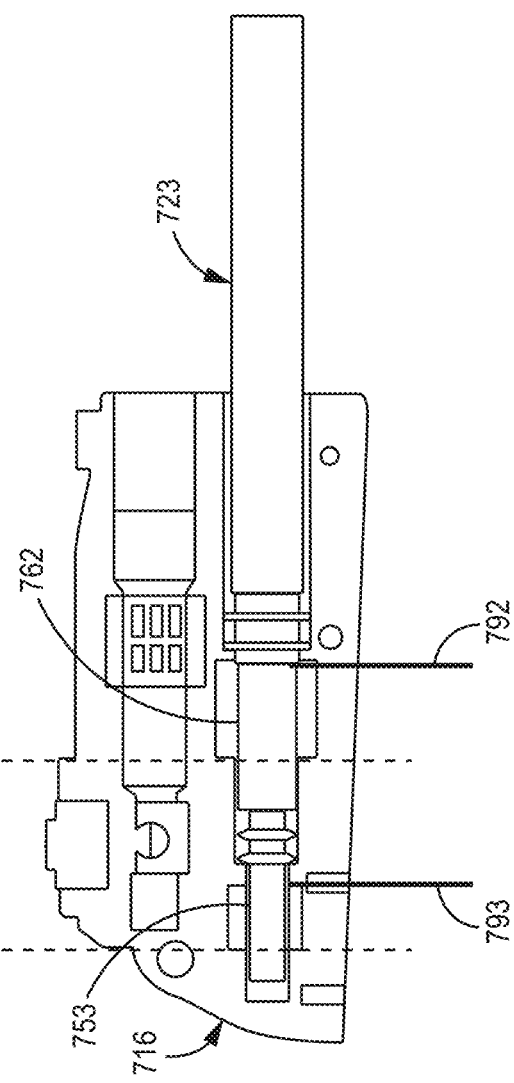
FIG. 28A
FIG. 28B

BUNDLE BRANCH PACING DEVICES AND METHODS

CROSS-REFERENCE TO RELATED APPLICATIONS

This application claims the benefit of U.S. Provisional Application No. 62/573,685, filed Oct. 17, 2017, the benefit of U.S. Provisional Application No. 62/581,486, filed Nov. 3, 2017, and the benefit of U.S. Provisional Application No. 62/617,059, filed Jan. 12, 2018, which are incorporated herein in their entireties.

The present disclosure relates generally to pacing of cardiac tissue, and more particularly, to pacing using the conduction system of the heart, such as the His bundle.

Implantable medical devices (IMDs), such as cardiac pacemakers or implantable cardioverter defibrillators, deliver therapeutic stimulation to patients' hearts thereby improving the lives of millions of patients living with heart conditions. Conventional pacing techniques involve pacing one or more of the four chambers of patient's heart 12—left atrium (LA) 33, right atrium (RA) 26, left ventricle (LV) 32 and right ventricle (RV) 28, all of which are shown in FIG. 1. One common conventional therapeutic pacing technique that treats a slow heart rate, referred to as Bradycardia, involves delivering an electrical pulse to a patient's right ventricular tissue. In response to the electrical pulse, both the right and left ventricles contract. However, the heart beat process may be significantly delayed because the pulse travels from the right ventricle through the left ventricle. The electrical pulse passes through the muscle cells that are referred to as myocytes. Myocyte-to-myocyte conduction may be very slow. Delayed electrical pulses can cause the left ventricle to be unable to maintain synchrony with the right ventricle.

Over time, the left ventricle can become significantly inefficient at pumping blood to the body. In some patients, heart failure can develop such that the heart is too weak to pump blood to the body. Heart failure may be a devastating diagnosis since, for example, fifty percent of the heart failure patients have a life expectancy of five years. To avoid the potential development of heart failure, some physicians have considered alternative pacing methods that involve the cardiac conduction system. The cardiac conduction system, like a "super highway," may be described as quickly conducting electrical pulses whereas pacing cardiac muscle tissue may slowly conduct electrical pulses, like "traveling on a dirt road."

The cardiac conduction system includes sinoatrial node (SA node) 1, atrial internodal tracts 2, 4, 5 (i.e., anterior internodal 2, middle internodal 4, and posterior internodal 5), atrioventricular node (AV node) 3, His bundle 13 (also known as atrioventricular bundle or bundle of His), and right and left bundle branches 8a, 8b. FIG. 1 also shows the arch of aorta 6 and Bachman's bundle 7. The SA node, located at the junction of the superior vena cava and right atrium, is considered to be the natural pacemaker of the heart since it continuously and repeatedly emits electrical impulses. The electrical impulse spreads through the muscles of right atrium 26 to left atrium 33 to cause synchronous contraction of the atria. Electrical impulses are also carried through atrial internodal tracts to atrioventricular (AV) node 3—the sole connection between the atria and the ventricles. Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His. His bundle 13 is located in the membranous atrioventricular septum near the annulus of the tricuspid valve. His bundle 13 splits into right and left bundle branches 8a, 8b and are formed of specialized fibers called "Purkinje fibers" 9. Purkinje fibers 9 may be described as rapidly conducting an action potential down the ventricular septum (VS), spreading the depolarization wavefront quickly through the remaining ventricular myocardium, and producing a coordinated contraction of the ventricular muscle mass.

While His bundle pacing is increasingly used as an alternative to traditional pacing techniques, His bundle pacing has not been widely adopted for a variety of reasons. For example, His pacing electrodes should be positioned within a precise target location (e.g., within about 1 millimeter) of the His bundle, which may be difficult. Further, some physicians insert the pacing electrode in a manner that damages the His bundle thereby causing complete block or bundle branch block timing of delivery of pacing pulses not being optimal. Additionally, some physicians place the His lead in a proximal His bundle position that requires a much higher pacing output to be delivered by the pacemaker to effectively pace the His bundle. It is desirable to develop new methods and systems of His bundle pacing that overcome some of the disadvantages associated with His bundle pacing alone or in combination with other pacing therapies.

SUMMARY

The techniques of this disclosure generally relate to pacing the special cardiac conductive system, e.g., the His-Purkinje system, including His bundle and bundle branches. A conduction block can either exist due to disease progression, such as AV block or infra-Hisian block, or appear during the lead implantation procedure that causes bundle injury or otherwise affects bundle conduction. In such cases, conventional His bundle pacing may not work properly. For example, activation can propagate via one bundle branch but not the other one. Thus, this disclosure provides bundle branch pacing by bypassing the block region and algorithms that allow better pacing timing and output to provide a better ventricular synchronization than conventional His bundle pacing. For example, if a pacing lead is placed near the left bundle branch and a low pacing output only excites the left bundle branch but not the right bundle branch, an algorithm of the present disclosure will adjust pacing timing to synchronize the activation generated by pacing with intrinsic activation via the right bundle branch, which may result in a normal ventricular synchronization. In another example, if the lead placement damages or otherwise affects the right bundle branch and can only stimulate the left bundle branch, which may lead to an electrocardiogram (ECG) representing a right bundle branch block, or a sign of ventricular dyssynchrony, then a new lead of the present disclosure may be used to stimulate both left and right bundle branches at the same time to achieve synchronized right and left ventricular activation.

In one aspect, the present disclosure provides a method of using a pacemaker for His-bundle or bundle-branch pacing of a patient's heart. The method includes sensing heart activity using a set of electrodes associated with the pacemaker. The method also includes using a processor in the pacemaker to determine whether one of a QRS parameter and an activation interval acquired from the sensed heart activity is greater than a first threshold. The method also includes, in response to determining whether the QRS parameter or activation interval is greater than the first threshold, using the processor to determine whether bundle pacing should be delivered earlier or later. Further, the method includes, in response to determining whether bundle pacing should be delivered earlier or later, using the processor to adjust a time interval for bundle pacing.

In another aspect, the present disclosure provides a method of using an implantable medical device having a processor and an electrical pulse generator. The method includes using the processor to control the electrical pulse generator to adjust delivery of bundle pacing. The processor is configured to measure a QRS parameter and determine whether the QRS parameter is larger than a threshold. The processor is further configured to, in response to determining that the QRS parameter is greater than or equal to the threshold, adjust a bundle-pacing to ventricular-activation interval or a bundle pacing output level. The processor is further configured to deliver bundle pacing using the adjusted bundle-pacing to ventricular-activation interval or using the adjusted bundle pacing output level.

In another aspect, the present disclosure provides an implantable medical device for His-bundle or bundle-branch pacing of a patient's heart. The device includes a sensing circuit configured to sense an atrial event (As) and a ventricular event (Vs). The device also includes an electrical pulse generator configured to generate and deliver electrical His-bundle or bundle-branch stimulation pulses (Vp). The device also includes a processor coupled to the sensing circuit and the electrical pulse generator and configured to control the electrical pulse generator to deliver said Vp on expiration of a defined AV interval or Vp-Vs interval following a said As or Vs. The processor is further configured to determine whether Vp timing should be adjusted. The processor is also configured to, in response to determining that the Vp timing should be adjusted, determine whether Vp should be delivered earlier or later. The processor is also configured to, in response to determining whether the Vp should be delivered earlier or later, decrease an AV delay if the Vp should be delivered earlier or increase the AV delay in response to determining Vp should be delivered later. Further, the processor is configured to generate a set of AV delays that are stored in memory based on iterating through decreases or increases in the AV delay. The processor is further configured to select an optimal AV delay from the set of AV delays stored in memory. The processor is also configured to use the optimal AV delay when delivering His-bundle or bundle-branch pacing.

In another aspect, the present disclosure provides an implantable medical device for His-bundle or bundle-branch pacing of a patient's heart. The device includes a sensing circuit configured to sense an atrial event (As) and a ventricular event (Vs). The device also includes an electrical pulse generator configured to generate and deliver electrical His-bundle or bundle-branch stimulation pulses (Vp). The device further includes a processor coupled to the sensing circuit and the electrical pulse generator and configured to control the electrical pulse generator to deliver said Vp on expiration of a defined AV interval or Vp-Vs interval following a said As or Vs. The processor is further configured to determine whether RV activation occurs earlier than LV activation. The processor is also configured to, in response to determining RV activation occurs earlier than LV activation, adjust Vp timing to deliver His-bundle or bundle-branch pacing based on an LV activation time.

In another aspect, the present disclosure provides an implantable medical device for His-bundle or bundle-branch pacing of a patient's heart. The device includes a sensing circuit configured to sense an atrial event (As) and a ventricular event (Vs). The device also includes an electrical pulse generator configured to generate and deliver electrical His-bundle or bundle-branch stimulation pulses (Vp). The device also includes a processor coupled to the sensing circuit and the electrical pulse generator and configured to control the electrical pulse generator to deliver said Vp on expiration of a defined AV interval or Vp-Vs interval following a said As or Vs. The processor is further configured to determine whether RV activation occurs earlier than LV activation. The processor is also configured to, in response to determining that RV activation does not occur earlier than LV activation, determine whether RV activation occurs later than LV activation. The processor is also configured to, in response to determining RV activation occurs later than LV activation, adjust Vp timing to deliver His-bundle or bundle-branch pacing based on an RV activation time.

In another aspect, the present disclosure provides a method of using a pacemaker for His-bundle or bundle-branch pacing of a patient's heart. The method includes sensing electrical activity of the patient's heart including an atrial event (As) and a ventricular event (Vs). The method also includes detecting dyssynchrony based on the sensed electrical activity of the patient's heart during the patient's intrinsic rhythm or during pacing. The method further includes adjusting delivery of His-bundle or bundle-branch stimulation pulses (Vp) based on the dyssynchrony detected.

In another aspect, the present disclosure provides, a method of using a pacemaker for His-bundle or bundle-branch pacing of a patient's heart. The method includes sensing electrical activity of the patient's heart including an atrial event (As) and a ventricular event (Vs). The method also includes detecting a right bundle branch block (RBBB) pattern or left bundle branch block (LBBB) pattern in the sensed electrical activity of the patient's heart during the patient's intrinsic rhythm or during pacing. The method further includes adjusting the delivery of His-bundle or bundle-branch stimulation pulses (Vp) based on the detected bundle-branch-block pattern.

In another aspect, the present disclosure provides an implantable medical device for bundle-branch pacing of a patient's heart. The device includes a plurality of electrodes. The plurality of electrodes includes a left bundle branch (LBB) cathode electrode positionable, when implanted, on a left side of the septum of the patient's heart proximate to the LBB. The plurality of electrodes also includes a right bundle branch (RBB) cathode electrode positionable, when implanted, implantable on a right side of the septum of the patient's heart proximate to the RBB. The device includes an electrical pulse generating circuit coupled to the plurality of electrodes to generate and deliver electrical bundle-branch stimulation pulses (Vp). The device also includes a processor coupled to the electrical pulse generating circuit. The processor is configured to control the electrical pulse generating circuit to deliver synchronized left and right bundle-branch Vp using the plurality of electrodes based on one or both of an atrial event (As) and a ventricular event (Vs).

In another aspect, the present disclosure provides a method of using a pacemaker for bundle-branch pacing of a patient's heart. The method includes sensing electrical activity of the patient's heart including an atrial event (As) and a ventricular event (Vs). The method also includes delivering synchronized left and right bundle-branch stimulation pulses (Vp) using left and right bundle-branch cathode electrodes based on one or both of As and Vs. The left bundle branch (LBB) cathode electrode is implantable on a left side of the septum of the patient's heart proximate to the LBB of the patient's heart. The right bundle branch (RBB) cathode electrode is implantable on a right side of the septum of the patient's heart proximate to the RBB.

In another aspect, the present disclosure provides a method of positioning a bundle pacing electrode in a patient's heart. The method includes monitoring electrical activity of the patient's heart using one or both of an external electrode and a bundle pacing electrode on a bundle pacing lead or leadless device. The method also includes rotating or advancing the bundle pacing lead or leadless device toward the His bundle or bundle branch of the patient's heart while intermittently applying pacing with the bundle pacing electrode. The method also includes determining whether an RBBB pattern is present based on the monitored electrical activity. Further, the method includes determining whether the patient's heart has a right bundle branch block (RBBB). The method also includes, in response to determining that an RBBB pattern is present during applied pacing and that the patient's heart does not have a RBBB, fixing the bundle pacing lead or leadless device for left bundle branch pacing.

In another aspect, the present disclosure provides a leadless pacing device (LPD) for His-bundle or bundle-branch pacing in a patient's heart. The LPD includes an intracardiac housing and a plurality of electrodes. The plurality of electrodes includes a bundle pacing electrode leadlessly connected to the housing and implantable proximate to or in the His bundle or bundle branch of the patient's heart. The LPD also includes a sensing circuit operably coupled to the plurality of electrodes and configured to sense one or both of an atrial event (As) and a ventricular event (Vs) using at least one of the plurality of electrodes. Further, the LPD includes an electrical pulse generator coupled to the bundle pacing electrode, the electrical pulse generator configured to generate and deliver electrical His-bundle or bundle-branch stimulation pulses (Vp) based on one or both of As and Vs to the patient's heart using the bundle pacing electrode.

In another aspect, the present disclosure provides a leadless pacing device (LPD) for His-bundle or bundle-branch pacing in a patient's heart. The LPD includes an intracardiac housing. The LPD also includes a communication interface disposed in the housing configured to receive signals from a subcutaneously implanted device (SD). The LPD further includes a controller disposed in the housing operatively coupled to at least one electrode configured to deliver His-bundle or bundle-branch pacing pulses to the patient's heart in response to the received signals.

In another aspect, the present disclosure provides a method of His-bundle or bundle-branch pacing. The method includes using a subcutaneously implanted device (SD) to sense far-field electrical signals. The method also includes determining a QRS parameter or activation based on the far-field electrical signals. The method also includes communicating a timing to a leadless pacing device (LPD) to deliver His-bundle or bundle-branch pacing using an atrial-activation to bundle-pacing interval.

BRIEF DESCRIPTION

FIG. 1 is a schematic diagram of a heart of patient (prior art).

Figure 9A:
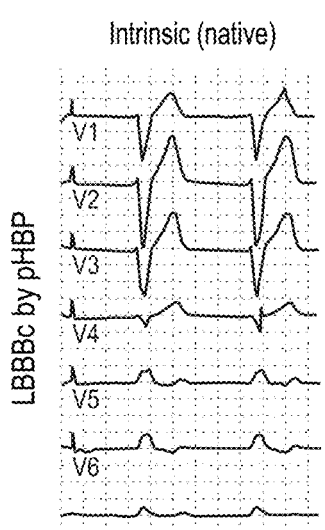

FIG. 9A graphically depicts unipolar ECG signals of intrinsic conduction (native rhythm) acquired from a set of electrodes disposed over cardiac tissue including the His bundle.

Figure 9B:
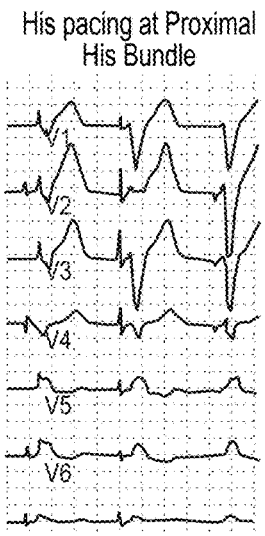

FIG. 9B graphically depicts unipolar ECG signals, acquired from a set of electrodes, in response to proximal His bundle pacing being delivered at a low pacing output.

Figure 9C:
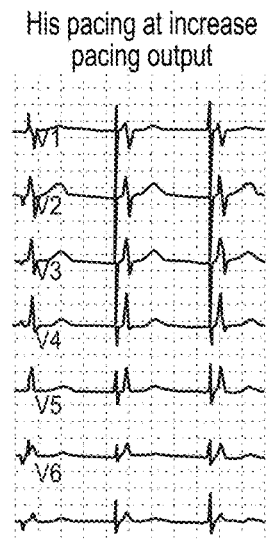

FIG. 9C graphically depicts unipolar ECG signals, acquired from a set of electrodes, in response to proximal His bundle pacing being delivered with a high or increased pacing output compared to the pacing output delivered in FIG. 9B.

Figure 10A:
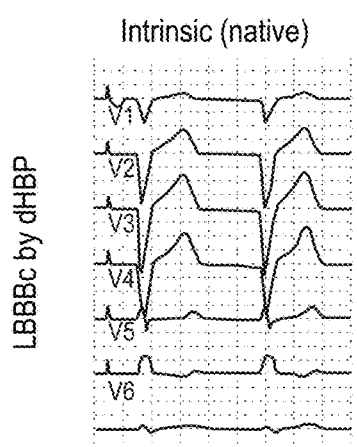

FIG. 10A graphically depicts unipolar ECG signals of intrinsic conduction (native rhythm) acquired from a set of electrodes disposed over cardiac tissue including the His bundle.

Figure 10B:
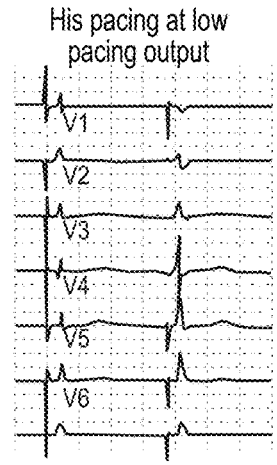

FIG. 10B graphically depicts unipolar ECG signals, acquired from a set of electrodes, in response to distal His bundle pacing being delivered at low pacing output.

Figure 11A:
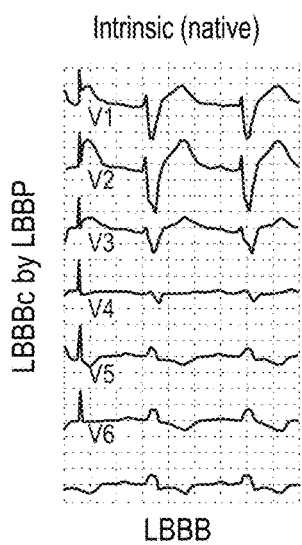

FIG. 11A graphically depicts unipolar ECG signals of intrinsic conduction (native rhythm) acquired from a set of electrodes disposed over cardiac tissue including the His bundle.

Figure 11B:
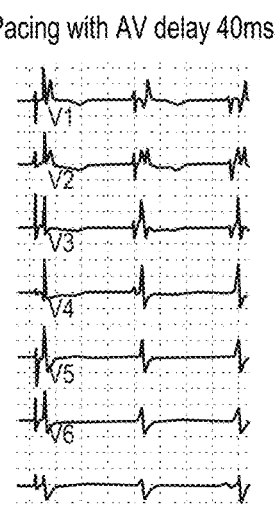

FIG. 11B graphically depicts unipolar ECG signals, acquired from a set of electrodes, responsive to bundle pacing being delivered to the left bundle branch using an atrioventricular delay of 40 milliseconds (ms).

Figure 11C:
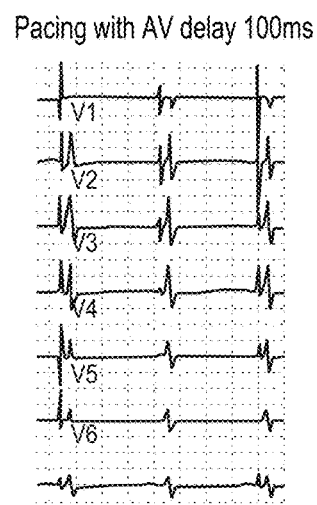

FIG. 11C graphically depicts unipolar ECG signals acquired from a set of electrodes responsive to bundle pacing being delivered to the left bundle branch using an atrioventricular delay of 100 ms.

Figure 12:
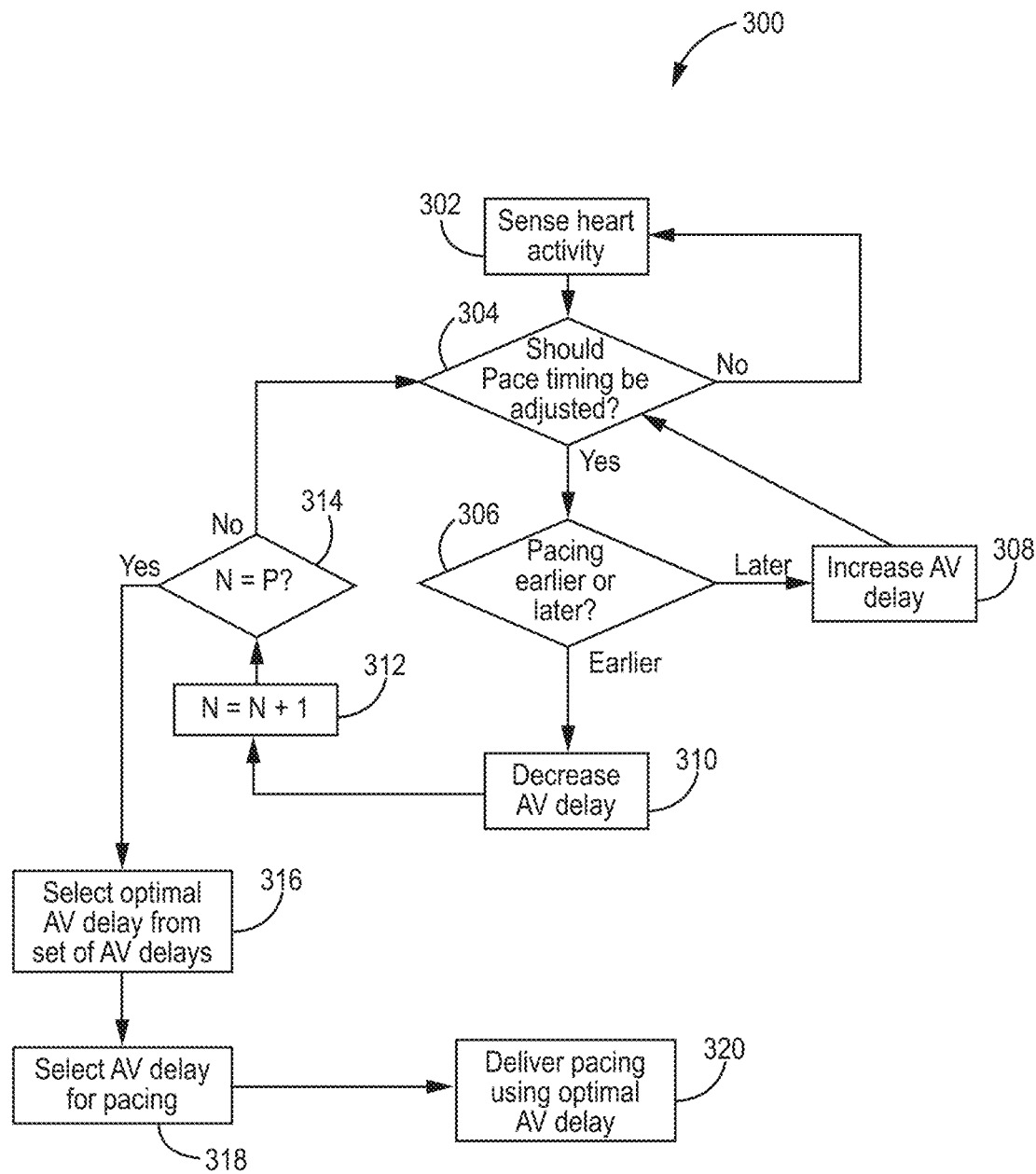

FIG. 12 is a flow diagram of an illustrative process of determining an optimal atrioventricular (AV) delay for delivering bundle pacing with an implantable medical device.

Figure 13:
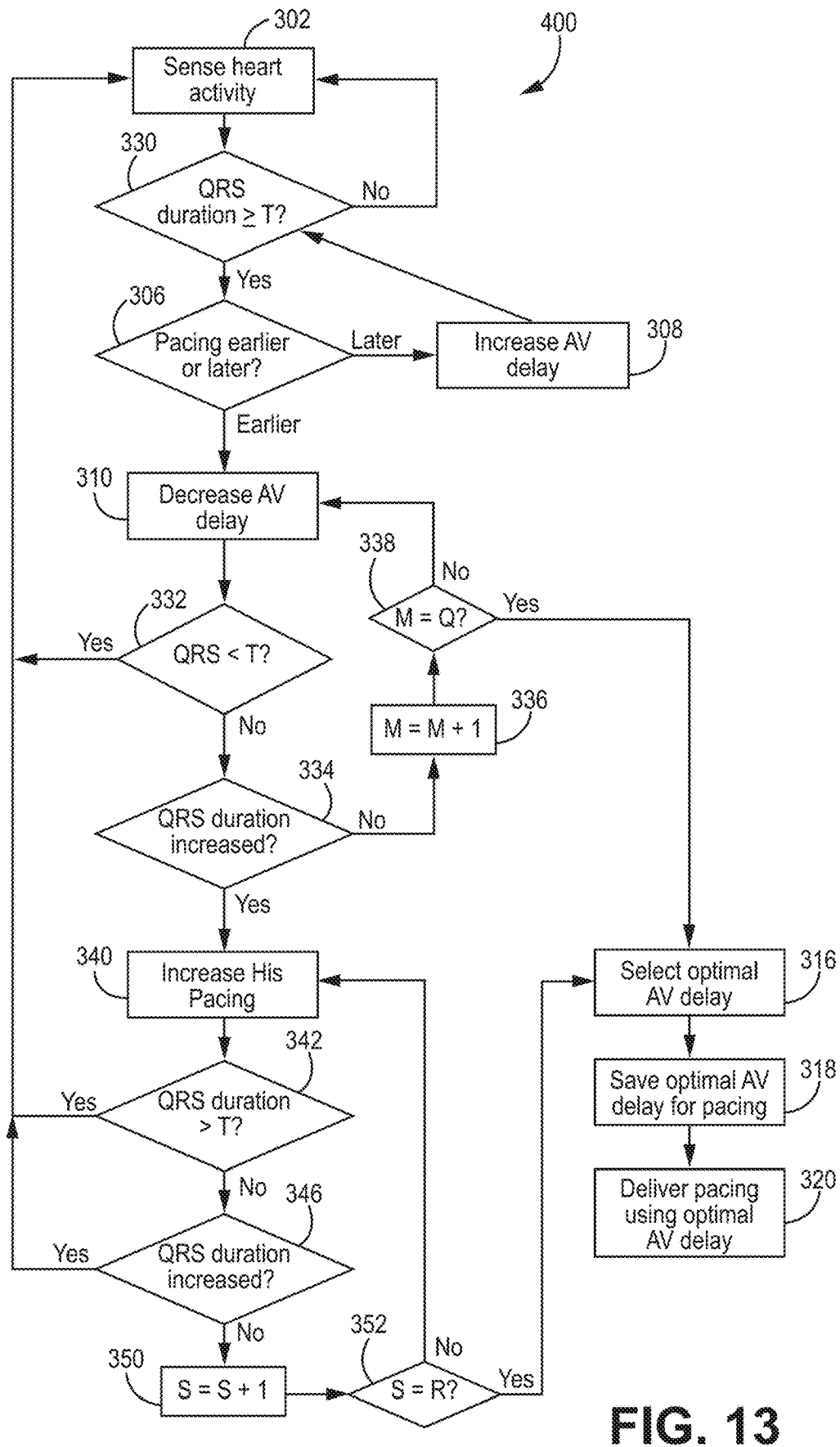

FIG. 13 is a flow diagram of another illustrative process of determining an optimal AV delay for delivering bundle pacing with an implantable medical device.

Figure 14:
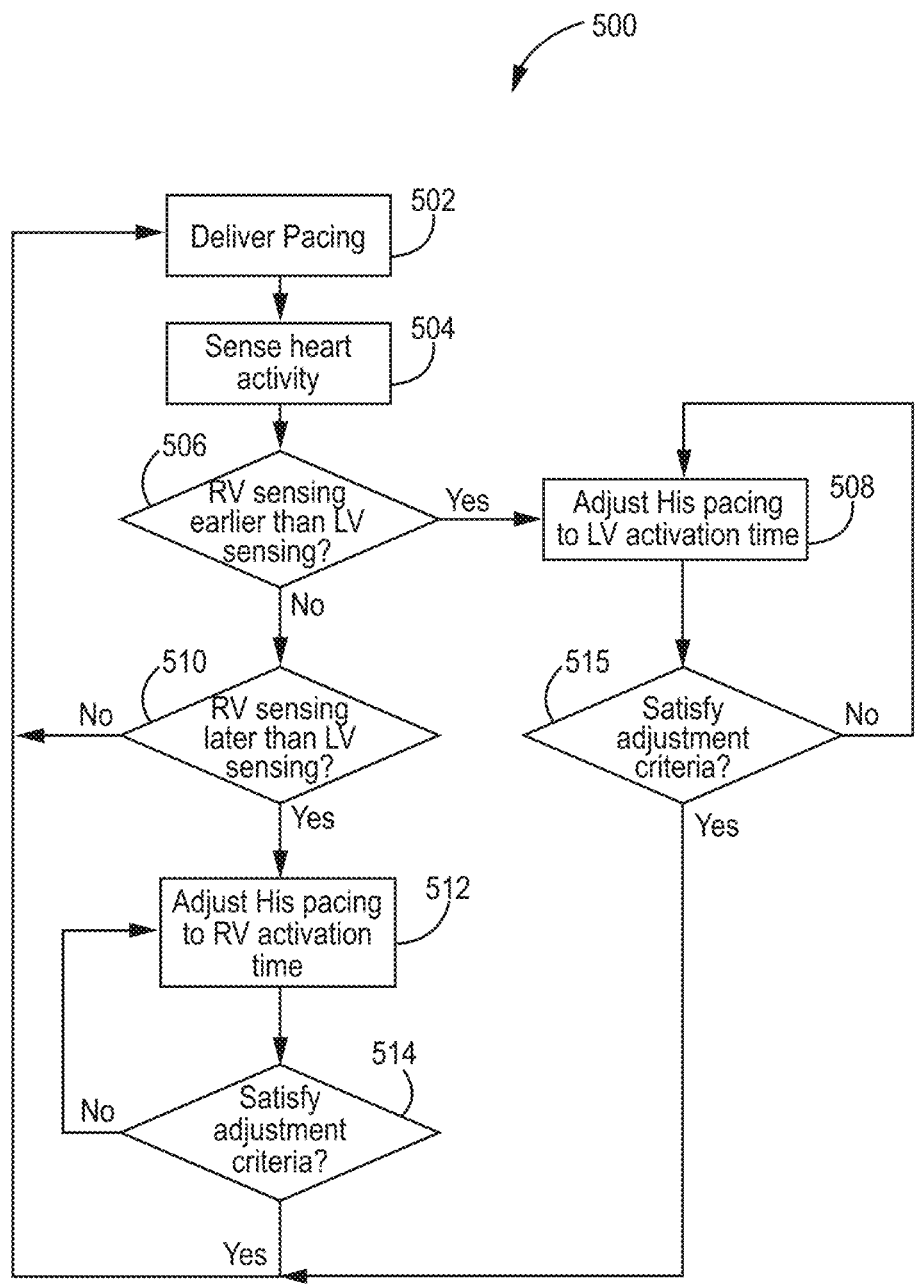

FIG. 14 is a flow diagram of an illustrative process of determining an optimal interventricular (VV) delay for delivering bundle pacing with an implantable medical device.

Figure 15:
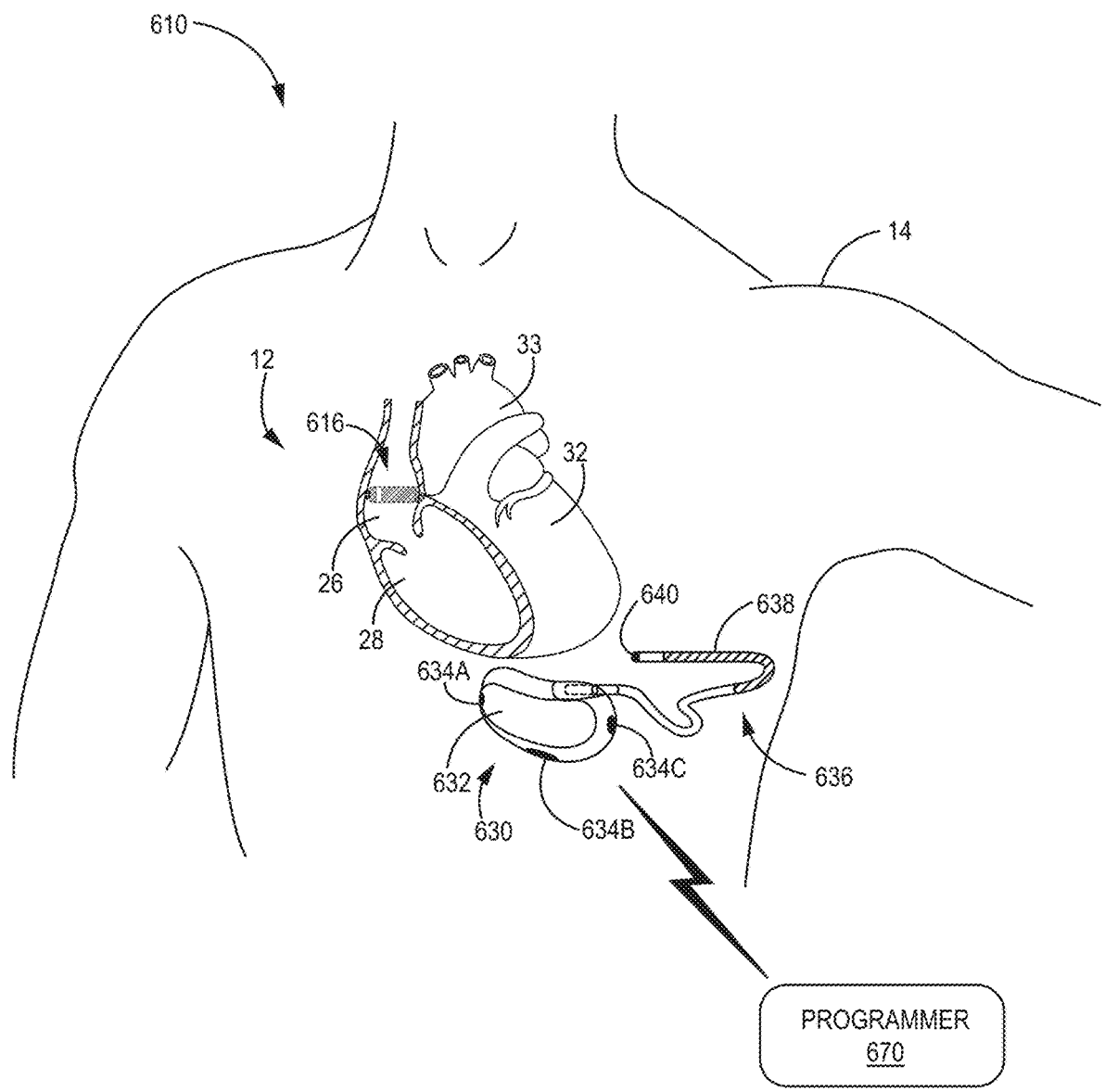

FIG. 15 is a conceptual drawing illustrating an example system that includes a subcutaneous implantable cardioverter defibrillator (SICD) implanted exterior to the rib cage of a patient and a leadless pacing device (LPD) implanted within a cardiac chamber of the patient.

Figure 16:
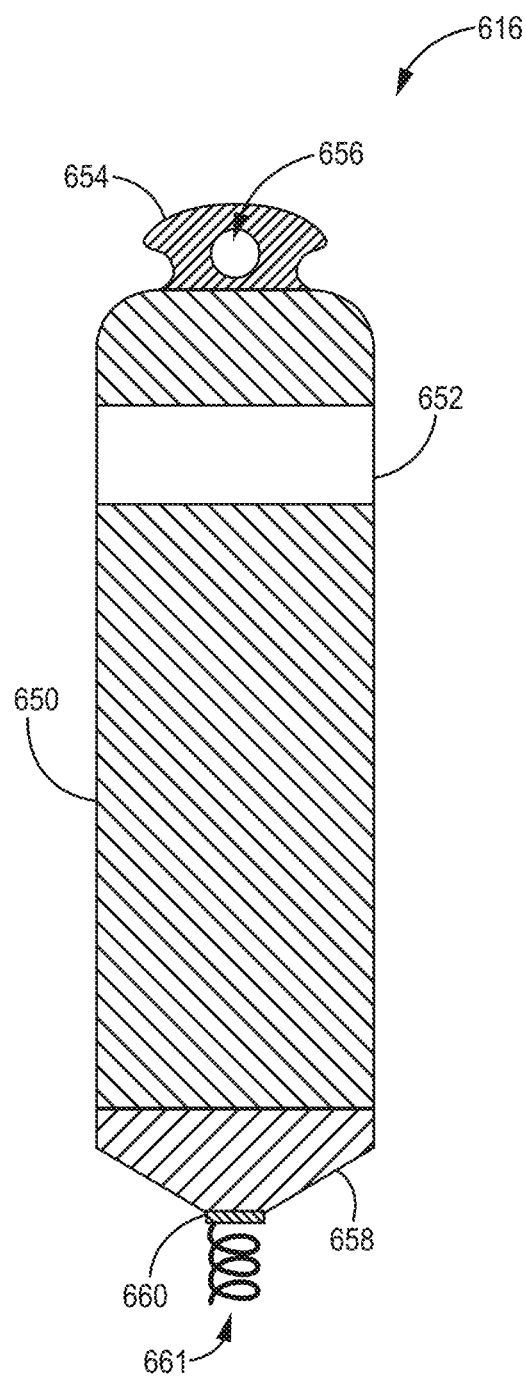

FIG. 16 is a conceptual drawing illustrating the example LPD of FIG. 15.

Figure 17A:
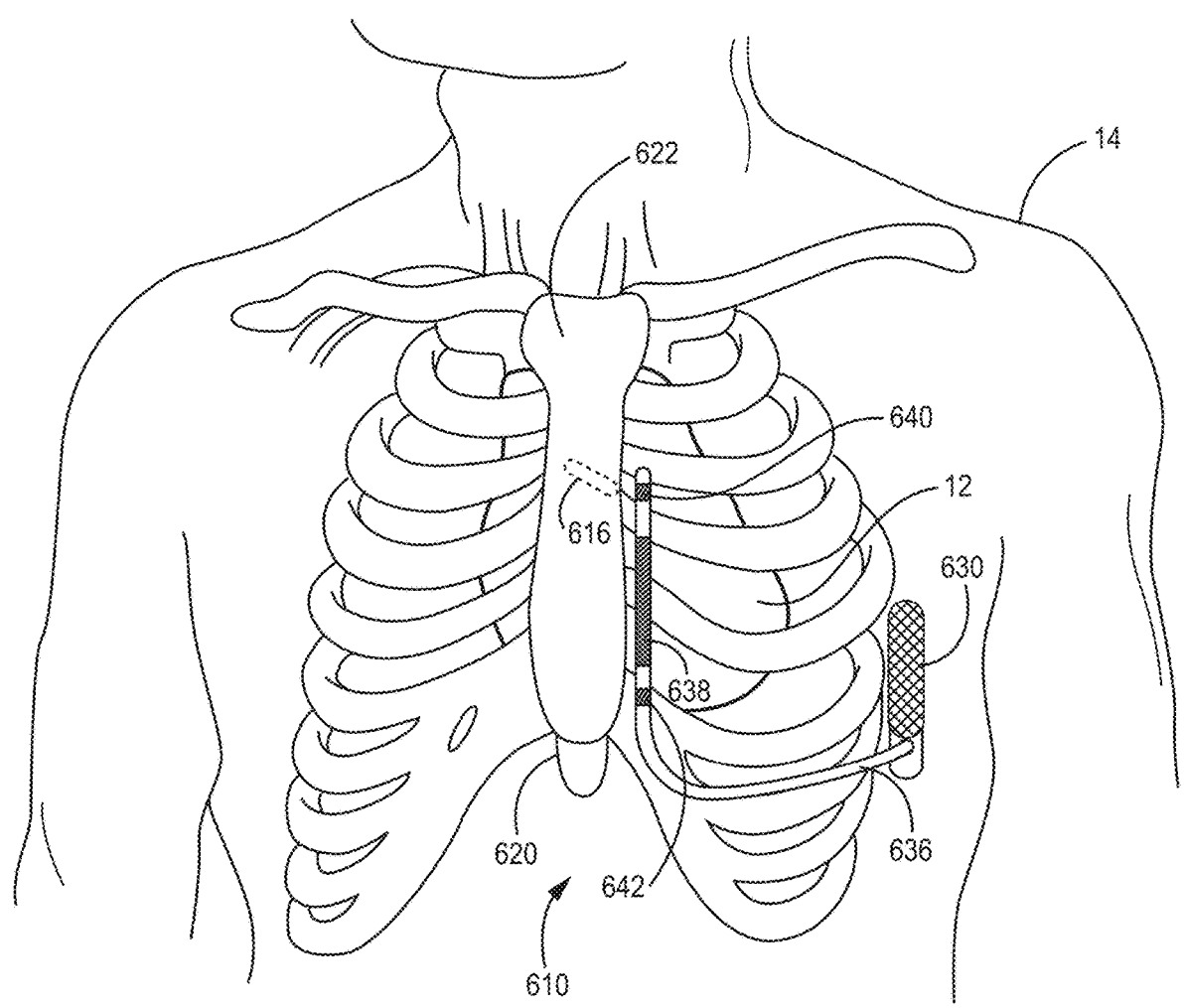

FIG. 17A is a front view of a patient implanted with an implantable cardiac system that includes a subcutaneous device and a leadless pacing device.

Figure 17B:
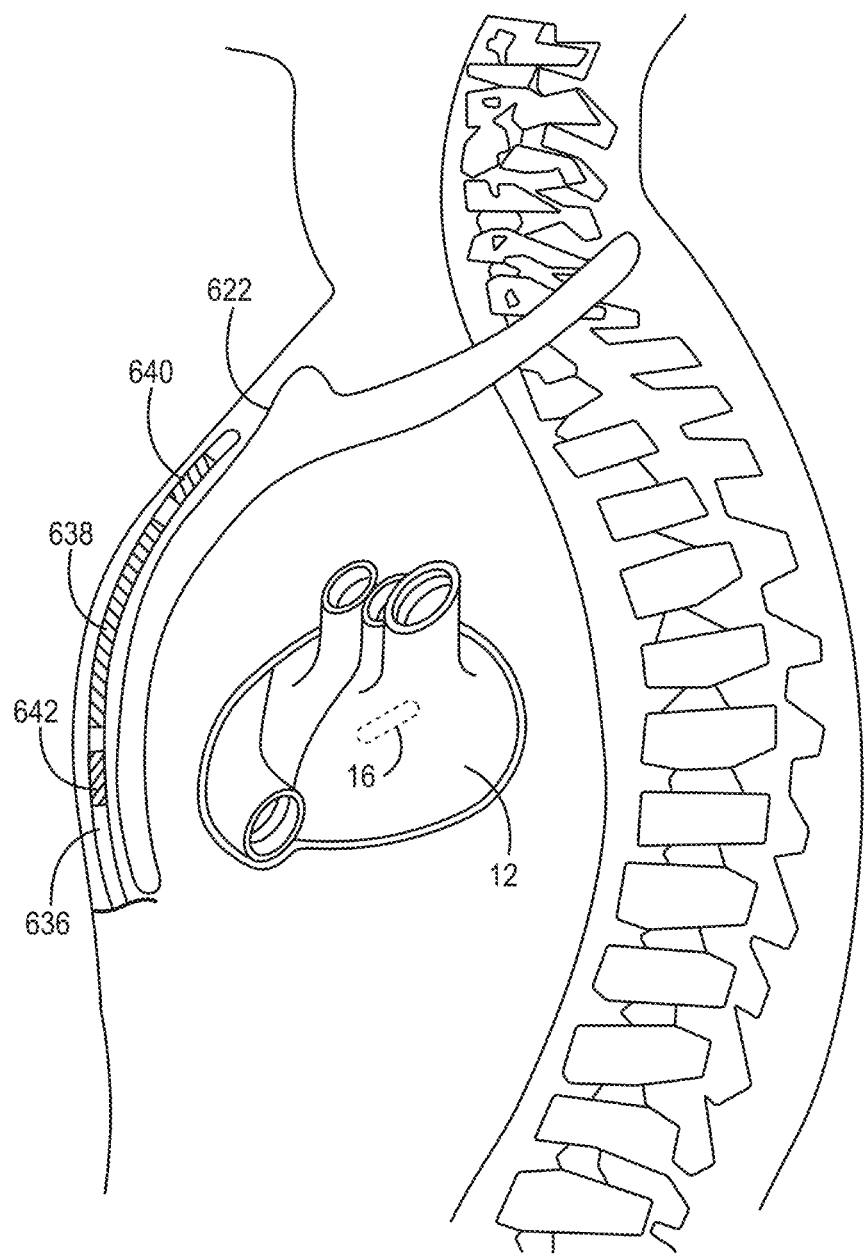

FIG. 17B is a side view of a patient with the implantable cardiac system shown in FIG. 17A.

Figures 18A, 18B:
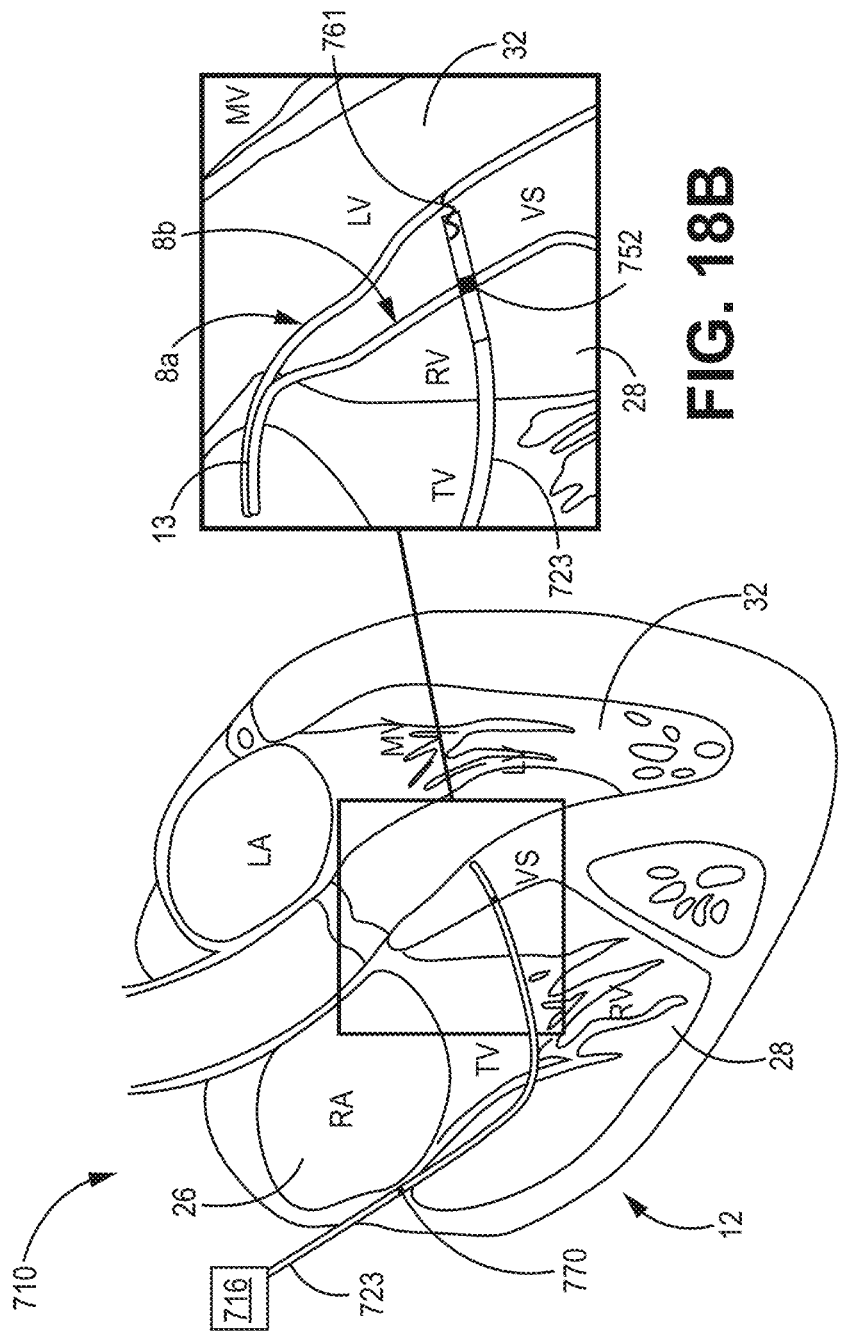

FIG. 18A is a cross-sectional view of a patient's heart implanted with an implantable medical electrical lead to deliver bundle branch pacing.

FIG. 18B is a close-up view of the lead in the patient's heart of FIG. 18A.

FIGS. 19A-D graphically depict electrogram (EGM) signals (at the top) and unipolar ECG signals (at the bottom) representing conduction using various intrinsic or pacing configurations.

FIG. 19E depicts a portion of the patient's heart having a left bundle branch block (LBBB) with intrinsic conduction (native rhythm).

FIG. 19F depicts a portion of the patient's heart in which pacing is applied distal to the block with an AV delay of 40 ms.

FIG. 19G depicts a portion of the patient's heart in which pacing is applied distal to the block with an AV delay of 90 ms.

FIG. 19H depicts a portion of the patient's heart in which pacing is applied distal to the block with an AV delay of 160 ms.

Figure 20:
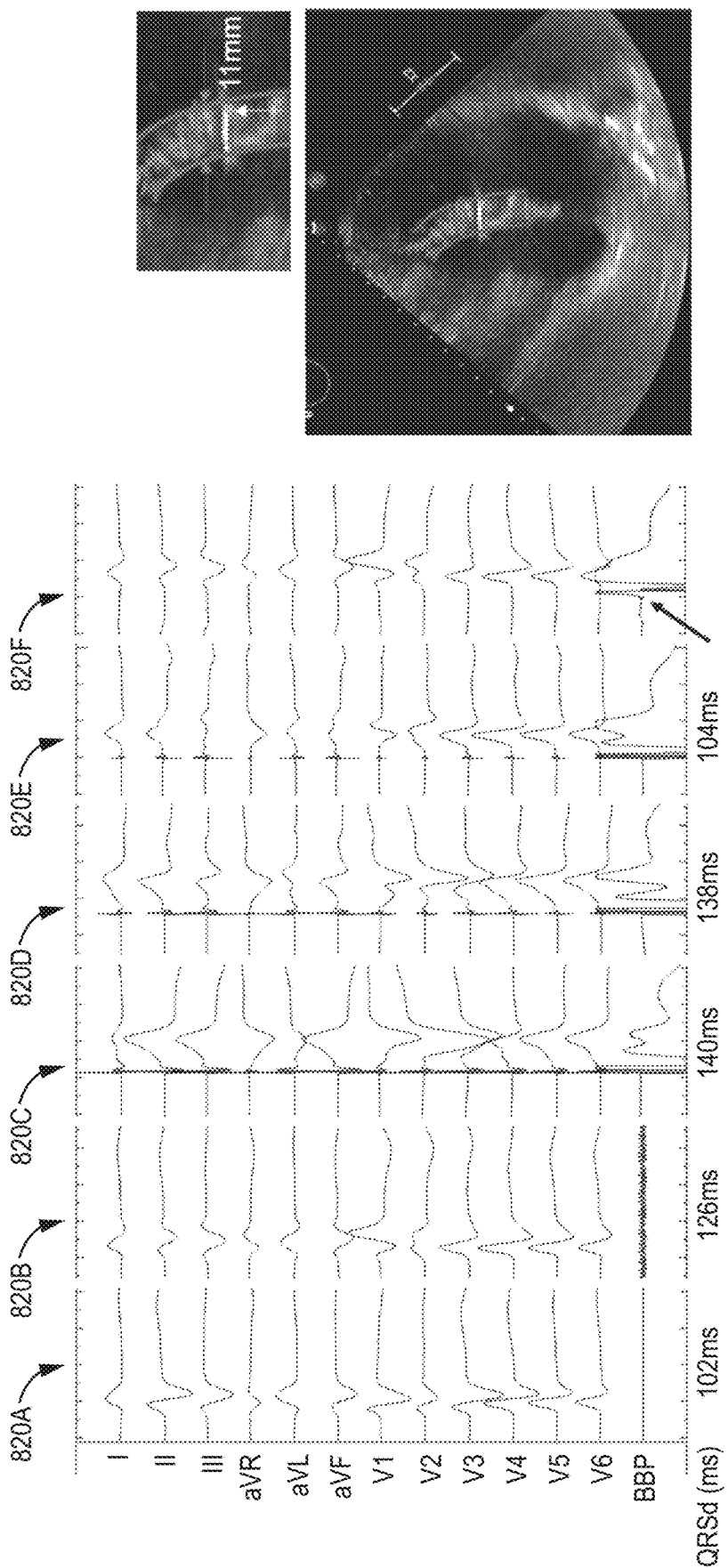

FIG. 20 graphically depicts unipolar ECG signals, acquired from a set of electrodes, in response to various intrinsic or pacing configurations for a patient with an LBBB and resulting QRS duration.

Figure 21:
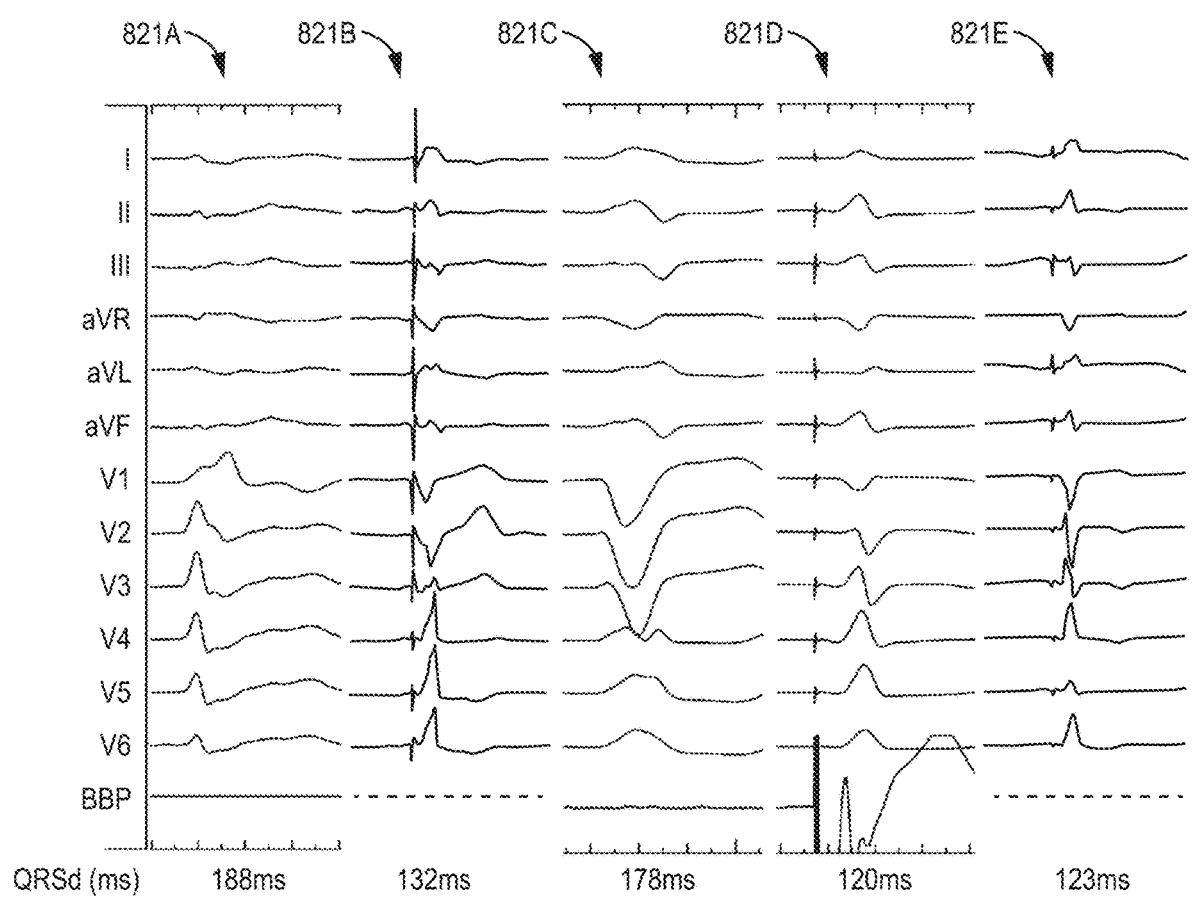

FIG. 21 graphically depicts unipolar ECG signals, acquired from a set of electrodes, in response to various intrinsic or pacing configurations for a patient with an RBBB and resulting QRS durations.

Figure 22A:
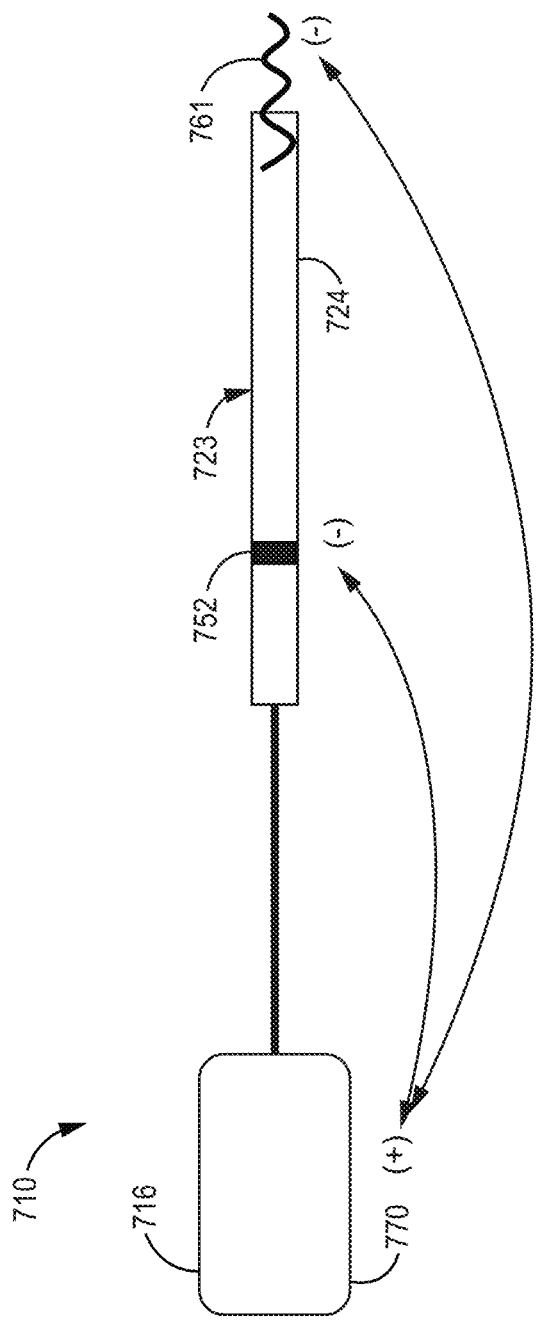

FIG. 22A schematically depicts a lead configured to deliver bundle branch pacing through a helical tip electrode (i.e., cathode) and a ring electrode (i.e., cathode) while the anode is remotely positioned on the housing of the implantable medical device (i.e., pacemaker, ICD).

Figure 22B:
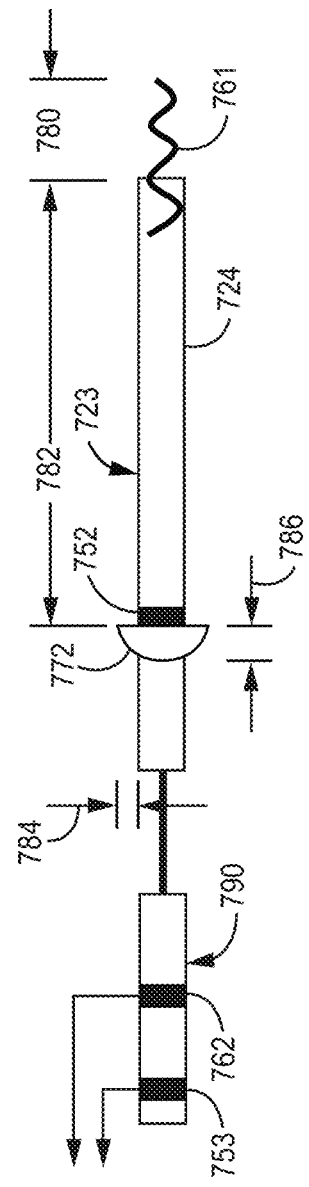

FIG. 22B schematically depicts a lead configured to deliver bundle branch pacing with a shield, proximal to the helical tip electrode, to prevent the helical tip from being "over screwed" into tissue.

Figure 23:
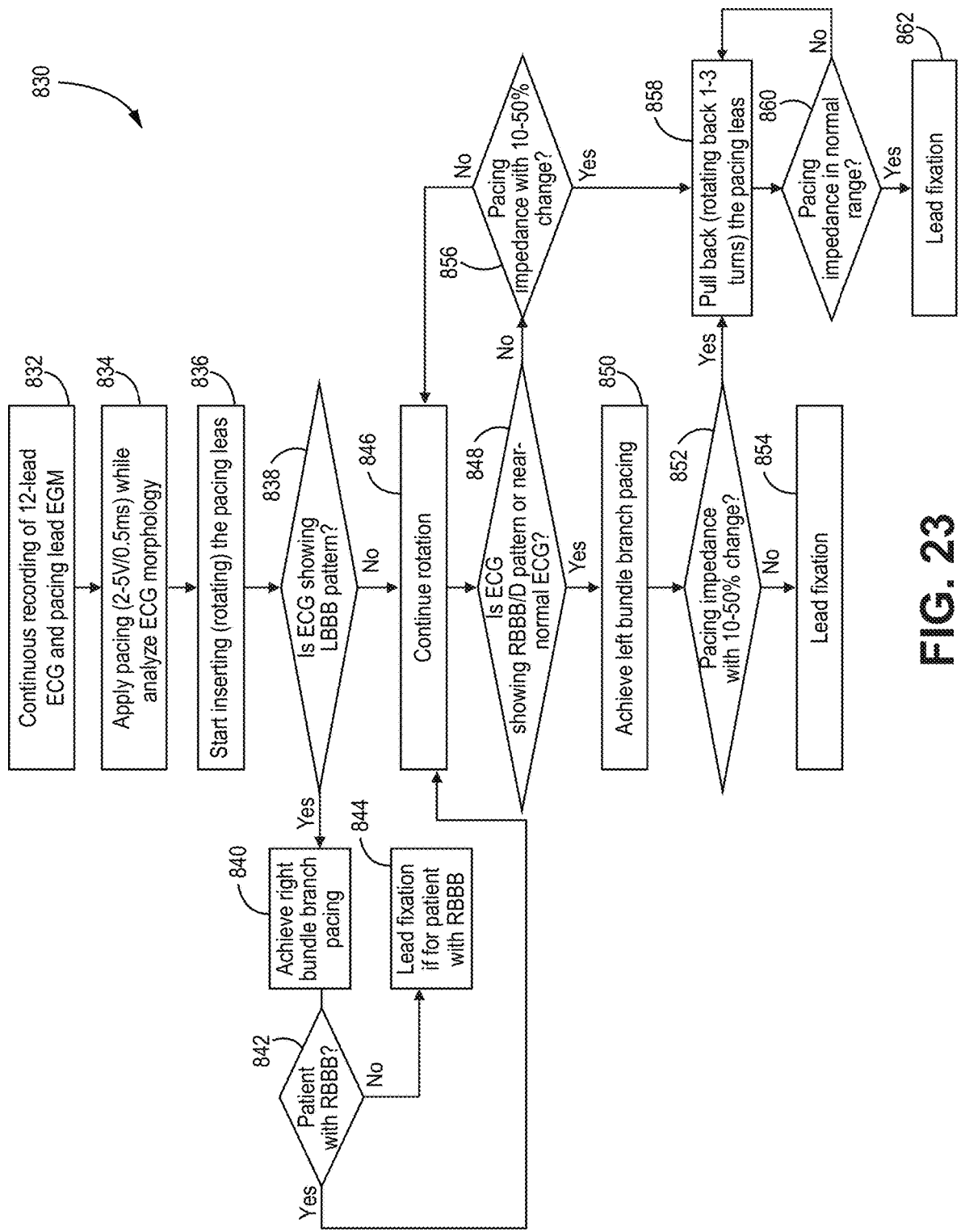

FIG. 23 is a flow diagram showing one illustrative method for implanting an IMD for His bundle or bundle branch pacing.

Figure 24:
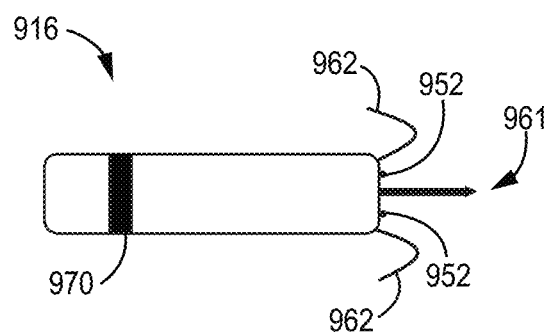

FIG. 24 schematically depicts an implantable medical device (IMD) including a first and second pacing electrodes (i.e., cathodes) near a distal end portion of the IMD and a ring electrode (i.e., anode) located at a proximal end portion of the IMD.

Figure 25:
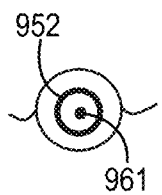
Figure 26:
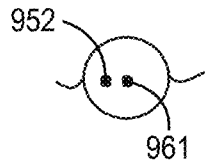
Figure 27:
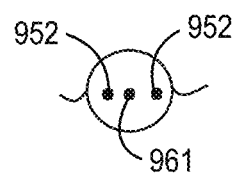

FIGS. 25-27 are end views of a distal end of various IMDs, such as the IMD of FIG. 24.

FIGS. 28A-B depict a cross-sectional view of a lead connection to an implantable medical device that shows a lead connector before and after placement in the connector.

Figure 29:
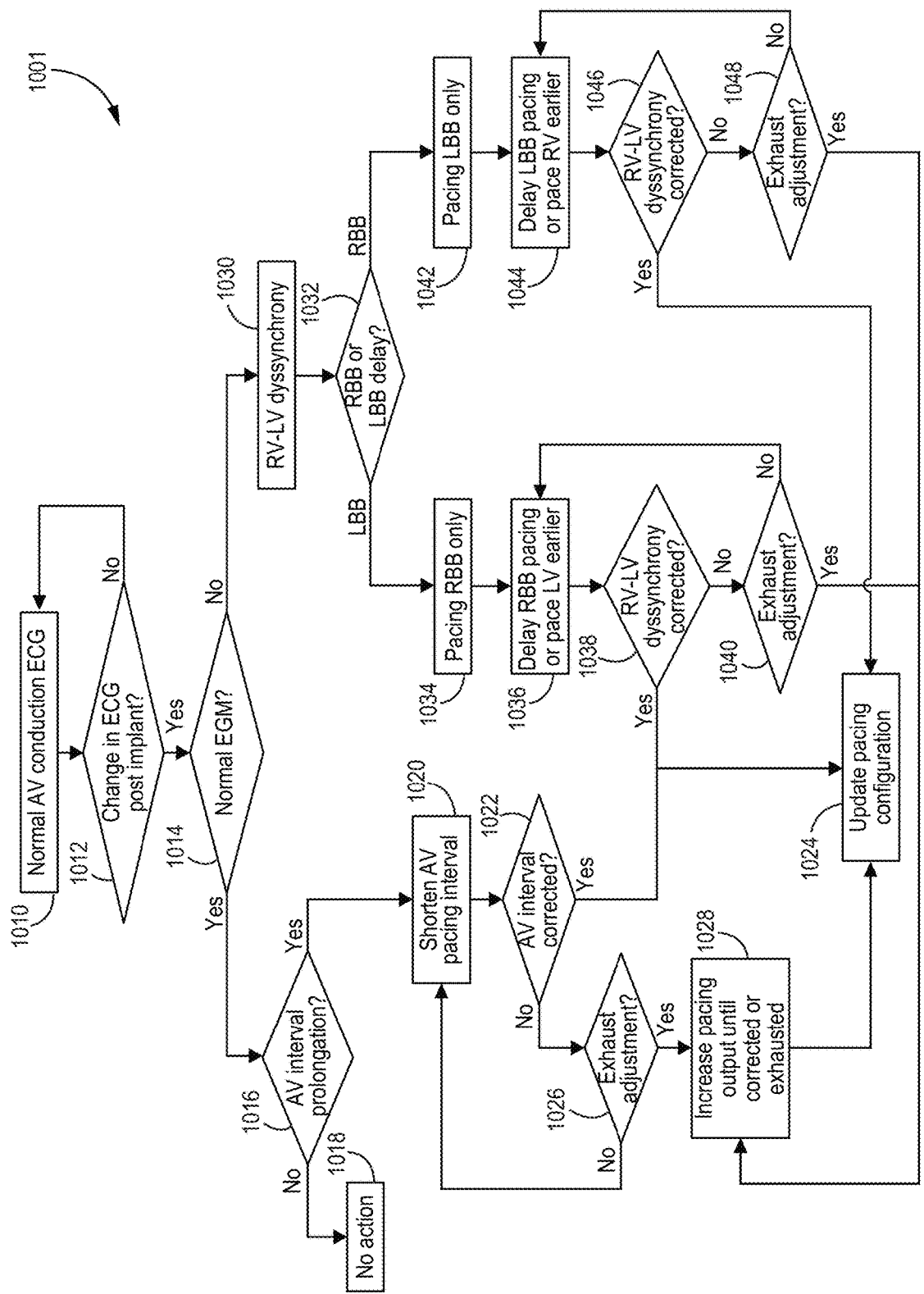

FIG. 29 is a flow diagram for a method of His bundle pacing adjustment post-implantation.

Figure 30:
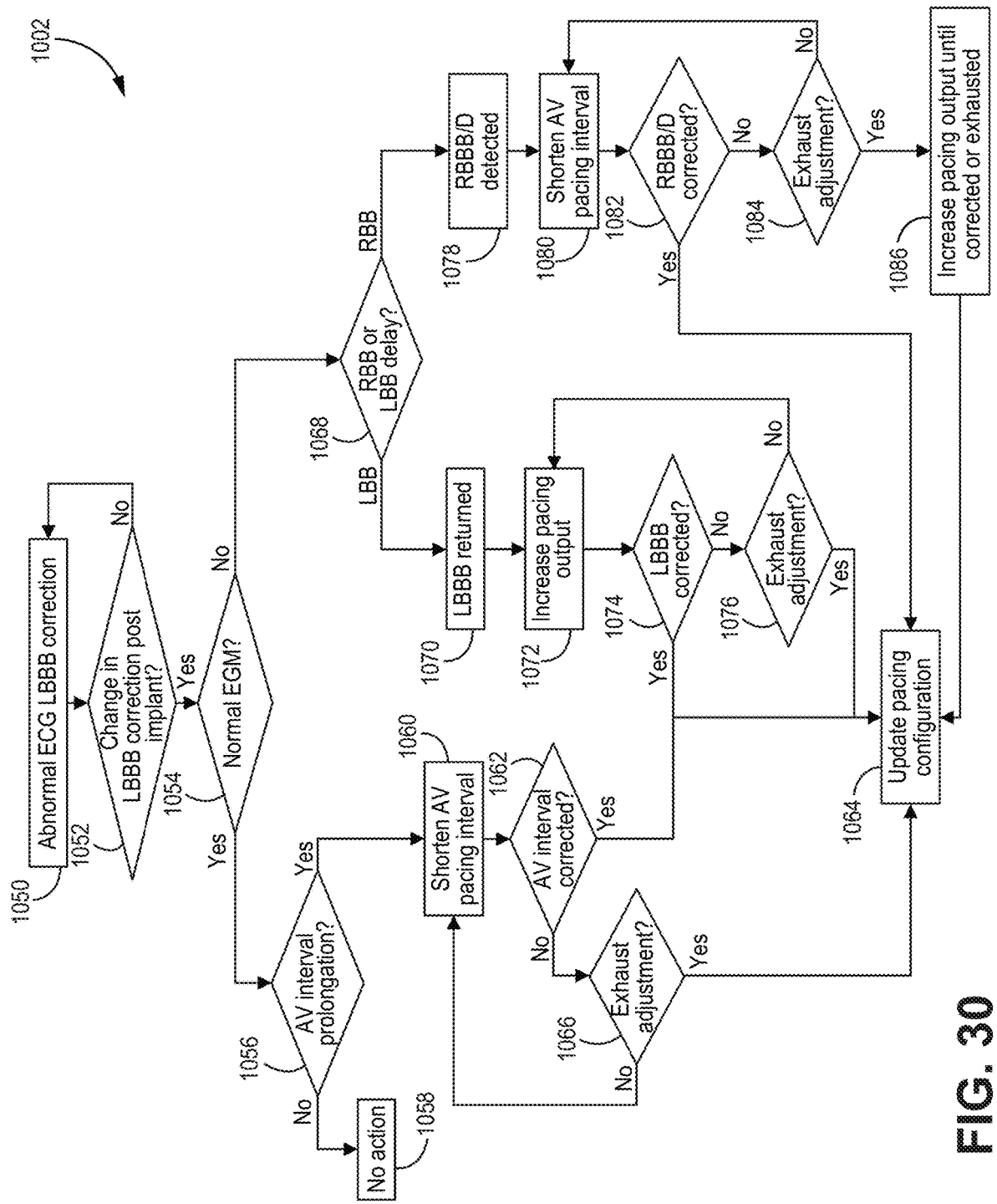

FIG. 30 is a flow diagram for a method of His bundle pacing adjustment post-implantation.

Figure 31:
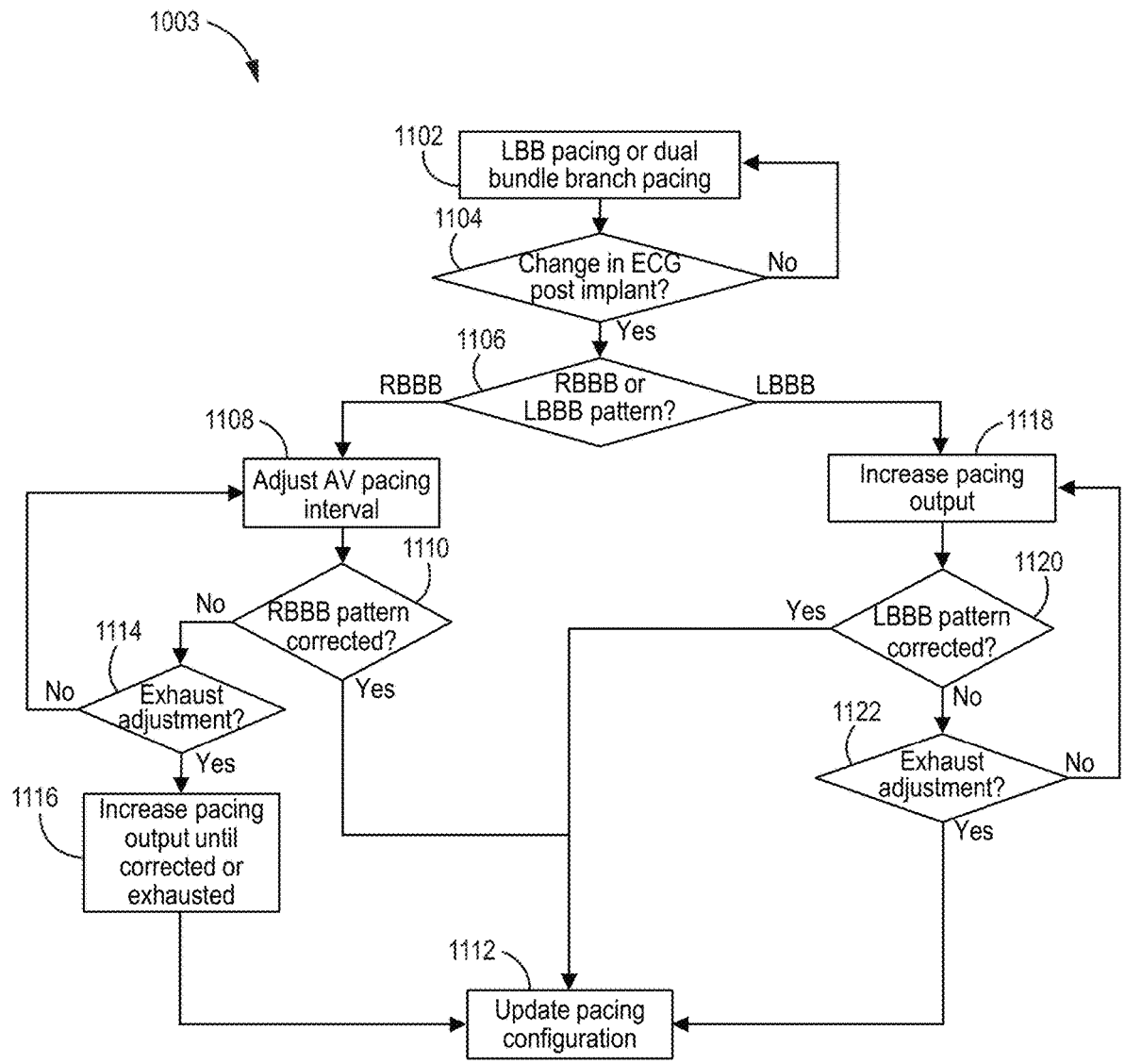

FIG. 31 is a flow diagram for a method of bundle branch pacing adjustment post-implantation.

DETAILED DESCRIPTION

Figure 2A:
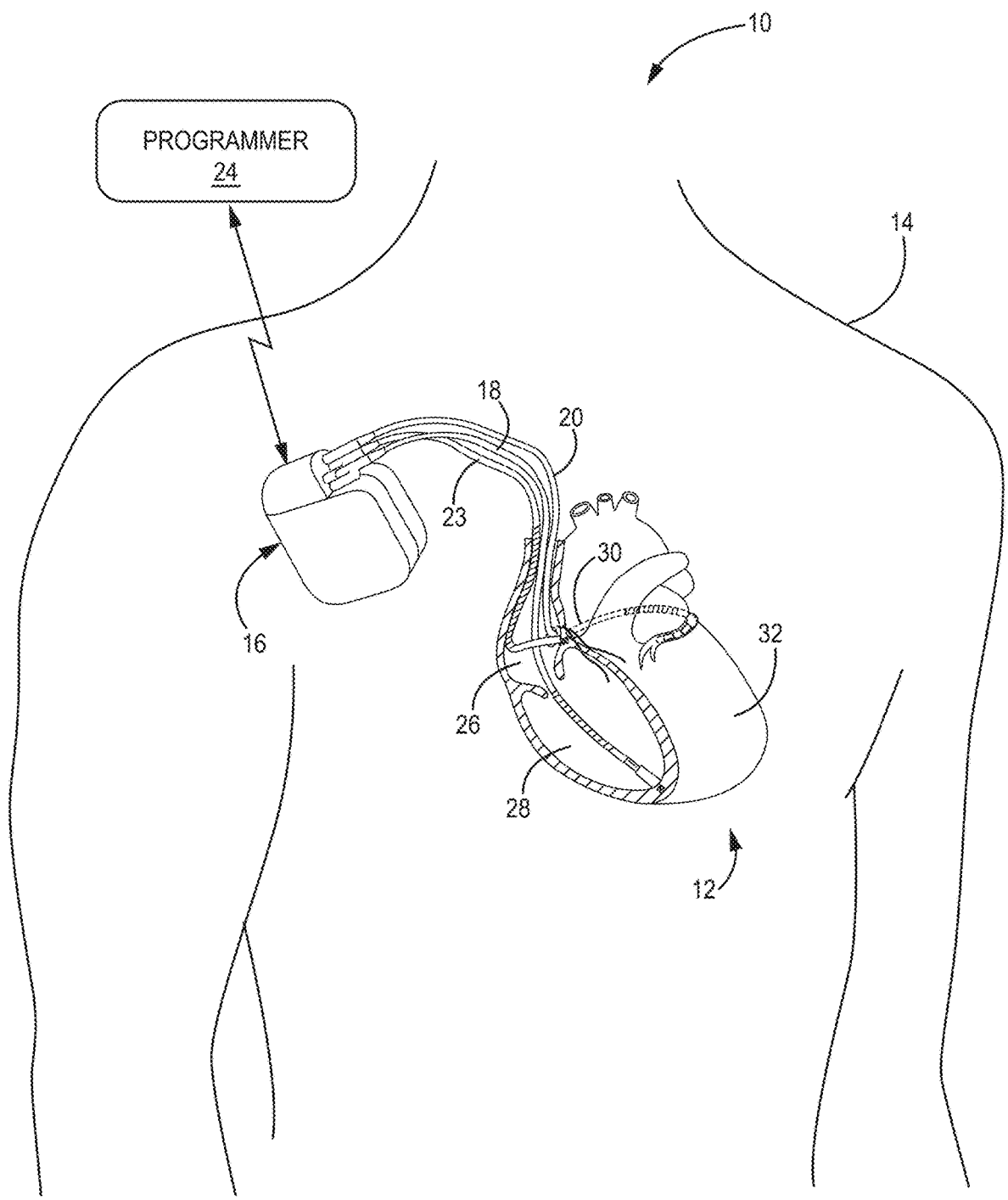
FIG. 2A is a conceptual diagram illustrating an example therapy system (e.g., triple-chamber implantable medical device) that is configured to provide therapy to a heart of patient through a His-bundle or bundle-branch pacing lead and lead placed either in the right ventricle or the right atrium using an implantable medical device (IMD).
Figure 2B:
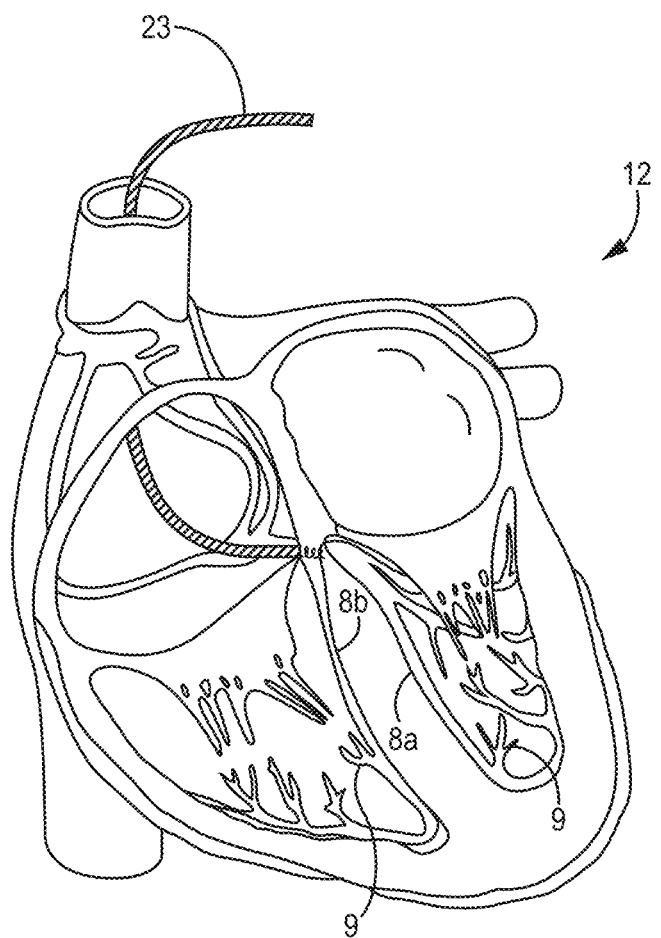
FIG. 2B is a schematic diagram illustrating an example His-bundle or bundle-branch pacing lead positioned in bundle of the His in a cross-sectional view of the heart.

FIGS. 2A-B are conceptual diagrams illustrating one example therapy system 10 that may be used to provide therapy to heart 12 of patient 14. Patient 14 ordinarily, but not necessarily, will be a human. Therapy system 10 includes IMD 16, which is coupled to leads 18, 20, 23 and programmer 24. IMD 16 may be, for example, an implantable pacemaker, cardioverter, and/or defibrillator that provides electrical signals to heart 12 via electrodes coupled to one or more of leads 18, 20, 23. Further non-limiting examples of IMD 16 include: a pacemaker with a medical lead, an implantable cardioverter-defibrillator (ICD), an intracardiac device, a leadless pacing device (LPD), a subcutaneous ICD (S-ICD), and a subcutaneous medical device (e.g., nerve stimulator, inserted monitoring device, etc.).

Leads 18, 20, 23 extend into heart 12 of patient 14 to sense electrical activity of heart 12 and/or deliver electrical stimulation to heart 12. In the example shown in FIG. 2A, right ventricular (RV) lead 18 extends through one or more veins (not shown), the superior vena cava (not shown), and right atrium (RA) 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Bundle pacing lead 23 (e.g., His-bundle or bundle-branch pacing lead) extends through one or more veins and the vena cava, and into the right atrium 26 of heart 12 to pace the His bundle or one or both bundle branches. In some embodiments, bundle pacing lead 23 may be positioned within about 1 millimeter of the His bundle or one or both bundle branches.

As used herein, the term "bundle pacing" refers to His bundle pacing, bundle branch pacing, or both His bundle pacing and bundle branch pacing. Bundle branch pacing refers to pacing one or both of the left and right bundle branches of the patient's heart 12.

As used herein, the term "activation" refers to a sensed or paced event. For example, an atrial activation may refer to an atrial sense or event (As) or an atrial pace or artifact of atrial pacing (Ap). Similarly, a ventricular activation may refer to a ventricular sense or event (Vs) or a ventricular pace or artifact of ventricular pacing (Vp), which may be described as ventricular stimulation pulses. In some embodiments, activation interval can be detected from As or Ap to Vs or Vp, as well as Vp to Vs. In particular, activation intervals may include a pacing (Ap or Vp) to ventricular interval (LV or RV sense) or an atrial-sensing (As) to ventricular-sensing interval (LV or RV sense).

One example of bundle pacing lead 23 (e.g., a His lead) can be the SELECTSURE™ 3830. A description of the SELECTSURE™ 3830 is found in the Medtronic model SELECTSURE™ 3830 manual (2013), incorporated herein by reference in its entirety. The SELECTSURE™ 3830 includes two or more conductors with or without lumens.

An elongated conductor of the lead may extend through a hermetic feedthrough assembly (not shown), and within an insulative tubular member of the lead, and may electrically couple an electrical pulse generator (contained within housing) to the helical tip of bundle pacing lead 23. The conductor may be formed by one or more electrically conductive wires, for example, MP35N alloy known to those skilled in the art, in a coiled or cabled configuration, and the insulative tubular member may be any suitable medical grade polymer, for example, polyurethane, silicone rubber, or a blend thereof. According to an illustrative embodiment, the flexible lead body extends a pre-specified length (e.g., about 10 centimeters (cm) to about 20 cm, or about 15 to 20 cm) from a proximal end of housing to the other end. The lead body is less than about 7 French (FR) but typically in the range of about 3 to 4 FR in size. In one or more embodiments, about 2 to about 3 FR size lead body is employed.

His bundle pacing can be performed by other leads. Another illustrative lead, including two or more pacing electrodes, can be used to deliver multisite pacing pulses to the bundle of His or one or both bundle branches. Multisite pacing can be delivered simultaneously or sequentially, as described and shown by U.S. Patent Publication No. 2016/0339248, filed on Apr. 21, 2016, entitled EFFICIENT DELIVERY OF MULTI-SITE PACING, the disclosure of which is incorporated by reference in its entirety.

Multi-site or multipoint pacing may be delivered by simultaneous or sequential stimulation of two or more electrodes located in the same chamber (e.g., LV). Simultaneous pacing is defined as pacing from two or more electrodes where the timing delay between electrodes is less than about 50, 30, 10, or even 5 ms. In some embodiments, the timing delay between electrodes is greater than 1 ms. In one or more embodiments, the timing delay between electrodes is about 5 ms.

Since the electrodes in multi-site or multi-point stimulation are in close proximity to each other, it may be important to detect and verify effective capture of individual electrodes during delivery of such therapy. Delivering multisite pacing pulses may include delivering pacing pulses to a first tissue site and a second tissue site through first and second pacing electrodes, respectively, all of which may occur within the same cardiac cycle.

In particular, a lead configured to perform multi-site pacing, which is different than LV coronary sinus lead 20, can be placed in the ventricular septum with the first (distal) electrode on the left side of the ventricular septum for left bundle branch pacing and with the second electrode (proximal) on the right side of the septum for pacing the right bundle branch. An interelectrode distance may be defined as the distance between the first and second electrodes, or the distance that the electrodes are apart. In some embodiments, the interelectrode distance is at least about 3, 4, 5, 6, 7, or 8 millimeters (mm). In some embodiments, the interelectrode distance is at most about 15, 14, 13, 12, 11, or 10 mm. For example, the interelectrode distance may be in a range from about 6 to 12 mm apart. Once the pacing is delivered, both the left bundle branch and the right bundle branch may be stimulated such that both ventricles are naturally or near-naturally synchronized. In contrast, in traditional CRT, the ventricles may be described as not naturally synchronized.

A single lead, including two (or more) pacing electrodes (e.g., cathodes) may deliver cathode pacing outputs at two separate locations (e.g., left and right bundle branches), so both bundle branches can be excited at the same time.

His bundle pacing, though a leading candidate for physiological pacing, may be hard to implant, may have a relatively high pacing threshold, and may have an unstable long-term pacing threshold in patients with conduction disease. Bundle branch pacing may bypass the pathological region and may have a low and stable pacing threshold. In some embodiments, only one bundle branch may be paced by using pacing leads. One aspect of this disclosure provides pacing of both bundle branches at the same time (e.g., dual bundle branch pacing), which may mimic intrinsic activation propagation via the His bundle-Purkinje conduction system, e.g., paced activation propagates via both bundle branches to both ventricles for synchronized contraction. Traditional His bundle pacing, on the other hand, typically paces the His bundle proximal to the bundle branches. In some embodiments, IMD 16 may include one, two, or more electrodes located in one or more bundle branches configured for bundle branch pacing. In some embodiments, IMD 16 may be an intracardiac pacemaker or leadless pacing device (LPD), such as LPD 616 (FIGS. 15-16).

As used herein, "leadless" refers to a device being free of a lead extending out of patient's heart 12. In other words, a leadless device may have a lead that does not extend from outside of the patient's heart to inside of the patient's heart. Some leadless devices may be introduced through a vein, but once implanted, the devices are free of, or may not include, any transvenous lead and may be configured to provide cardiac therapy without using any transvenous lead. In one or more embodiments, an LPD for bundle pacing does not use a lead to operably connect to an electrode disposed proximate to the septum when a housing of the device is positioned in the atrium. A leadless electrode may be leadlessly coupled to the housing of the medical device without using a lead between the electrode and the housing.

IMD 16 may sense electrical signals attendant to the depolarization and repolarization of heart 12 via electrodes (not shown in FIGS. 2A-B) coupled to at least one of leads 18, 20, 23. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of leads 18, 20, 23. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 (FIG. 1) may be a handheld computing device or a computer workstation or a mobile phone. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. For example, methods 300-500 shown in FIGS. 12-14 may be used to optimize pacing parameters. Through the graphical user interface on programmer 24, a user may select one or more optimized parameters. For example, methods 300-500 can optimize the AV delay and/or VV delay. The computer instructions can present the best AV delay to be used for a patient or a user may be presented with a set of optimal AV delays and the user can select one of the optimal AV delays.

In addition, the user may select which pacing criterion to use when determining whether pacing timing needs to be adjusted. As described further herein with respect to FIG. 12, block 304 in method 300 uses QRS duration to determine whether pacing timing needs to be adjusted. QRS complex involves a set of waves that occur in quick succession and is referred to as the QRS complex. In some embodiments, the QRS complex is detected using far-field electrical signals. For example, the far-field electrical signals may be sensed in a far-field electrogram (EGM) monitored by IMD 16 and a corresponding lead or a separate device, such as a subcutaneously implanted device. QRS duration is the time from which the Q wave is detected until the S wave ends. While QRS duration can be employed in any of the methods described herein, other criteria may also be used including R-wave timing, pacing-RV or -LV sensing, and/or VV delay. Any one of these criteria may be selected by, for example, processor 80 or by a user through a GUI on programmer 24.

As used herein, the term "far-field" electrical signal refers to the result of measuring cardiac activity using a sensor, or electrode, positioned outside of an area of interest. For example, an ECG signal measured from an electrode positioned outside of the patient's heart is one example of a far-field electrical signal of the patient's heart. As another example, a far-field electrical signal representing electrical activity of a chamber of the patient's heart may be measured from a sensor, or electrode, positioned in an adjacent chamber.

As used herein, the term "near-field" electrical signal refers to the result of measuring cardiac activity using a sensor, or electrode, positioned near an area of interest. For example, an EGM signal measured from an electrode positioned on the left side of the patient's ventricular septum is one example of a near-field electrical signal of the patient's LV.

R-wave timing is the time in which QRS is detected. Typically, R-wave timing includes using the maximal first derivative of an R-wave upstroke (or the time of the maximal R-wave value). R-wave timing is also used in the device marker channel to indicate the time of the R-wave or the time of ventricular activation.

Pacing-RV sensing or pacing-LV sensing (e.g., pacing-to-RV sensing or pacing-to-LV sensing) is the time interval from the pacing (or pacing artifact) to the time of RV or LV sensing. For example, if pacing-RV sensing is much longer than pacing-LV sensing, this may indicate that the LV activation is occurring much earlier than RV activation (so pacing-RV sensing is longer), then RV pacing may be delivered in synchronization with bundle pacing, so RV and LV activation can occur approximately at the same time.

A user, such as a physician, technician, or other clinician, may interact with programmer 24 to communicate with IMD 16. For example, the user may interact with programmer 24 to retrieve physiological or diagnostic information from IMD 16. One illustrative IMD 16 is described in the Medtronic AMPLIA MRITM CRT-D SURESCAN™ DTMB2D1 manual, which is incorporated by reference in its entirety. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia (tachy) episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, 23, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies (e.g., bundle pacing therapy, cardiac resynchronization therapy, anti-tachy therapy, etc.). In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 3A:
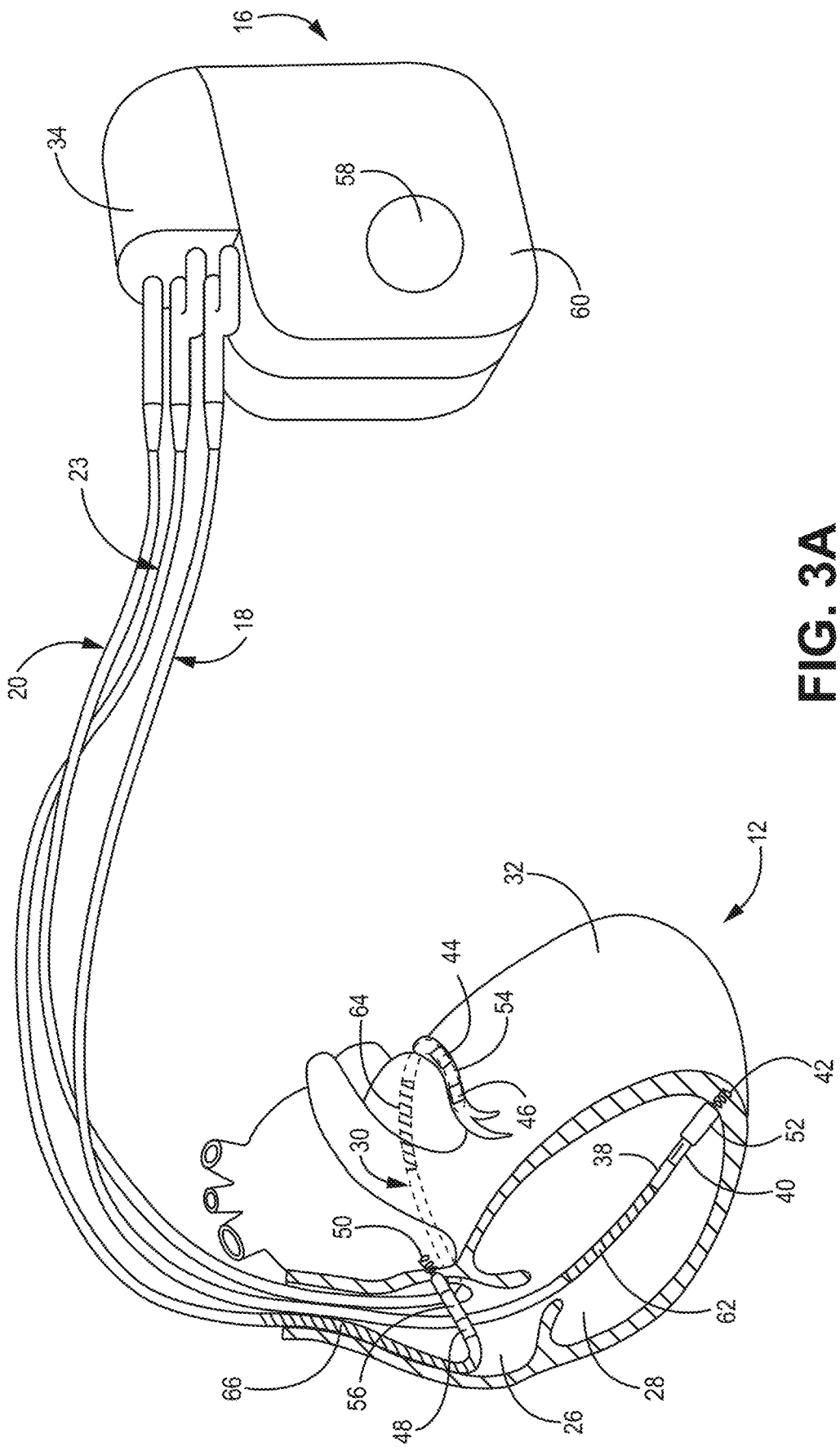
FIG. 3A is a conceptual diagram illustrating an example therapy system (e.g., dual-chamber implantable medical device) that is configured to provide therapy to a heart of patient suffering from atrial fibrillation through a His-bundle or bundle-branch pacing lead and lead placed in the left ventricle using an IMD.

FIG. 3A is a conceptual diagram illustrating IMD 16 and leads 18, 20, 23 of therapy system 10 in greater detail. The triple chamber IMD 16 may be used for cardiac rhythm therapy and defibrillation or cardioversion therapy (CRT-D). Leads 18, 20, 23 may be electrically coupled to a stimulation generator, a sensing module, or other modules of IMD 16 via connector block 34. In some examples, proximal ends of leads 18, 20, 23 may include electrical contacts that electrically couple to respective electrical contacts within connector block 34. In addition, in some examples, leads 18, 20, 23 may be mechanically coupled to connector block 34 with the aid of set screws, connection pins, or another suitable mechanical coupling mechanism.

Each of the leads 18, 20, 23 includes an elongated, insulative lead body, which may carry any number of concentric coiled conductors separated from one another by tubular, insulative sheaths. In the illustrated example, an optional pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 23. In FIG. 3A, pressure sensor 38 is disposed in right ventricle 28. Pressure sensor 38 may respond to an absolute pressure inside right ventricle 28, and may be, for example, a capacitive or piezoelectric absolute pressure sensor. In other examples, pressure sensor 38 may be positioned within other regions of heart 12 and may monitor pressure within one or more of the other regions of heart 12, or pressure sensor 38 may be positioned elsewhere within or proximate to the cardiovascular system of patient 14 to monitor cardiovascular pressure associated with mechanical contraction of the heart. Optionally, a pressure sensor in the pulmonary artery can be used that is in communication with IMD 16.

Electrodes 40, 44 and 48 may take the form of ring electrodes, and electrodes 42, 46 and 50 may take the form of extendable and/or fixed helix tip electrodes mounted within insulative electrode heads 52, 54 and 56, respectively. Each of electrodes 40, 42, 44, 46, 48 and 50 may be electrically coupled to a respective one of the coiled conductors within the lead body of its associated lead 18, 20, 23, and thereby coupled to respective ones of the electrical contacts on the proximal end of leads 18, 20 23.

Figure 3B:
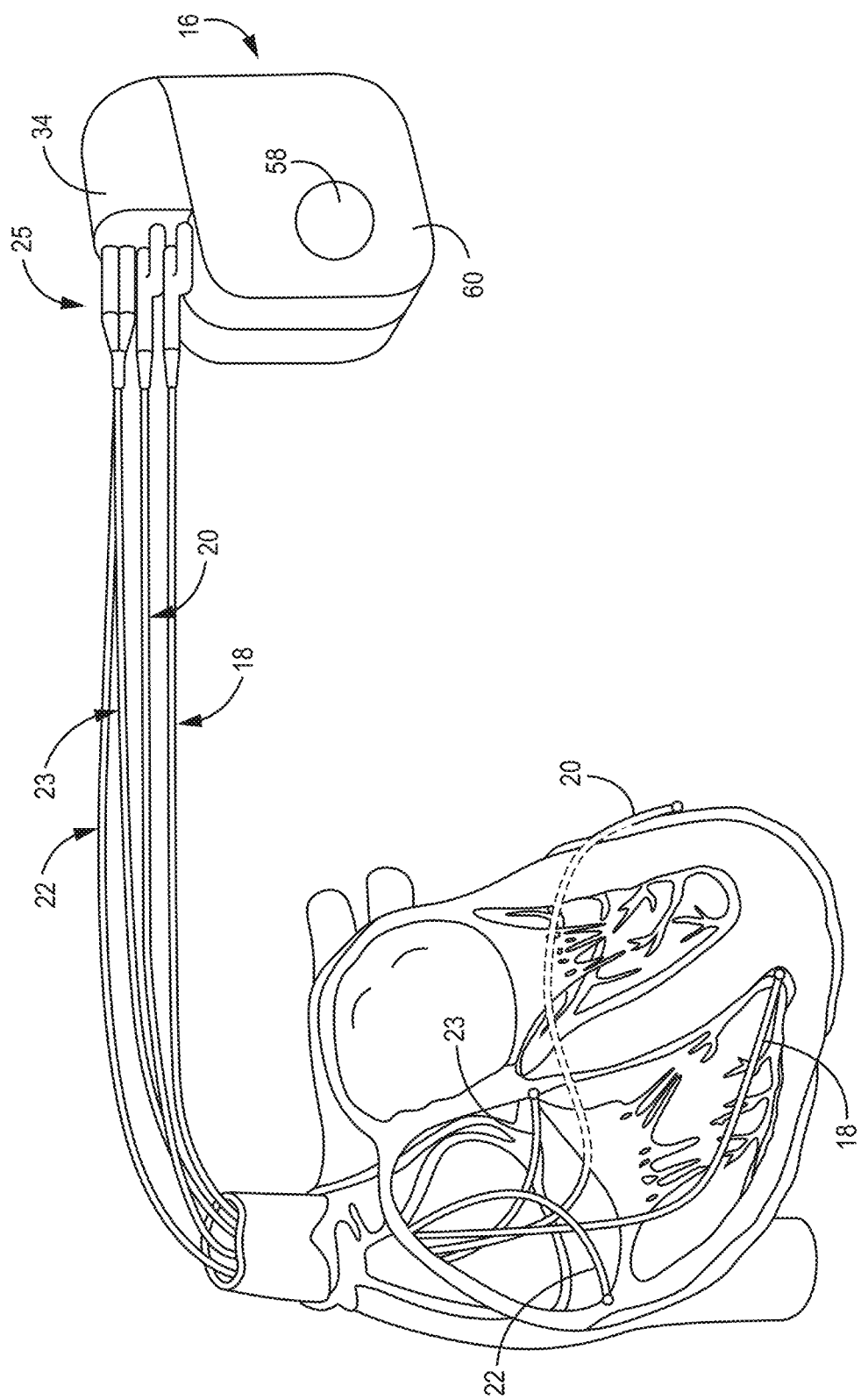
FIG. 3B is a schematic diagram illustrating an example of a His-bundle or bundle-branch pacing lead positioned in bundle of the His in a cross-sectional view of the heart using an IMD.

Electrodes 40, 42, 44, 46, 48 and 50 may sense electrical signals attendant to the depolarization and repolarization of heart 12. The electrical signals are conducted to IMD 16 via the respective leads 18, 20, 23. In some examples, IMD 16 also delivers pacing pulses via electrodes 40, 42, 44, 46, 48, 50 to cause depolarization of cardiac tissue of heart 12. In some examples, as illustrated in FIGS. 3A-B, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 may be defined by an uninsulated portion of an outward facing portion of housing 60 of IMD 16. Electrode 50 may be used for pacing and/or sensing of the His bundle or bundle branch tissue. Other divisions between insulated and uninsulated portions of housing 60 may be employed to define two or more housing electrodes. In some examples, housing electrode 58 includes substantially all of housing 60. Any of the electrodes 40, 42, 44, 46, 48 and 50 may be used for unipolar sensing or pacing in combination with housing electrode 58 or for bipolar sensing with two electrodes in the same pacing lead. In one or more embodiments, housing 60 may enclose a stimulation generator (see FIG. 5) that generates cardiac pacing pulses and defibrillation or cardioversion shocks, as well as a sensing module for monitoring the patient's heart rhythm.

Leads 18, 20, 23 may also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 3A, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 23 in other examples, or to a lead other than leads 18, 20, 23 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

FIG. 3B shows IMD 16 coupled to leads 18, 20, 22, 23. Right atrial (RA) lead 22 may extend through one or more veins and the vena cava, and into the right atrium 26 of heart 12. RA lead 22 may be connected to triple chamber IMD 16, e.g., using a Y-adaptor. IMD 16 may be used for cardiac rhythm therapy and defibrillation or cardioversion therapy (CRT-D). RA lead 22 may include electrodes that are the same or similar to the electrodes of lead 18, 20, 23, such as ring electrodes 40, 44 and 48, extendable helix tip electrodes 42, 46 and 50, and/or elongated electrodes 62, 64, 66, in the form of a coil.

The configuration of therapy system 10 illustrated in FIGS. 2A-4 are merely examples. In other examples, a therapy system may include epicardial leads and/or patch electrodes instead of or in addition to the transvenous leads 18, 20, 22 and/or bundle pacing lead 23 illustrated in FIGS. 2A-4 or other configurations shown or described herein or incorporated by reference. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, such therapy systems may include any suitable number of leads coupled to IMD 16, and each of the leads may extend to any location within or proximate to heart 12. For example, other examples of therapy systems may include three transvenous leads located as illustrated in FIGS. 2A-4, and an additional lead located within or proximate to left atrium 33 (FIG. 1). As another example, other examples of therapy systems may include a single lead that extends from IMD 16 into right atrium 26 or right ventricle 28, or two leads that extend into a respective one of right ventricle 28 and right atrium 26. An example of this type of therapy system is shown in FIGS. 3A-3B. If four leads are required for therapy delivery, an IS-1 connector may be used in conjunction with Y-adaptor 25 extending from the RA port of the connector. The Y-adaptor allows two separate leads—e.g., right atrial lead and the bundle pacing bundle lead—to extend from the two separate legs of the "Y shape" while the single leg is inserted into connector block 34 on IMD 16.

Figure 4:
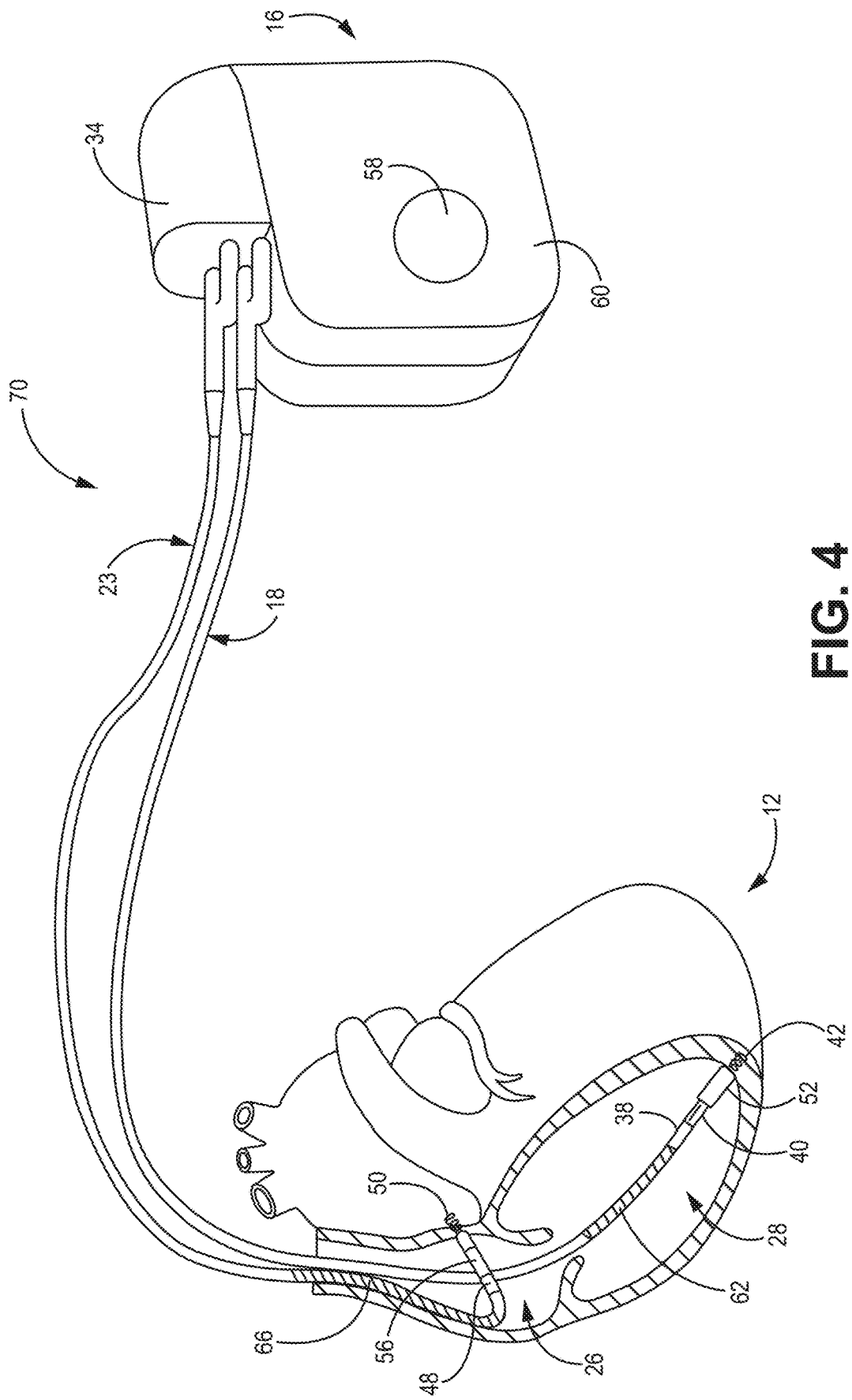
FIG. 4 is a conceptual diagram illustrating an example of a therapy system (e.g., dual chamber implantable medical device) that is configured to provide therapy to a heart of patient through a His-bundle or bundle-branch pacing lead and lead placed in the left ventricle using an IMD.

FIG. 4 is a conceptual diagram illustrating another example of therapy system 70. Therapy system 70 shown in FIG. 4 may be useful for providing defibrillation and pacing pulses to heart 12. Therapy system 70 is similar to therapy system 10 of FIGS. 2A-B or 3A-B, but includes two leads 18, 23, rather than three leads. Therapy system 70 may utilize an IMD 16 configured to deliver, or perform, dual chamber pacing. Leads 18, 23 are implanted within right ventricle 28 and right atrium 26 to pace the His bundle or one or both bundle branches, respectively.

Bundle pacing lead 23 may be in the form of a helix (also referred to as a helical electrode) may be positioned proximate to, near, adjacent to, or in the His bundle or bundle branch tissue. Bundle pacing lead 23 is configured as a bipolar lead or as a quadripolar lead that may be used with a pacemaker device, a CRT-P device or a CRT-ICD.

As illustrated in FIGS. 2A-4, lead configurations and connections of IMD 16 may vary in any suitable manner. In particular, lead configurations and connections of IMD 16 may be based on the presence of atrial fibrillation (AF) and/or the bundle branch block. If there is no AF present in the patient, bundle pacing lead 23, located in the bundle of His or one or both bundle branches (e.g., bundle of His or bundle branch region) may be connected to IMD 16 ventricular connection port and atrial lead 22 in the right atrial (RA) may be connected to the atrial connection port of the connector module. If there is persistent/chronic AF, bundle pacing lead 23 may be connected to the device atrial connection port and RV lead 18 in the right ventricle (RV) may be connected to the ventricular connection port. In an ICD, RV lead 18 may be connected to connector block 34 at RV connection port, and bundle pacing lead 23 may be connected to the atrial port connector block.

In a CRT-ICD, RV lead 18 positioned in the RV may be connected to device RV connection port. If there is no atrial fibrillation (AF), atrial lead 22 positioned in the right atrium may be connected to the atrial connection port, and bundle pacing lead 23 may be connected to the LV connection port. If there is persistent/chronic AF, bundle pacing lead 23 may be connected to the device atrial connection port, RV lead 18 may be connected to the RV connection port, and LV lead 20 in LV cardiac vein may be connected to the LV connection port.

In a CRT-P device, if there is no AF, atrial lead 22 in the right atrium may be connected to the atrial connection port, bundle pacing lead 23 may be connected to the device RV connection port, and LV lead 20 in the LV cardiac vein may be connected to the LV connection port. If there is persistent/chronic AF, bundle pacing lead 23 may be connected to the atrial connection port, RV lead 18 may be connected to the RV connection port, and LV lead 20 may be connected to the LV connection port.

In some embodiments, a right atrial port may receive RA lead 22, a left ventricular port may receive LV lead 20, and bundle pacing lead 23 is configured to be coupled to the right atrial port or ventricular port.

In some embodiments, when the patient is experiencing atrial fibrillation, bundle pacing lead 23 may be inserted through the device right atrial port, RV lead 18 may be inserted through the device right ventricular port, and LV lead 20 may be inserted through the device left ventricular port.

In some embodiments, when a patient is not experiencing atrial fibrillation, bundle pacing lead 23 may be inserted through either the right or left ventricular port of the device, and RV or LV lead 18, 20 may be inserted through the other of the right or left ventricular port of the device.

In some embodiments, the right atrial port may receive a Y-adaptor. The Y-adaptor may receive connections to the tip and ring electrodes of bundle pacing lead 23.

In some embodiments, RV lead 18 is inserted through right ventricular port of IMD 16 and LV lead 20 is inserted through the left ventricular port of IMD 16.

Figure 5:
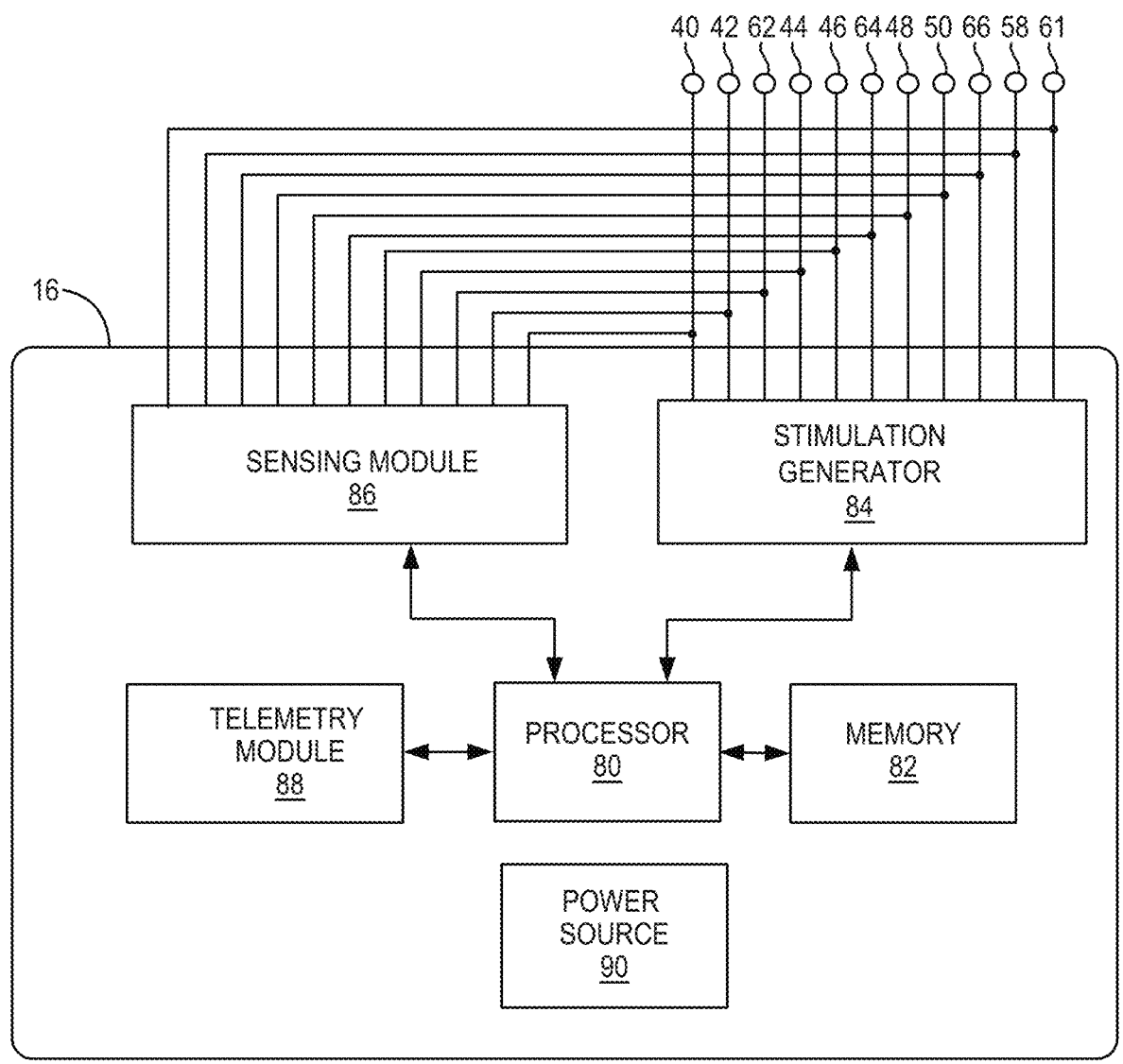
FIG. 5 is a functional block diagram illustrating an example of a configuration of an implantable medical device of FIG. 2A, 3A-4, or 15-18B.

FIG. 5 is a functional block diagram of one example configuration of IMD 16, which includes processor 80, memory 82, stimulation generator 84 (e.g., electrical pulse generator or signal generating circuit), sensing module 86 (e.g., sensing circuit), telemetry module 88, and power source 90. One or more components of IMD 16, such as processor 80, may be contained within a housing of IMD 16 (e.g., within a housing of a pacemaker). Telemetry module 88, sensing module 86, or both telemetry module 88 and sensing module 86 may be included in a communication interface. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs (e.g., optimization of the atrial-His bundle or bundle branch-ventricle delay, VV delay etc.), which may be stored in memory 82. Specifically, processor 80 may control stimulation generator 84 to deliver electrical pulses with amplitudes, pulse widths, frequency, or electrode polarities specified by the selected one or more therapy programs.

In some embodiments, RA lead 22 may be operably coupled to electrode 61, which may be used to monitor or pace the RA. Stimulation generator 84 may be electrically coupled to electrodes 40, 42, 44, 46, 48, 50, 58, 61, 62, 64, and 66, e.g., via conductors of respective lead 18, 20, 22, 23 or, in the case of housing electrode 58, via an electrical conductor disposed within housing 60 of IMD 16. Stimulation generator 84 may be configured to generate and deliver electrical stimulation therapy to heart 12. For example, stimulation generator 84 may deliver defibrillation shocks to heart 12 via at least two of electrodes 58, 62, 64, 66. Stimulation generator 84 may deliver pacing pulses via ring electrodes 40, 44, 48 coupled to leads 18, 20, 23, respectively, and/or helical electrodes 42, 46, and 50 of leads 18, 20, or 23, respectively. Bundle pacing can be delivered through lead 23 that is connected to an atrial, RV, or LV connection port of connector block 34. In some embodiments, His bundle or bundle branch therapy can be delivered through leads 18 or 23. In some examples, stimulation generator 84 delivers pacing, cardioversion, or defibrillation stimulation in the form of electrical pulses. In other examples, stimulation generator 84 may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 61, 62, 64 or 66 in order to monitor electrical activity of heart 12, e.g., via electrical signals, such as electrocardiogram (ECG) signals and/or electrograms (EGMs). Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may include an amplifier. In response to the signals from processor 80, the switch module may couple the outputs from the selected electrodes to one of the sensing channels.

In some examples, one channel of sensing module 86 may include an R-wave amplifier that receives signals from electrodes 40, 42, which are used for pacing and sensing in right ventricle 28 of heart 12. Another channel may include another R-wave amplifier that receives signals from electrodes 44, 46, which are used for pacing and sensing proximate to left ventricle 32 of heart 12. In some examples, the R-wave amplifiers may take the form of an automatic gain-controlled amplifier that provides an adjustable sensing threshold as a function of the measured R-wave amplitude of the heart rhythm.

In addition, in some examples, one channel of sensing module 86 may include a P-wave amplifier that receives signals from electrodes 48, 50, which are used for pacing and sensing in right atrium 26 of heart 12. In some examples, the P-wave amplifier may take the form of an automatic gain-controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that includes an amplifier with a relatively wider pass band than the R-wave or P-wave amplifiers or a high-resolution amplifier with relatively narrow-pass band for His bundle or bundle branch potential recording. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may include a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module may also determine the amplitude of the cardiac pacing pulses.

During pacing, escape interval counters within the pacer timing/control module may be reset upon sensing of R-waves and P-waves. Stimulation generator 84 may include pacer output circuits that are coupled, e.g., selectively by a switching module, to any combination of electrodes 40, 42, 44, 46, 48, 50, 58, 61, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode. Measurements in His-bundle- or bundle-branch-potential to R-wave interval, measurements in atrial to His-bundle- or bundle-branch-potential interval, and EGM morphology and duration can be used for (1) timing the delivery of His bundle or bundle branch pacing (e.g., bundle pacing), (2) determining the efficacy of His bundle or bundle branch pacing, and/or (3) determining the status of activation propagation such as the presence of left or right bundle branch block.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, which are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicate a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to heart 12, stimulation generator 84 may include a high voltage charge circuit and a high-voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of stimulation generator 84. Stimulation generator 84 is configured to generate electrical stimulation (e.g., pulses) to the His bundle.

Telemetry module 88 includes any suitable hardware, firmware, software or any combination thereof for communicating with another device, such as programmer 24 (FIG. 2A). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amplifier circuits within sensing module 86 to programmer 24. Programmer 24 may interrogate IMD 16 to receive the heart signals. Processor 80 may store heart signals within memory 82 and may retrieve stored heart signals from memory 82. Processor 80 may also generate and store marker codes indicative of different cardiac episodes detected by sensing module 86 and may transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 6:
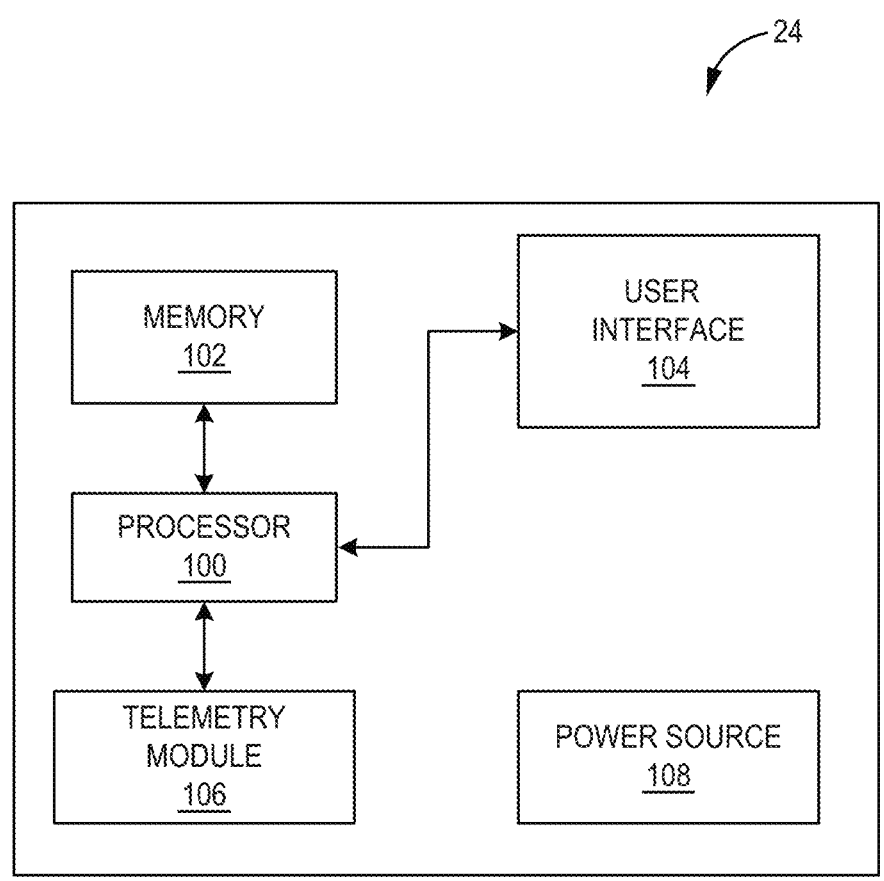
FIG. 6 is a functional block diagram illustrating an example of a configuration of a programmer used during the procedure of implanting a medical device in a patient or interrogating the implantable device during a follow-up visit at a hospital.

FIG. 6 is block diagram of illustrative programmer 24. As shown in FIG. 5, programmer 24 includes processor 100, memory 102, user interface 104, telemetry module 106 (e.g., communication interface), and power source 108. Programmer 24 may be a dedicated hardware device with dedicated software for programming of IMD 16. Alternatively, programmer 24 may be an off-the-shelf computing device running an application that enables programmer 24 to program IMD 16.

Programmer 24 may be used to select therapy programs (e.g., sets of stimulation parameters), generate new therapy programs, modify therapy programs through individual or global adjustments, and/or transmit the new programs to a medical device, such as IMD 16 (FIGS. 2A-B). A clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory portion may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication may be possible through telemetry module 106, which may be coupled to an internal antenna or an external antenna. An external antenna that is coupled to programmer 24 may correspond to the programming head that may be placed over heart 12, as described above with reference to FIGS. 2A-B. Telemetry module 106 may be similar to telemetry module 88 of IMD 16 (FIG. 5).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the IEEE 802.11 or BLUETOOTH™ specification sets, infrared communication, e.g., according to the IrDA standard, or other standard or proprietary telemetry protocols. In this manner, other external devices may be capable of communicating with programmer 24.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition, or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 5, processor 80 of IMD 16 may detect a tachyarrhythmia episode, such as a ventricular fibrillation, ventricular tachycardia, fast ventricular tachyarrhythmia episode, or an NST episode, based on electrocardiographic activity of heart 12 monitored via sensing module 86. For example, sensing module 86, with the aid of at least some of the electrodes 40, 42, 44, 46, 48, 50, 58, 61, 62, 64, and 66 (shown in FIGS. 2A-B and 3A-B), may generate one or more electrical signals, such as electrocardiogram (ECG) or electrogram (EGM) signals, that indicate the electrocardiographic activity. Alternatively, sensing module 86 may be coupled to sense electrodes that are separate from the stimulation electrodes that deliver electrical stimulation to heart 12 (shown in FIGS. 2-4) and may be coupled to one or more different leads than leads 18, 20, 22 (shown in FIGS. 2-3). The ECG or EGM signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

The distal end of the lead 18 or lead 23 may be configured to be positioned near or in the His bundle or one or both bundle branches and the IMD 16 may be configured to deliver pacing to stimulate the His bundle or one or both bundle branches during bundle pacing, via electrodes 40, 42, for example.

Figure 7:
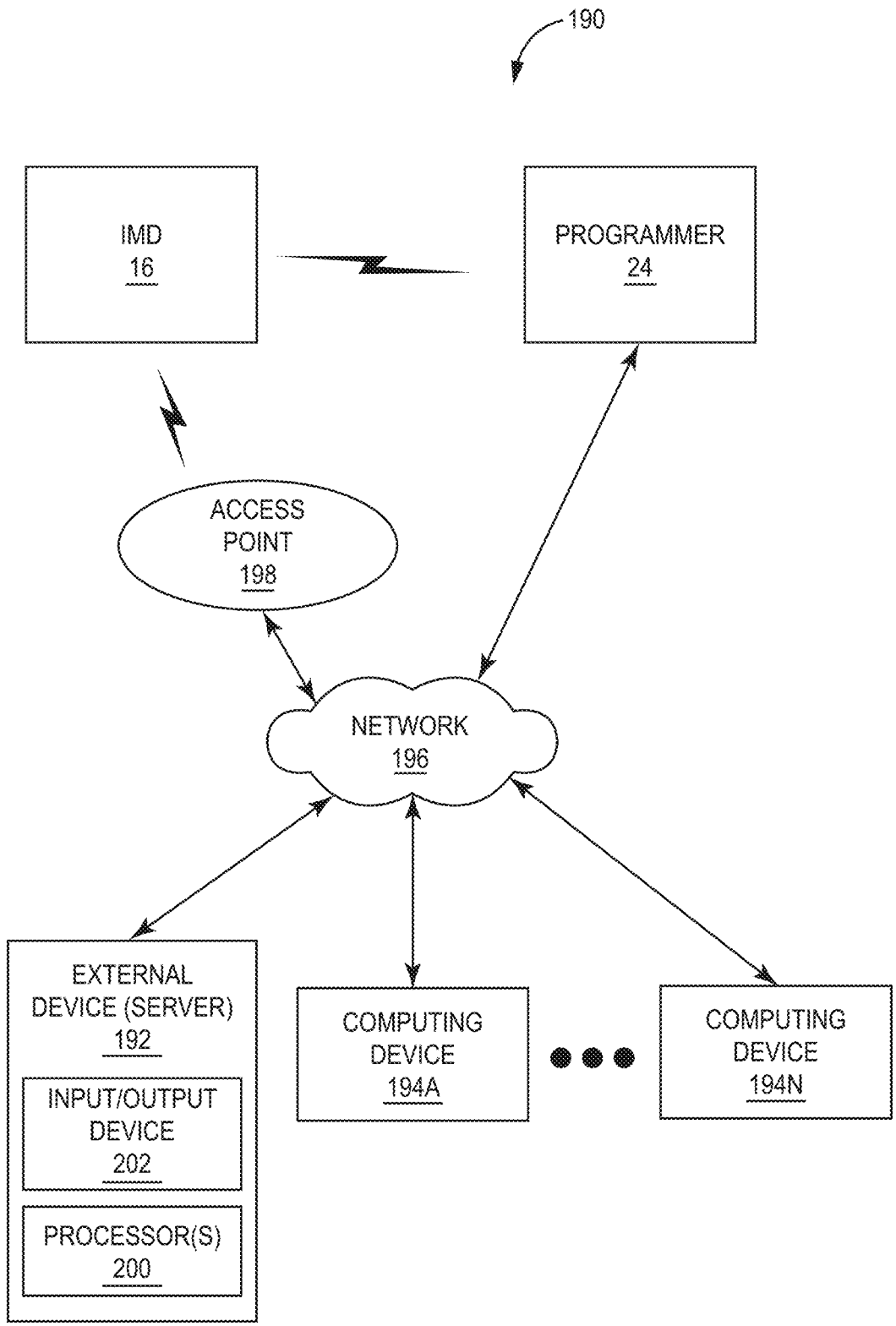
FIG. 7 is a functional block diagram illustration an example configuration of a system including a network for use with, for example, the IMD of FIG. 5.

FIG. 7 is a block diagram of illustrative system 190 that includes external device 132, such as a server, and one or more computing devices 194A-194N that are coupled to IMD 16 (see FIG. 5) and programmer 24 (see FIG. 6) via network 196, according to one embodiment. In this embodiment, IMD 16 uses telemetry module 88 to communicate with programmer 24 via a first wireless connection, and to communicate with access point 198 via a second wireless connection. In the example of FIG. 7, access point 198, programmer 24, external device 192, and computing devices 194A-194N are interconnected, and able to communicate with each other, through network 196. In some cases, one or more of access point 198, programmer 24, external device 192, and computing devices 194A-194N may be coupled to network 196 through one or more wireless connections. IMD 16, programmer 24, external device 192, and computing devices 194A-194N may each include one or more processors, such as one or more microprocessors, DSPs, ASICs, FPGAs, programmable logic circuitry, or the like, that may perform various functions and operations, such as those described herein.

Access point 198 may include a device that connects to network 196 via any of a variety of connections, such as telephone dial-up, digital subscriber line (DSL), or cable modem connections. In other examples, access point 198 may be coupled to network 196 through different forms of connections, including wired or wireless connections. In some examples, access point 198 may communicate with programmer 24 and/or IMD 16. Access point 198 may be co-located with patient 14 (e.g., within the same room or within the same site as patient 14) or may be remotely located from patient 14. For example, access point 198 may be a home monitor that is located in the patient's home or is portable for carrying with patient 14.

During operation, IMD 16 may collect, measure, and store various forms of diagnostic data. In certain cases, IMD 16 may directly analyze collected diagnostic data and generate any corresponding reports or alerts. In some cases, however, IMD 16 may send diagnostic data to programmer 24, access point 198, and/or external device 192, either wirelessly or via access point 198 and network 196, for remote processing and analysis.

In some cases, IMD 16 and/or programmer 24 may combine all the diagnostic data into a single displayable lead integrity report, which may be displayed on programmer 24. The lead integrity report contains diagnostic information concerning one or more electrode leads that are coupled to IMD 16, such as leads 18, 20, 22 or 23. A clinician or other trained professional may review and/or annotate the lead integrity report, and possibly identify any lead-related conditions.

In another example, IMD 16 may provide external device 192 with collected diagnostic data via access point 198 and network 196. External device 192 includes one or more processors 200. In some cases, external device 192 may request such data, and in some cases, IMD 16 may automatically or periodically provide such data to external device 192. Upon receipt of the diagnostic data via input/output device 202, external device 192 is capable of analyzing the data and generating reports or alerts upon determination that there may be a possible condition with one or more of leads 18, 20, 22, 23. For example, one or more of leads 18, 20, 22, 23 may experience a condition related to a lead fracture or an insulation breach.

In one embodiment, external device 192 may combine the diagnostic data into a lead integrity report. One or more of computing devices 194A-194N may access the report through network 196 and display the report to users of computing devices 194A-194N. In some cases, external device 192 may automatically send the report via input/output device 202 to one or more of computing devices 194A-194N as an alert, such as an audio or visual alert. In some cases, external device 192 may send the report to another device, such as programmer 24, either automatically or upon request. In some cases, external device 192 may display the report to a user via input/output device 202.

In one embodiment, external device 192 may include a secure storage site for diagnostic information that has been collected from IMD 16 and/or programmer 24. In this embodiment, network 196 may include an Internet network, and trained professionals, such as clinicians, may use computing devices 194A-194N to securely access stored diagnostic data on external device 192. For example, the trained professionals may need to enter usernames and passwords to access the stored information on external device 192. In one embodiment, external device 192 may be a CARELINK™ server provided by Medtronic, Inc., of Minneapolis, Minnesota.

FIGS. 8A-8D are schematic diagrams of mechanisms of left bundle branch block correction using bundle pacing. FIGS. 9-11 graphically depict ECG signals associated with each mechanism of LBBB/RBBB that is associated FIGS. 8A-8D.

Figure 8A:
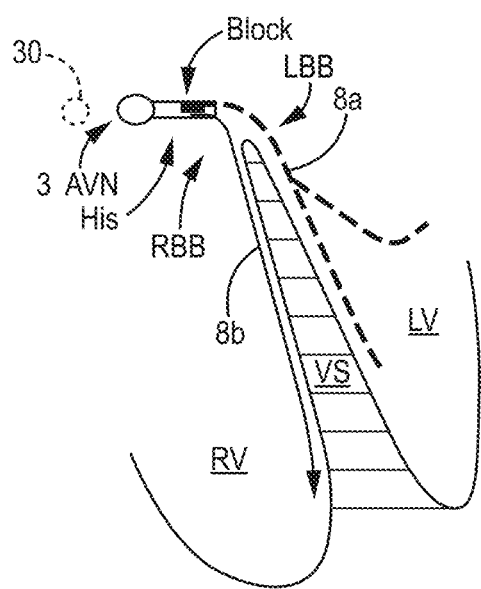
FIG. 8A depicts the His bundle and left and right bundle branches in which intrinsic rhythm (also referred to as native rhythm) is acquired from a set of electrodes without His bundle pacing being delivered.

FIGS. 8A-8D show a block near AV node 3, and right and left bundle branches 8a, 8b extending through the left and right ventricles. FIG. 8A is a schematic diagram of an incident of left bundle branch block (LBBB) that occurs during an intrinsic rhythm when no pacing is applied. Illustrative intrinsic rhythm is graphically shown in FIG. 9A where the right bundle branch 8b is not blocked.

Figure 8B:
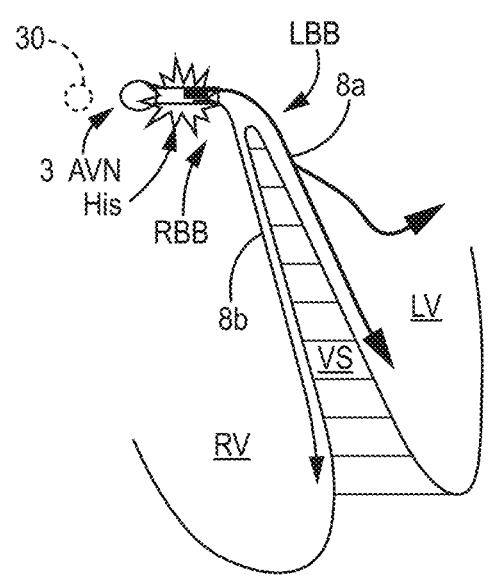
FIG. 8B depicts proximal His bundle pacing being delivered proximal to the block.

FIG. 8B is a schematic diagram of LBBB correction by proximal His bundle pacing. Proximal His bundle pacing involves delivery of electrical stimuli at a position proximal to the block as opposed to delivering pacing stimuli distal to the block. As shown in this example, the proximal position of the block is closer to AV node 3 while the distal end of the block is further away from AV node 3 and closer to the ventricles. Pacing at the proximal His bundle initiates His bundle pacing without correction of LBBB, which may be similar to traditional His bundle pacing. FIG. 9B graphically depicts the rhythm acquired during bundle pacing at a proximal His bundle that appears to be more effective as compared to the intrinsic rhythm (native conduction) graphically shown in FIG. 9A. As shown, LBBB is still present during the intrinsic rhythm (FIG. 9A) or during bundle pacing at proximal His bundle (FIG. 9B). Once the pacing output is significantly increased (FIG. 9C), bundle pacing can reach the left bundle branch and correct left bundle branch block. In one example, bundle pacing output increasing to 2.5 V from 0.5 V may allow the current, or simulation, to reach the whole area to correct for LBBB.

Figure 8C:
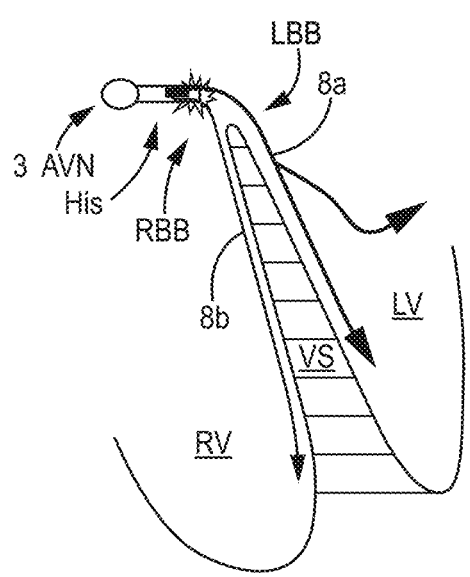
FIG. 8C depicts distal His bundle pacing being delivered distal to the block.

FIG. 8C is a schematic diagram of correction of left bundle branch block using distal His bundle pacing, which locates pacing in a distal portion of the His bundle, for example, distal to a His bundle block. FIG. 10A graphically depicts the intrinsic rhythm when LBBB is present and pacing has not yet begun to be delivered to the His bundle. FIG. 10B graphically depicts distal His bundle pacing at low pacing output. Pacing at distal His bundle captures fibers that may conduct through both left and right bundle branches and may facilitate left bundle branch block correction at a low pacing capture output.

His-bundle or bundle-branch pacing, which may utilize the natural His bundle-Purkinje conduction system, may provide optimal physiological pacing and synchronized ventricular contraction. However, bundle pacing lead 23 implantation may change conduction properties of the His bundle, which may be manifest as conduction block, including either complete or bundle branch block. Additionally, when His bundle pacing is used for correction of bundle branch block (either LBBB or RBBB), it usually requires a large pacing output because the pacing lead may be placed in the proximal His bundle (or proximal block region, see FIG. 8B). In order to achieve a low and stable pacing output for correcting bundle branch block, bundle pacing lead 23 may be placed in the distal His bundle (FIG. 8C) or even in the bundle branch (FIG. 8D).

Figure 8D:
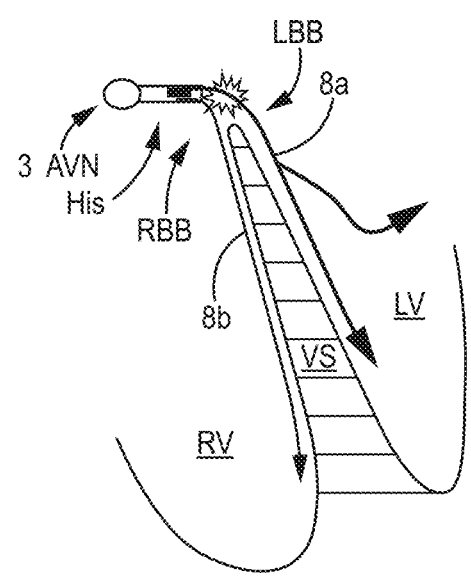
FIG. 8D depicts low output bundle pacing being delivered to the left bundle branch to correct left bundle branch block (LBBB) and/or right bundle branch block (RBBB).

FIG. 8D is a schematic diagram of correction of left bundle branch block using left bundle branch pacing. FIG. 11A graphically depicts the intrinsic rhythm when LBBB is present and pacing has not yet begun to be delivered to the left bundle branch (LBB). Low-output pacing at left bundle branch (or fibers destined for left bundle branch) may correct left bundle branch block with a trait of right bundle branch block. By adjusting atrial to His-bundle or bundle-branch pacing delay, right bundle branch block can be corrected. The atrial to His-bundle or bundle-branch pacing delay may be defined as the time when an electrical impulse, which may represent depolarization or contraction, is sensed or detected from the atrium and the time in which the pacing pulse is generated from the pulse generator. As shown in FIG. 11B in which an AV delay of 40 ms was employed, LBBB is not present but RBBB remains. Increasing the pacing AV delay interval from 40 ms to 100 ms, as shown in FIG. 11C, neither LBBB or RBBB are present.

Thus, while His bundle pacing may be optimal, sometimes undesired effects may be manifested due to bundle pacing lead implantation or pre-existing situations. By adjusting timing of delivering His-bundle or bundle-branch pacing, the present disclosure may re-synchronize His-bundle or bundle-branch pacing with activation from the atrium (pacing or intrinsic) in order to achieve synchronized ventricular activation via both left and right bundle branches and hence contraction, thereby improving pacing therapy. In the event of complete AV block, one bundle branch pacing can be synchronized with the pacing on the other ventricular chamber, for example, if pacing at the left bundle branch, it can be synchronized with the pacing in the right ventricle to avoid right bundle branch block or vice versa. In some embodiments, the bundle pacing lead may be placed in the left bundle branch to stimulate only the left bundle branch, while at the same time the pacing may be synchronized with intrinsic conduction to the RV, with the RV pacing (e.g., intrinsic or paced RV activation) or with the right bundle branch delay.

The illustrative methods disclosed herein automatically adjust delivery of bundle pacing in a cardiac pacing system to achieve synchronized ventricular activation via both left and right bundle branches and/or correction of right or left bundle branch block. Each method 300-500 (FIGS. 12-14) disclosed herein can be automatically performed in an entirely closed-loop therapy system 10. There are many different therapy system embodiments that can deliver His-bundle or bundle-branch pacing in accordance with the methods described herein. For example, IMD 16 can be a dual chamber pacemaker that can be used if atrial fibrillation (AF) is not present or not detected by processor 80. Bundle pacing lead 23 can be connected to ventricular (RV) connection port of connector block 34 of the dual chamber pacemaker. Bundle pacing lead 23 can be properly positioned in His bundle or bundle branch region. In one or more other embodiments, if persistent or chronic AF is detected by processor 80, bundle pacing lead 23 can be connected to the device atrial connection port while RV lead 18 in the RV can be connected to ventricular connection port of connector block 34 of IMD 16. Bundle pacing lead 23 may be placed in the His bundle region or bundle branch region.

In one or more other embodiments, therapy system 10 includes IMD 16 such as an ICD with a RV lead, and a bundle pacing lead extending therefrom. The RV lead may be positioned in the RV as is known to one having ordinary skill in the art or shown herein. The RV lead may be connected to the RV connection port of connector block 34 for IMD 16. The RV shock lead is generally kept in RV. The bundle branch lead may be connected to the atrial port of connector block 34 for IMD 16. Bundle branch lead 23 may then be placed in the His bundle region or bundle branch region. In one or more embodiments, the bundle branch region includes the bundle branch and a volume within 1 mm from the bundle branch.

In one or more other embodiments, a therapy system 10 includes IMD 16 (e.g., CRT-ICD etc.), a bundle pacing lead, and an RV lead. The RV lead is connected to the device RV connection port of connector block 34. The RV lead is positioned in the RV. The RV lead is connected with atrial connection port of connector block 34. In the case of CRT-ICD, RV lead (the shocking lead) is always connected to the device RV connection port, and the bundle pacing lead can be connected to the atrial port if there is persistent/chronic AF or to the LV port if there is a sinus rhythm. If no AF is present in the patient, the lead configuration may include the atrial lead being positioned in the right atrium, and the bundle pacing lead connected with LV connection port of connector block 34. If persistent or chronic AF is detected, the lead configuration may include the bundle pacing lead connected to the device atrial connection port, the RV lead connected to the RV connection port, and the LV lead connected to LV connection port of connector block 34.

In one or more other embodiments, therapy system 10 includes IMD 16, such as a CRT-P, an atrial lead, and a bundle pacing lead. If AF is not present, the lead configuration may include the atrial lead being connected to the atrial connection port. The atrial lead is positioned in the right atrium. The bundle pacing lead may be connected to the device RV connection port in some embodiments. The LV lead, connected to LV connection port, is positioned in the LV cardiac vein.

If persistent or chronic AF is present, IMD 16 lead configuration may include the bundle pacing lead being connected to the atrial connection port, the RV lead being connected to RV connection port, and the LV lead being connected to LV connection port of connector block 34 of IMD 16.

In one or more embodiments, a VVI (e.g., single chamber) pacemaker can be configured with a single bundle pacing lead (e.g., His bundle lead or bundle branch pacing lead) that is connected to the RV connection port. For example, using IMD 16 configured for VVI pacing (e.g., single chamber device), there may be only one connection port, either for atrial pacing or RV pacing in a known way. For bundle pacing, the bundle pacing lead (the only lead) is connected to the only device connection port. If the bundle pacing lead is located in the His bundle, in one or both bundle branches, or is proximate thereto, the bundle pacing lead can sense atrial electrical activity, and bundle pacing can be delivered with an approximated A to bundle-pacing delay (e.g., about 50-80 ms after atrial sensing). Such a case can happen in patients with atrioventricular block.

In another embodiment, a subcutaneous device (SD) could send a control signal to an IMD, such as a leadless pacing device (LPD) (e.g., system 610 of FIG. 15), to initiate bundle pacing. For example, the LPD may be configured to deliver His-bundle or bundle-branch pacing pulses in response to signals received from the SD. The signals may represent timing for delivering pacing pulses, such as an atrial-activation to bundle-pacing interval.

The LPD could sense a cardiac signal (e.g., an electrical signal) from the heart of the patient. Based on the cardiac signal, the LPD could determine whether to deliver bundle pacing to the heart from the LPD and at what timing interval. For example, the LPD, based on the second electrical signal, could determine that bundle pacing is not necessary and terminate bundle pacing. The LPD could consider whether sensed data meets a pre-specified threshold. For instance, if the QRS width does not exceed about 120 ms, the LPD may withhold the delivery of bundle pacing therapy (e.g., the LPD could then signal the SD that bundle pacing should not be delivered based upon the cardiac signal. The SD can be configured to perform a more detailed analysis in which at least one or more parameters (such as at least two parameters) are evaluated. The SD could then send another command signal that confirms, denies, or overrides the LPD.

In another embodiment, the LPD could sense a cardiac signal that indicates a switch between one pacing mode to another pacing mode should occur and would signal the SD. The SD could be configured to send an override signal to the LPD unless certain conditions are met.

In another embodiment, the SD transmits a control signal to the LPD to initiate bundle pacing. The LPD senses a cardiac signal (e.g., an electrical signal) from the heart of the patient. Based on the cardiac signal, the LPD could determine whether to deliver bundle pacing or the type of bundle pacing to deliver to the heart from the LPD. In one or more embodiments, the LPD, based on the second electrical signal, could initially determine that bundle pacing is not necessary. The initial determination by the LPD could be made by using tests having thresholds of one or more parameters. In one or more embodiments, the SD could perform a more detailed analysis as to whether bundle pacing should be delivered and when to be delivered. Using the sensed data from the LPD and/or SD, the SD could generate another signal to the LPD that either confirms, denies or overrides the LPDs initial determination.

In yet another embodiment, the LPD could determine that bundle pacing should be used in contravention to the SD communication. In one embodiment, the LPD would deliver bundle pacing. In one or more other embodiments, the LPD could determine that bundle pacing should be used over other pacing modes in contravention to the SD communication. In this scenario, the LPD could deliver bundle pacing.

In yet another embodiment, the LPD alone delivers bundle pacing without any communication with a SD. The LPD includes the computer instructions that employs any of the methods (e.g., FIGS. 12-14) disclosed herein. The LPD includes a pair of electrodes that senses heart activity to determine when the pacing electrode should pace the His bundle or bundle branch tissue. The LPD can also communicate with one or more sensing electrodes in the RA such that an amplifier is used to amplify the sensed signals from the sensing electrodes. The sensing electrodes are associated with an implantable device.

In yet another embodiment, the LPD can be further configured to receive a signal from one or more subcutaneous electrodes in a heart chamber. The signal from the subcutaneous electrodes can be amplified by an amplifier located in a subcutaneous device. In one embodiment, the amplifier is configured to be up to 2 times larger than existing amplifiers, such as the amplifier located in Boston Scientific's Emblem S-ICD device. In one embodiment, the amplifier is configured to be up to 1.75 times larger than the amplifier located in Boston Scientific's Emblem S-ICD device. In one embodiment, the amplifier is configured to be up to 1.5 times larger than the amplifier located in Boston Scientific's Emblem S-ICD device. In one embodiment, the amplifier is configured to be up to 1.25 times larger than the amplifier located in Boston Scientific's Emblem S-ICD device. Boston Scientific User's Manual EMBLEM S-ICD EMBLEM MRI S-ICD SUBCUTANEOUS IMPLANTABLE DEFIBRILATOR REF A209, A219, located on Boston Scientific's website is incorporated by reference in its entirety herein and can be modified to employ methods 300-500. For example, the SD may be used to sense far-field electrical signals (such as ECG) to determine QRS duration, or QRSd and an atrial signal, particularly when the LPD cannot sense such far-field electrical signals. Based on QRS timing, QRS duration, and atrial timing, the SD can communicate to the LPD a time to deliver His-bundle or bundle-branch pacing at an appropriate atrial-bundle pacing interval.

In some embodiments, the SD may be configured to deliver electrical pulses to cardiac tissue. The electrical pulses may be related to a different therapy than the therapy provided by the LPD. For example, the SD may deliver electrical pulses for cardiac resynchronization therapy.

In some embodiments, the SD may be employed to sense electrical signals from the patient's heart to determining the timings of atrial and/or ventricular activations.

The process flow diagram of FIG. 12 illustrates an illustrative method that can be performed by IMD 16. Illustrative implantable medical devices that can optimize pacing parameters such as A-bundle pacing delay include pacemakers, implantable cardioverter defibrillators, leadless pacemakers (e.g., MICRA™), leadless pacemakers in communication with a subcutaneous device shown in FIGS. 15-17 and described in the accompanying text. Medtronic MICRA™ MC1VR01 MR Conditional single chamber transcatheter pacing system with SureScanA™ technology (VVIR) manual is incorporated herein by reference in its entirety. As described in FIG. 12, bundle pacing may be delivered in synchronization with intrinsic activation or paced activation. In the example of FIG. 12, the right atrial lead may be positioned in the right atrium, the bundle pacing lead may be positioned in the His bundle region or in the bundle branch region, which may be in, or in proximity to, the left bundle branch and/or the right bundle branch. The RV lead may be positioned within the right ventricle.

Method 300 begins at block 302 in which heart activity is acquired by IMD 16 via sensing module 86 receiving signals from electrode(s) located in or near the His bundle or one or both bundle branches and/or other electrodes located in any of the other embodiments shown in FIGS. 2-4 and 15-17, or otherwise incorporated by reference.

The sensed data may be stored into memory 82 of the IMD 16. Sensed heart activity may be used to determine, or may include, one or more of: an intraventricular interval, a QRS duration, a QRS morphology, a QRS vector, an R-wave timing, a bundle-pacing to left- or right-ventricular-activation interval, and an atrial-sensing to left- or right-ventricular-activation interval. Examples of information acquired from sensed data (e.g., EGMs) include QRS duration, QRS morphology, R-wave timing, pacing-RV or -LV sensing, and/or VV interval. Pacing-RV or -LV sensing means the time interval from bundle pacing to the RV- or LV-sensing. Bundle pacing may synchronize both right and left ventricles, e.g., bundle-pacing to RV-sensing interval and bundle-pacing to LV-sensing interval are almost equal (e.g., meaning both ventricles are activated at almost same time, synchronized at the same time or with a delay).

The QRS complex is the combination of three deflections or QRS waves. The Q, R, and S waves occur in rapid succession and reflect a single event and are usually considered together. A Q wave is any downward deflection after the P wave. An R-wave follows as an upward deflection, and the S wave is any downward deflection after the R-wave. The QRS duration is measured when the Q wave is first detected until the end of the S wave. QRS morphology may be used to determine RV or LV activation time.

At decision block 304, the processor 80 of the IMD 16 may use the data, acquired from the sensed heart activity (e.g., recording of EGMs, etc.) in block 302, to determine whether one or more pacing parameters should be adjusted, such as bundle pacing timing. For example, processor 80 can determine whether QRS parameter or activation interval is greater than or equal to a threshold (e.g., 120 ms). Examples of QRS parameters or activation intervals may include, but are not limited to QRS duration, AV interval, VV interval, QRS morphology, etc. VV (V to V) interval may be representative of ventricular synchrony. When the heart rate changes, atrioventricular conduction time may change, and bundle pacing time may be adjusted with a new appropriate AV delay. Another determination can be made as to whether QRS duration is less than a threshold, such as about 120 ms. By including two different conditions that check whether QRS duration is greater than or equal to the threshold and another condition of checking whether QRS duration is less than the same or different threshold, the logic of the flow diagram causes the AV delay to converge to an optimal AV delay by gradually adjusting the AV delay until a certain number of times are looped through the flow diagram.

If processor 80 determines that one or more pacing parameters do not need to be adjusted, the NO path from block 304 to block 302 may return to continue sensing heart activity. In addition, the NO path may continue to allow bundle pacing to be delivered without requiring adjustment of pacing parameter(s). In contrast, if processor 80 of IMD 16 determines that one or more pacing parameters should be adjusted, then the YES path may continue to decision block 306 to determine whether the pacing stimuli (e.g., pulses) should be delivered earlier or later than the pacing stimuli that IMD 16 is currently set to deliver. One illustrative evaluation that can be performed by processor 80 is whether a bundle-pacing to ventricular-activation (e.g., V sensing) interval is less than a second threshold (e.g., 80 ms). In some embodiments, if the bundle pacing to ventricular activation interval is less than the second threshold, then the pacing stimuli may be delivered later, or otherwise, the pacing stimuli may be delivered earlier.

If processor 80 determines that the pacing stimuli should be delivered later, then method 300 may go to block 308 and may increase (e.g., up to about 5, 10, or 15 ms) the AV delay. Otherwise, method 300 may go to block 310 and processor 80 may decrease (e.g., up to about 5, 10, or 15 ms) the AV delay to deliver pacing stimuli earlier to the later depolarizing ventricle, in particular earlier than IMD 16 previously delivered pacing pulses thereto.

After decreasing the AV delay and storing the new AV delay into memory at block 310, then method 300 may continue to blocks 312, 314 to cause processor 80 to perform a counting operation that ensures that sufficient sensed data over a period of time has been acquired and checked in order to find an optimum AV delay via method 300. Block 312 may determine whether N=N+1. N can be initialized at 1 (or 0) when method 300 is performed. N can be re-initialized to "1" by processor 80 when method 300 is re-started after a certain time period has expired (e.g., about 10 minutes, about 1 hour, about 1 day etc.).

Each time the logic of method 300 loops, or iterates, through block 312, then N may be increased by "1" by processor 80 according to the equation of N=N+1. At decision block 314, processor 80 may determine whether N=P where P is a pre-defined integer that provides a maximum number of times (e.g., up to 10 times) that sensed data is acquired via block 302 to determine if the pacing parameters should deliver pacing pulses earlier or later than the present pacing parameters stored in memory 82 of the IMD 16. Block 314 may return to block 304 in which a determination is made by processor 80 as to whether one or more pacing parameters need to be adjusted. One example of determining whether pacing parameters need to be adjusted may be based on whether a QRS duration exceeds a threshold.

The YES path from block 314 may continue to block 316 in which the optimal atrial-activation to bundle-pacing delay (e.g., AV delay or interval) may be selected from a set of atrial-activation to bundle-pacing intervals by processor 80 that were acquired while IMD 16 performed method 300 and that were stored in the IMD memory 82. In one or more embodiments, the IMD 16 will be set such that a minimal duration is employed. For example, after five cycles of AV delay at about 80, 90, 100, 110, and 120 ms, QRS duration may be correspondingly reduced to about 120, 100, 95, 93, and 99 ms, respectively. The optimal QRS duration may be determined to be 93 ms, which corresponds to an AV delay 110 ms, and as such, the 110 ms AV delay may be stored in the memory.

In another example, whether bundle pacing timing should be adjusted may be based on dyssynchrony, or a measure of dyssynchrony. Non-limiting examples of detecting dyssynchrony include using: a comparison of a bundle-pacing to RV-sensing interval with a bundle-pacing to LV-sensing interval, a QRS morphology change, or both. Using a QRS morphology change may include comparing a current QRS morphology to a predetermined QRS morphology representative of an RBBB or LBBB pattern in the patient's heart. In some embodiments, in response to determining that bundle-pacing timing should be adjusted using dyssynchrony, the method may determine that bundle-pacing output should be adjusted.

At block 318, the atrial-activation to bundle-pacing interval may be set to employ the optimized interval for bundle pacing. At block 320, the IMD 16 may be configured to pace the His bundle or bundle branch tissue. In particular, processor 80 may control an electrical pulse generator to deliver a bundle pace on expiration of a defined AV interval, which may follow atrial activation, or upon expiration of a bundle-pacing to ventricular-activation interval, which may follow ventricular activation.

FIG. 13 is a flowchart of left bundle branch pacing in synchronization with (back-up) RV pacing during left bundle branch block. As described in FIG. 13, left bundle branch pacing in synchronization with (back-up) RV pacing during left bundle branch block (LBBB) may be utilized during atrial fibrillation, in which reliable atrial sensing/pacing is unavailable, after AV node ablation, or after there is right bundle branch injury during bundle pacing lead implantation. In the example of FIG. 13, the bundle pacing lead may be located in the His bundle or bundle branch region, the RV lead may be positioned in the right ventricle. By adjusting bundle pacing time in reference with RV pacing time, a narrow QRS duration can be achieved.

In FIGS. 12 and 13, a variable can trigger adjustment of atrial-to-bundle pacing interval. In some embodiments, the variable used for triggering bundle pacing is QRS duration. Other variables for triggering bundle pacing adjustment can include a change in the interval from the time of bundle-pacing to RV-sensing, to LV-sensing, or to far-field R-wave, or even a QRS morphology that differentiates the RV and LV activation time. For example, if bundle-pacing to RV-sensing interval is 80-100 ms longer than bundle-pacing to far-field R-wave, bundle pacing should be delayed in steps of 10 ms until bundle-pacing to RV-sensing interval is equal to or slightly longer than bundle-pacing to far-field R-wave interval (e.g., if intrinsic activation is available) or initiate RV pacing at an interval equal to or slightly longer than bundle-pacing to far-field R-wave interval.

In FIG. 12, the "bundle pacing to RV sensing <80 ms" can be a function of AV (or PR) interval, such as 40-60% of AV (or PR) interval, for example, if bundle-pacing to RV-sensing interval is less than 40% of AV or PR interval, the A-bundle pacing interval can be delayed by 10 ms (e.g., see the delay mechanism in FIGS. 12 and 13). The "PR" interval refers to the interval between the P-wave and the R-wave in the QRS complex.

Additionally, the algorithm can distinguish between the LBBB pattern or the RBBB pattern, so the bundle pacing can be better synchronized with either intrinsic activation or ventricular pacing. For example, when the bundle pacing is used to correct LBBB and the RV sensing is delayed near the end of the detected far-field ECG, which may suggest the presence of delayed RV activation (RBBB), the bundle pacing may be delayed with a longer atrial-His pacing interval for bundle pacing to be synchronized with activation from atria, or RV pacing may be delivered earlier so that paced RV activation can be better synchronized with bundle pacing, leading to narrowed QRS duration. In general, bundle pacing may be adapted to achieve synchrony of the patient's heart in a manner manifested in a plurality of far-field electrical signals as a narrowed QRS duration or as a correction of LBBB or RBBB patterns in QRS morphology.

Similarly, if RV sensing occurs too early at the very beginning of a far-field EGM (or far before LV sensing), which may suggest bad synchronization, bundle pacing may be delivered earlier or RV pacing may be delayed, so that paced RV activation can be better synchronized with bundle pacing, leading to narrowed QRS duration.

While in some embodiments the time adjustment of bundle pacing is based on the QRS duration, it can also be based on the interval of bundle-pacing to RV- or LV-sensing, or even based on the detection of the presence of RBBB or LBBB (as described above) in case the device does not, or cannot, measure QRS duration. Additionally, the morphology of far- and near-field EGM and/or surface ECG may be used to estimate the activation delay in one or both ventricles. For example, in RV lead recording, if the EGM morphology of the RV tip-ring (e.g., the tip towards LV) is biphasic from a positive direction to a negative direction, meaning the propagation is from LV to RV, then the left bundle pacing may be delayed until a positive monophasic waveform followed with a relatively long small negative waveform is recorded. A similar method can be used to detect the activation propagation in the left ventricle.

Various methods may be used to detect dyssynchrony in the patient's heart for use in His bundle or bundle branch pacing. In some embodiments, a change between time intervals may be detected when an RV lead and/or an LV lead is available or used. For example, an increase in the difference between the pacing to RV-sensing interval and the pacing to LV-sensing interval or an increase in QRS duration may be detected based on electrical signals measured using the RV lead and/or the LV lead. The IMD may then be able to correct for the change in time intervals by adjusting the pacing timing for RV or for LV, or adjusting the timing of His pacing or bundle branch pacing, or adjusting the pacing output, according to techniques described herein.

In some other embodiments, when an RV lead and/or an LV lead is not available or used, a method may be used to calibrate an IMD to facilitate detection of an RBBB condition and/or an LBBB condition. The method may include pacing the LBB. For example, an intracardiac IMD, or leadless pacing device (LPD), may be configured to pace the LBB and the RBB. In response to pacing the LBB, an RBBB pattern may be observed, or detected, by the IMD using a far-field electrical signal, such as a far-field EGM. The IMD may determine and store the QRS morphology that corresponds to the detected RBBB pattern in the far-field electrical signal, or EGM. The IMD may also pace the RBB. In response to pacing the RBB, an LBBB pattern may be observed, or detected, using a far-field electrical signal, such as a far-field EGM. The IMD may determine and store the QRS morphology that corresponds to the detected LBBB pattern in the far-field electrical signal, or EGM. After calibration, the stored QRS morphologies corresponding to RBBB and LBBB patterns may be used to detect RBBB or LBBB conditions using the IMD. The IMD may then be able to correct for RBBB or LBBB by pacing the RBB earlier or LBB earlier according to techniques described herein. In some embodiments, an SD may be used to detect far-field electrical signals to detect dyssynchrony.

In some further embodiments, when a patient is known to have an existing LBBB or RBBB condition, the IMD may be used to memorize the corresponding LBBB or RBBB patterns of the condition using far-field electrical signals detected by the IMD. If the condition returns, which may be detected by comparing the memorized LBBB or RBBB patterns to measured far-field electrical signals, the IMD may operate to correct for LBBB or RBBB by pacing the RBB or the LBB earlier according to the techniques described herein.

In patients with pacing leads in RV and LV, the time difference between an RV sensed signal and an LV sensed signal may be used to represent the dyssynchrony between RV and LV. If the time difference increases, then dyssynchrony may be present, and pacing time in RV or LV may be adjusted or pacing time in LBB or RBB may be adjusted. In addition, the time of the greatest R-wave in a far-field EGM usually represents LV activation time. Thus, if the patient has only RV electrode (no LV electrode), then the EGM R-wave time may be compared with RV local time to determine the difference. If the difference increases, it may represent the presence of dyssynchrony.

FIG. 13 shows a flowchart of one example of method 400, which incorporates herein by reference method 300, including all the same blocks shown and described in FIG. 12. Method 400 may begin with block 302 by sensing heart activity and storing the data into memory 82. At block 330, a determination may be made as to whether QRS parameter, or activation interval, is greater than or equal to a threshold (T), such as 110, 120, 130, or 140 ms. One example of a QRS parameter is QRS duration. One example of an activation interval is a bundle-pacing to ventricular-activation interval.

If the QRS parameter is not greater than or equal to T, then heart activity may continue to be sensed at block 302. The YES path from block 330 indicates the QRS parameter is greater or equal to T and method 400 may continue to adjust a time interval for bundle pacing. In particular, method 400 may continue to decision block 306 in which a determination is made as to whether to deliver pacing pulses earlier or later than the current timing. The time interval for bundle pacing may include, but is not limited to, an atrial-activation to bundle-pacing interval or a bundle-pacing to an LV- or RV-activation interval.

If a determination is made that the pacing pulses should be delivered later, the path may continue to block 308 in which the AV delay is increased (e.g., up to 10 ms steps) and may return to decision block 330; otherwise, when pacing should be delivered earlier, the path may continue to block 310 to decrease the AV delay (e.g., up to 10 ms steps). Block 308 may return to block 330.

After block 310, decision block 332 may determine whether a QRS parameter or activation interval is less than a second threshold, such as 110, 120, 130, or 140 ms. The YES path from block 332 may return to sensing heart activity at block 302, for example, because decreasing the AV delay in block 310 corrected the QRS parameter or activation interval. The NO path from block 332 may continue to decision block 334 in which a determination is made as to whether the QRS duration has increased.

In response to block 334, if the QRS duration has not increased, method 400 may continue to block 336, in which a counter M is increased by "1". At block 338, if M=Q, where Q indicates a maximum number of iterations, then method 400 may continue to block 316. Q may be an integer that is typically 10 or less and may ensure a number of loops are made to decrease the AV delay. If M≠Q, then method 400 may return to block 310 to continue decreasing AV delay. For example, QRS duration may decrease from 150 ms to 135 ms (e.g., a 15 ms step) such that the decrease in AV delay is in the right direction but may still be greater than 120 ms, so there may be a need to continue to decrease AV delay until QRS duration is less than or equal to 120 ms or adjustment is exhausted (e.g., M=Q). If the QRS duration has increased, method 400 may continue to block 340, in which bundle pacing output (e.g., His pacing output or bundle branch pacing output) is increased.

At block 342, a determination may be made as to whether QRS duration is less than a threshold (e.g., 120 ms). The YES path from block 342 may return to block 302 to continue sensing heart activity. In contrast, the NO path may continue to decision block 346 to determine whether QRS duration increased. The NO path may continue such that counter S is increased by "1" in which S=S+1 at block 350 and then may continue to decision block 352 to determine whether S=R in which R is an integer of less than 10. If S=R, then method 400 may continue to block 316 in which the optimal AV delay is selected. The optimal AV delay may be automatically selected. Alternatively, a user may select an AV delay from the set of AV delays presented to the user on a graphical user interface presented through programmer 24 or a cell phone controlled by the user. The optimal AV delay for pacing may be saved in block 318. Pacing may be delivered using optimal AV delay in block 320.

FIG. 14 shows a flowchart of an example of method 500, which may optimize VV delay for pacing of the His bundle or one or both bundle branches. At block 502, the IMD 16 may deliver electrical stimuli (e.g., pacing pulses) to the His bundle or one or both bundle branches. At block 504, heart activity may be sensed in the same or similar manner as described with respect to block 302. At decision block 506, a determination may be made as to whether RV sensing is occurring earlier than LV sensing (e.g., earlier than or at the same time). For example, during His or bundle branch pacing that corrects LBBB, if RV sensing is 50 ms earlier than LV sensing, this may mean that LV activation by bundle pacing is occurring later, so it may be beneficial to initiate bundle branch pacing for LBBB correction at an appropriate (earlier) time in synchronization with RV sensing. In another example, when an LV lead is available, if bundle-pacing to RV-sensing interval is 40 ms, and bundle-pacing to LV-sensing interval is 85 ms, then bundle branch pacing may be delivered and LV pacing with the LV lead may be adjusted to be delivered 40-50 ms earlier than bundle pacing, as a result, RV and LV activation may occur at almost the same time.

The YES path from block 506 may continue to block 508 in which bundle pacing may be adjusted to LV pacing timing (or LV activation), for example, when an LV lead is available. The NO path from block 506 may continue to decision block 510 in which a determination may be made as to whether RV sensing occurs later than LV sensing (e.g., later than or at the same time). The NO path from decision block 510 may return to delivering pacing at block 502 to the His bundle or one or both bundle branches and then sensing heart activity in response to the delivered pacing pulses at block 504. The YES path from block 510 may continue to block 512 in which bundle pacing may be adjusted to RV pacing timing (or RV activation), for example, when an RV lead is available.

The path may continue to decision block 514 in which a determination may be made as to whether adjustment criteria are satisfied. One example of determining whether adjustment criteria are satisfied may include determining whether the timing of RV sensing and LV sensing are almost the same, such as less than or equal to about 40, 30, 20, or 10 ms. Another example of determining whether adjustment criteria are satisfied may include determining whether the RV-sensing to LV-sensing interval is optimal. The optimal the interval from RV-sensing to LV-sensing may be predetermined by monitoring, for example, using an echocardiogram, to find the optimal interval at which the cardiac output is the most, or highest, or mechanical and/or electrical synchronization is best, or optimal. Alternatively, the optimal interval from RV-sensing to LV-sensing can be predetermined using a 12-lead body surface ECG in which the interval generates the shortest QRS duration. Further, the optimal interval from RV-sensing to LV-sensing may be predetermined using an ECG belt (e.g., multiple-channel body surface mapping) that shows the most synchronized pattern at a particular interval from RV-sensing to LV-sensing. This predetermined interval may typically vary from about −20 ms to +40 ms, or around 0 ms, which may depend on where the RV and LV pacing leads are located in the ventricles.

The YES path from decision block 514 may continue to deliver pacing at block 502. The NO path from decision block 514 may return to 512 to adjust the bundle pacing to RV activation timing.

The path from block 508 may continue to decision block 515 in which a determination may be made as to whether adjustment criteria are satisfied. The determination as to whether adjustment criteria are satisfied may be made in the same or similar manner as described with respect to block 514 (e.g., using the same adjustment criteria). The YES path from block 515 may continue to deliver pacing at block 502. The NO path from decision block 515 may return to block 508 to adjust bundle pacing to LV activation timing.

While FIGS. 12-14 are described relative to a particular pacing parameter (e.g., QRS parameters, such as QRS duration) to initiate the adjustment of an atrial-to-bundle pacing interval, other variables can also be used to adjust atrial-to-bundle pacing interval. Other illustrative pacing parameters that can be used include a change in the interval of bundle-pacing to RV- and/or LV-sensing or bundle-pacing to far-field R-wave. For example, if a bundle-pacing to RV-sensing interval is 80-100 milliseconds longer than a bundle-pacing to far-field R-wave interval, bundle pacing may be delayed at block 308 by a certain amount of time (e.g., 10 milliseconds etc.) until the bundle-pacing to RV-sensing interval is equal to or slightly longer than the bundle-pacing to far-field R-wave interval (if intrinsic activation available) or RV pacing may be initiated at an interval equal to or slightly longer than bundle-pacing to far-field R-wave interval.

In general, QRS parameters may include, but are not necessarily limited to, QRS duration, QRS morphology change, QRS vector change, or QRS pattern (e.g., RBBB or LBBB pattern).

In FIG. 12, at block 306, the "bundle pacing to RV sensing <80 ms" can be a function of AV (or PR) interval, such as 40-70% of AV (or PR) interval, for example, if bundle pacing to RV sensing interval is less than 40% of AV or PR interval, the atrial to bundle-pacing interval may be increased (e.g., see the delay mechanism in FIGS. 12 and 13). Additionally, the algorithm can distinguish the pattern of LBBB or RBBB so the bundle pacing can be better synchronized with either intrinsic activation or ventricular pacing. For example, when the bundle pacing is used to correct LBBB and the RV sensing is delayed near the end of the detected far-field ECG, suggesting the presence of delayed RV activation (RBBB), the bundle pacing should be delayed with a longer atrial to bundle-pacing interval for bundle pacing to be synchronized with activation from atria, or RV pacing should be delivered earlier so paced RV activation can be better synchronized with bundle pacing. Similarly, if RV sensing occurs too early at the very beginning of the far-field EGM (or far before LV sensing), suggesting bad synchronization, in such a case, bundle pacing may occur earlier, or RV pacing may be delayed. While the time adjustment of bundle pacing may be based on the QRS duration in some embodiments, it can also be based on the interval of bundle-pacing to RV- or LV-sensing or based on the detection of the presence of RBBB or LBBB (as described above) in case the device does not or cannot measure QRS duration. Additionally, the morphology of far- and near-field EGM and surface ECG can be used to estimate the activation delay in which ventricle. For example, in RV lead recording, if the EGM morphology of the RV tip-ring (the tip towards LV) is biphasic from the positive direction to the negative direction, meaning the propagation of the signal is from LV to RV. Consequently, the left bundle pacing should be delayed until a positive monophasic waveform followed with a relatively long small negative waveform is recorded. A similar method can be used to detect the activation propagation in the left ventricle.

The algorithm may also distinguish an LBBB pattern from an RBBB pattern using only far-field electrical signals. For example, the morphology of far-field EGM with LBBB (or RBBB) can be obtained during implantation by applying right bundle branch pacing (causing LBBB morphology) or left bundle branch pacing (causing RBBB morphology). If the patient already has an existing LBBB, then the device EGM can memorize the morphology of EGM when no pacing is applied. Different patients can have different EGM morphology for LBBB or RBBB, which may be obtained and personalized after implantation with left or right bundle branch pacing or by using existing LBBB/RBBB information.

The implantable medical device used in various embodiments of the present disclosure may be a leadless pacing device (LPD), which may communicate with another implantable medical device, such as a subcutaneous device.

FIG. 15 shows an example system 610 that includes a subcutaneous device (SD) as IMD 630 (e.g., SICD, loop recorder (e.g., REVEAL®), etc.) implanted exterior to a rib cage of patient 14 and leadless pacing device (LPD) 616 implanted within right atrium 26 of patient 14. IMD 630 can be implanted external to a rib cage and within the vasculature. Additionally, or alternatively, an implantable medical device can be implanted substernally/retrosternally, as described in U.S. Patent Application 61/819,946, entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE" filed May 6, 2013, incorporated by reference in its entirety. In the example of FIG. 15, system 610 includes LPD 616 and IMD 630. External programmer 670 may be configured to communicate with one or both of LPD 616 and IMD 630. Generally, there are no wires or other direct electrical (e.g., hardwired) connections between IMD 630 and LPD 616. In this manner, any communication between IMD 630 and LPD 616 may be described as "wireless" communication. Patient 14 is ordinarily, but not necessarily, a human patient.

Illustrative IMD 630 includes housing 632 configured to be subcutaneously implanted outside the rib cage of patient 14. The subcutaneous implantation location may be anterior to the cardiac notch, for example. In addition, housing 632 may carry three subcutaneous electrodes 634A-634C (collectively "electrodes 634"). In other examples, housing 632 may carry fewer or greater than three electrodes. Lead 636 may be configured to couple to housing 632 and extend from housing 632 to a different subcutaneous location within patient 14. For example, lead 636 may be tunneled laterally and posteriorly to the back of patient 14 at a location adjacent to a portion of a latissimus dorsi muscle. Lead 636 may carry electrode coil 638 along a length of lead 636 and sensing electrode 640 at a distal end of lead 636. IMD 630 may be configured such that heart 12 may be disposed at least partially between housing 632 and electrode coil 638 of lead 636. In some examples, lead 636 may carry two or more electrode coils 638 and/or two or more sensing electrodes 640.

IMD 630 may contain, within housing 632, signal processing and therapy delivery circuitry to detect cardiac conditions (e.g., ventricular dyssynchrony, arrhythmias such as bradycardia and tachycardia conditions etc.) and to communicate with LPD 616 to apply appropriate electrical stimuli (e.g. pacing and/or anti-tachyarrhythmia shock therapy (e.g., defibrillation or cardioversion shocking pulses)) to heart 12. IMD 630 also may be configured to apply pacing pulses via one or more electrodes 634. IMD 630 may be configured to apply the anti-tachyarrhythmia shock pulses between coil electrode 638 and one or more of electrodes 634 and/or electrically conductive housing 632 (e.g., an additional can electrode) of IMD 630. IMD 630 may be configured to communicate with programmer 670 via an RF communication link, inductive coupling, or some other wireless communication protocol.

In some embodiments, IMD 630 differs from previously used ICDs in that housing 632 may be larger in size than the housing of some existing ICDs to accommodate larger capacity batteries, for example. In addition, IMD 630 may be implanted subcutaneously whereas some existing ICDs may be implanted under muscle or deeper within patient 14. In other examples, housing 632 may be shaped or sized differently to be implanted subcutaneously instead of under a muscle or within deep tissue. Moreover, IMD 630 may not include leads configured to be placed in the bloodstream (e.g., endocardial or epicardial leads). Instead, IMD 630 may be configured to carry one or more electrodes (e.g., electrodes 634) on housing 632 together with one or more subcutaneous leads (e.g., lead 636) that carry defibrillation coil electrode 638 and sensing electrode 640. In other examples, lead 636 may include additional electrodes. These subcutaneously implanted electrodes of IMD 630 may be used to provide therapies similar to that of existing ICDs without invasive vascular leads. In other examples, the exact configuration, shape, and size of IMD 630 may be varied for different applications or patients. Although IMD 630 is generally described as including one or more electrodes, IMD 630 may typically include at least two electrodes to deliver electrical stimulation (e.g., therapy) and/or provide at least one sensing vector. Other illustrative SDs, or IMD 630, can be used in combination with LPD 616. For example, IMD 630 may include, or be, an intravenously implanted device (IID), an ICD, a pacemaker, or any other suitable device.

System 610 also includes one or more LPDs, such as LPD 616. LPD 616 may be, for example, an implantable leadless pacing device (e.g., a pacemaker, cardioverter, and/or defibrillator) that provides electrical stimulation to heart 12 via electrodes carried on the housing of LPD 616. In the example of FIG. 15, LPD 616 is implanted within left ventricle 32 of heart 12 to sense electrical activity of heart 12 and/or deliver electrical stimulation, e.g., CRT such as fusion pacing, to heart 12. Fusion pacing involves left ventricle (LV) 32 only pacing with an electrode on the LPD 616 in coordination with intrinsic right ventricle (RV) activation. Alternatively, fusion pacing can involve pacing RV 28 with an electrode on LPD 616 in coordination with intrinsic LV activation. In this scenario, LPD 616 is placed within the RV 28.

LPD 616 is schematically shown in FIG. 15 attached to a wall of right atrium (RA) 26 via one or more fixation elements (e.g. tines, helix etc.) that penetrate the tissue. These fixation elements may secure LPD 616 to the cardiac tissue and retain an electrode (e.g., a cathode or an anode) in contact with the cardiac tissue. One or more electrodes may be positioned to stimulate the tissue of RA 26, LV 32, or both RA 26 and LV 32. LPD 616 may also include one or more motion sensors (e.g., accelerometers) configured to detect and/or confirm cardiac conditions (e.g., ventricular dyssynchrony, tachyarrhythmias etc.) from mechanical motions of heart 12. Since LPD 616 may include two or more electrodes carried on the exterior housing of LPD 616, no other leads or structures may need to reside in other chambers of heart 12. However, in other examples, system 610 may include additional LPDs within respective chambers of heart 12 (e.g., left atrium (LA) 33, RV 28, and/or LV 32).

Using the electrodes carried on the housing of LPD 616, LPD 616 may be capable sensing intrinsic electrical signals, e.g., an electrocardiogram (ECG). IMD 630 may similarly sense intrinsic electrical signals from the sensing vectors of electrodes 634, 638, and 640. These intrinsic signals may be electrical signals generated by cardiac muscle and indicative of depolarizations and repolarizations of heart 12 at various times during the cardiac cycle. LPD 616 may generate electrograms from these cardiac signals that may be used by LPD 616 to detect cardiac conditions (e.g. ventricular dyssynchrony, arrhythmias, such as tachyarrhythmias), or identify other cardiac events, e.g., ventricle depolarizations or atrium depolarizations. LPD 616 may also measure impedances of the carried electrodes and/or determine capture thresholds of those electrodes intended to be in contact with cardiac tissue. In addition, LPD 616 may be configured to communicate with external programmer 670. The configurations of electrodes used by LPD 616 for sensing and pacing may be typically considered bipolar but unipolar may also be used.

External programmer 670 may be configured to communicate with one or both of IMD 630 and LPD 616. In examples which external programmer 24 only communicates with one of IMD 630 and LPD 616, the non-communicative device may receive instructions from or transmit data to the device in communication with programmer 670. In some examples, programmer 670 includes a handheld computing device, computer workstation, or networked computing device. Programmer 670 may include a user interface that receives input from a user. In other examples, the user may also interact with programmer 670 remotely via a networked computing device. The user may interact with programmer 670 to communicate with LPD 616 and/or IMD 630. For example, the user may interact with programmer 670 to send an interrogation request and retrieve therapy delivery data, update therapy parameters that define therapy, manage communication between LPD 616 and/or IMD 630, or perform any other activities with respect to LPD 616 and/or IMD 630. Although the user may be a physician, technician, surgeon, electrophysiologist, or other healthcare professional, the user may be patient 14 in some examples.

Programmer 670 may also allow the user to define how LPD 616 and/or IMD 630 senses electrical signals (e.g., ECGs), detects cardiac conditions (e.g. ventricular dyssynchrony, arrhythmias etc.), delivers therapy, and communicates with other devices of system 610. For example, programmer 670 may be used to change detection parameters. In another example, programmer 670 may be used to manage therapy parameters that define therapies such as CRT. Moreover, programmer 670 may be used to alter communication protocols between LPD 616 and IMD 630. For example, programmer 670 may instruct LPD 616 and/or IMD 630 to switch between one-way and two-way communication and/or change which of LPD 616 and/or IMD 630 are tasked with initial detection of a cardiac condition.

Programmer 670 may communicate with LPD 616 and/or IMD 630 via wireless communication using any techniques known in the art. Examples of communication techniques may include, for example, radiofrequency (RF) telemetry, but other techniques are also contemplated. In some examples, programmer 670 may include a programming head that may be placed proximate to the patient's body near the LPD 616 and/or IMD 630 implant site in order to improve the quality or security of communication between LPD 616 and/or IMD 630 and programmer 670.

LPD 616 and IMD 630 may engage in communication to facilitate appropriate detection of ventricular dyssynchrony and/or delivery of CRT. The communication may include one-way communication in which one device is configured to transmit communication messages and the other device is configured to receive those messages. The communication may include two-way communication in which each device is configured to transmit and receive communication messages. LPD 616 and IMD 630 may be configured to communicate with each other provide alternative electrical stimulation therapies.

Although LPD 616 may at least partially determine whether or not LPD 616 delivers CRT or another therapy to patient 14, LPD 616 may perform one or more functions in response to receiving a request from IMD 630 and without any further analysis by LPD 616. In this manner, IMD 630 may act as a master device and LPD 616 may act as a "slave" device. In this configuration, LPD 616 passively senses. Specifically, a mode may be employed as a trigger mode to pace in synchrony (e.g., a WT mode). In one or more embodiments, LPD 616 may be configured to actively sense.

FIG. 16 shows one example of LPD 616 of FIG. 15. As shown in FIG. 16, LPD 616 includes case 650, cap 658, electrode 660, electrode 652, tissue-piercing electrode assembly 661 (which may also function as a fixation mechanism (e.g., with a helix shape)), flange 654, and opening 656. In general, the tissue-piercing electrode assembly 661 extends axially from a housing of LPD 616. Together, case 650 and cap 658 may be considered the housing of LPD 616. In this manner, case 650 and cap 658 may enclose and protect the various electrical components within LPD 616. Case 650 may enclose substantially all the electrical components, and cap 658 may seal case 650 and create the hermetically sealed housing of LPD 616. Although LPD 616 is generally described as including one or more electrodes, LPD 616 may typically include at least two electrodes (e.g., electrodes 652 and 660) to deliver an electrical signal (e.g., therapy such as CRT) and/or provide at least one sensing vector. Electrodes 652 and 660 are carried on the housing created by case 650 and cap 658. In this manner, electrodes 652 and 660 may be considered leadless electrodes. In the example of FIG. 15, electrode 660 is disposed on the exterior surface of cap 658. Electrode 660 may be a circular electrode positioned to contact cardiac tissue upon implantation. Electrode 652 may be a ring or cylindrical electrode disposed on the exterior surface of case 650. Both case 650 and cap 658 may be electrically insulating. Electrode 660 may be used as a cathode and electrode 652 may be used as an anode, or vice versa, for delivering CRT or other appropriate cardiac therapy (ATP, shock, etc.). However, electrodes 652 and 660 may be used in any stimulation configuration. In addition, electrodes 652 and 660 may be used to detect intrinsic electrical signals from cardiac muscle. In other examples, LPD 616 may include three or more electrodes, where each electrode may deliver therapy and/or detect intrinsic signals. CRT delivered by LPD 616 may be considered to be "painless" to patient 14 or even undetectable by patient 14 since, e.g., the electrical stimulation occurs very close to or at cardiac muscle and at relatively low energy levels compared with alternative devices.

One or more fixation mechanisms of tissue-piercing electrode assembly 661 may attach LPD 616 to cardiac tissue. The fixation mechanisms may include a helix (as illustrated), active fixation tines, screws, clamps, adhesive members, or any other types of attaching a device to tissue. In some embodiments, fixation mechanisms may be constructed of a memory material that retains a preformed shape. During implantation, fixation mechanisms may be flexed forward to pierce tissue and allowed to flex back towards case 650. In this manner, fixation mechanisms may be embedded within the target tissue.

Flange 654 may be provided on one end of case 650 to enable tethering or extraction of LPD 616. For example, a suture or other device may be inserted around flange 654 and/or through opening 656 and attached to tissue. In this manner, flange 654 may provide a secondary attachment structure to tether or retain LPD 616 within heart 12 if fixation mechanisms fail. Flange 654 and/or opening 656 may also be used to extract LPD 616 if explantation (or removal) from patient 14 is desired.

FIGS. 17A-17B are conceptual diagrams of patient 14 implanted with implantable cardiac system 610 that includes LPD 616 inside the heart in order to deliver bundle pacing to His bundle or bundle branch tissue. Implantable cardiac system 610 that contains a substernal/subcutaneous device (SD), or IMD 630, can implement method 300-500 as described herein. FIG. 17A is a front view of patient 14 implanted with implantable cardiac system 610. FIG. 17B is a side view patient 14 with implantable cardiac system 610.

Implantable cardiac system 610 includes an implantable medical device (IMD) 630 such as an implantable cardiac defibrillator (ICD) or pacemaker connected to a defibrillation lead 636. In the example illustrated in FIGS. 17A-B, IMD 630 is implanted subcutaneously on the left midaxiallary of patient 14. IMD 630 may, however, be implanted at other subcutaneous locations on patient 14 as described herein.

Defibrillation lead 636 includes a proximal end that is connected to IMD 630 and a distal end that includes one or more electrodes. Defibrillation lead 636 extends subcutaneously from IMD 630 toward xiphoid process 620. At a location near xiphoid process 620, defibrillation lead 636 bends or turns and extends subcutaneously superiorly, substantially parallel to sternum 622. The distal end of defibrillation lead 636 may be positioned near the second or third rib of patient 14. However, the distal end of defibrillation lead 636 may be positioned further superior or inferior depending on the location of IMD 630 and other factors. Although illustrated as being offset laterally from and extending substantially parallel to sternum 622 in the example of FIGS. 17A-B, defibrillation lead 636 may be implanted over sternum 622, offset from sternum 622, but not parallel to sternum 622 (e.g., angled lateral from sternum 622 at either the proximal or distal end).

Defibrillation lead 636 includes defibrillation electrode 638, which may be an elongated coil electrode, toward the distal end of defibrillation lead 636. Defibrillation lead 636 is placed such that a therapy vector between defibrillation electrode 638 and a housing or can electrode of IMD 630 is substantially across the ventricle of heart 12.

Defibrillation lead 636 may also include sensing and/or pacing electrodes 640 and 642 located toward the distal end of defibrillation lead 636. In the example illustrated in FIGS. 17A-B, sensing electrode 640 and 642 are separated from one another by defibrillation electrode 638. IMD 630 may sense electrical activity of heart 12 via a combination of sensing vectors that include combinations of electrodes 640 and 642 and the housing or can electrode of IMD 630. For example, IMD 630 may obtain electrical signals sensed using a sensing vector between electrodes 640 and 642, obtain electrical signals sensed using a sensing vector between electrode 640 and the conductive housing or can electrode of IMD 630, obtain electrical signals sensed using a sensing vector between electrode 642 and the conductive housing or can electrode of IMD 630, or a combination thereof. In some instances, IMD 630 may even sense cardiac electrical signals using a sensing vector that includes defibrillation electrode 638.

IMD 630, which may be an ICD, may analyze the sensed electrical signals from one or more of the sensing vectors of defibrillation lead 636 to detect ventricular dyssynchrony (e.g., widening QRS duration, time difference between RV and LV activation components in ECG vectors, and atrial signal of P wave in ECG) and/or other cardiac conditions (e.g., tachycardia, fibrillation). In response to detecting the ventricular dyssynchrony, IMD 630 may communicate with LPD 616 to initiate bundle pacing at a particular timing for resynchronization and/or cardiac resynchronization therapy pacing in an attempt to terminate the ventricular dyssynchrony. The means of communication between LPD 616 and IMD 630 is the same or similar as that which is described herein.

LPD 616 is implanted in the His bundle or bundle branch region and communicatively coupled to IMD device 630. LPD 616 and IMD device 630 may, for example, both include a communication module via which the devices exchange wireless communications. LPD 616 and IMD device 630 may, for example, be coupled via inductive coupling, RF coupling, tissue conductance communication, or other wireless communication mechanism.

As indicated above, LPD 616 may be implanted in the His bundle region or bundle branch region. LPD 616 is configured to include a housing, electrodes coupled to the housing or formed by the housing, and a fixation mechanism (e.g., helix) to attach LPD 616 at a His bundle location.

LPD 616 may sense electrical activity of heart 12 via electrodes and provide pacing pulses to heart 12 via the same or different electrodes. The pacing pulses provided to heart 12 may be responsive to sensed electrical signals of the heart sensed either via electrodes of LPD 616 or sensed via one or more electrode combinations of defibrillation lead 636. LPD 616 may generate and deliver pacing pulses with any of a number of amplitudes and pulse widths to capture heart 12.

LPD 616 may also analyze the sensed electrical signals from one or more of the sensing vectors of LPD 616 and/or from the IMD to detect ventricular dyssynchrony. LPD 616 may not deliver pacing therapy until LPD 616 receives communication from IMD 630 indicating detection of ventricular dyssynchrony by IMD 630.

The configuration described above in FIGS. 17A-B is directed to providing ventricular pacing via LPD 616 positioned near the His bundle or one or both bundles. In some instances, more than one LPD 616 may be utilized for multi-chamber pacing, e.g., with one LPD 616 providing atrial pacing and another LPD 616 providing ventricle pacing. Alternatively, LPD 616 may be positioned over the ventricle and include a small tether extending up to the atrium with an electrode on the tether. LPD 616 could sense and/or pace via the electrode on the tether. In yet further embodiments, LPD 616 may be used in combination with a pacing lead implanted substernally to provide dual chamber pacing.

IMD 630 may include a housing that forms a hermetic seal that protects components of IMD 630. The housing of IMD 630 may be formed of a conductive material, such as titanium. IMD 630 may also include a connector assembly (also referred to as a connector block or header) that includes electrical feedthroughs through which electrical connections are made between conductors within the lead 636 and electronic components included within the housing. As will be described in further detail herein, housing may house one or more processors, memories, transmitters, receivers, sensors, sensing circuitry, therapy circuitry and other appropriate components. The housing is configured to be implanted in a patient, such as patient 14.

As described herein, lead 636 includes a lead body that may include electrodes 638, 640, 642 located near the distal lead end or elsewhere along the length of the lead body. The lead bodies of lead 636 also contain one or more elongated electrical conductors (not illustrated) that extend through the lead body from a connector assembly of IMD 630 provided at a proximal lead end to one or more electrodes of lead 636. The lead bodies of lead 636 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of lead 636 may engage with respective ones of electrodes 638, 640, 642. In one example, each of electrodes 638, 640, 642 is electrically coupled to a respective conductor within its associated lead body. The respective conductors may electrically couple to circuitry, such as a therapy module or a sensing module, of IMD 630 via connections in connector assembly, including associated feedthroughs. The electrical conductors transmit therapy from a therapy module within IMD 630 to one or more of electrodes 638, 640, 642 and transmit sensed electrical signals from one or more of electrodes 638, 640, 642 to the sensing module within IMD 630.

The examples illustrated in FIGS. 17A-B are illustrative in nature and should not be considered limiting of the techniques described in this disclosure. In other examples, IMD 630 and defibrillation lead 636 may be implanted at other locations. For example, IMD 630 may be implanted in a subcutaneous pocket in the right chest. In this example, defibrillation lead 636 may be extend subcutaneously from the device toward the manubrium of the sternum and bend or turn and extend subcutaneously inferiorly from the manubrium of the sternum, substantially parallel with the sternum.

System 610 may be further described as an IMD system that provides, but the techniques may be applicable to other cardiac systems, including cardiac resynchronization therapy defibrillator (CRT-D) systems, cardioverter systems, or combinations thereof.

The substernal/retrosternal IMD system 610 can be configured to deliver bundle pacing to synchronize the ventricles with each other. Bundle pacing includes pacing the His bundle or one or both bundles with one or more pacing electrodes. Pacing electrodes can be found on the bundle pacing lead or leadless pacing device. In addition, or alternatively, electrodes 640 and 642 of IMD 630 can be configured to deliver pacing pulse to the LV. The LV and/or RV is paced by separate electrodes.

Bundle pacing may be delivered while another type of pacing may be delivered to another tissue site. Illustrative cardiac pacing system that may employ both bundle pacing to a His bundle or bundle branch tissue site and another pacing therapy delivered to another pacing site (e.g., left ventricle or right ventricle) is disclosed in U.S. Pat. No. 9,789,319, entitled SYSTEMS AND METHODS FOR LEADLESS CARDIAC RESYNCHRONIZATION THERAPY that issued Oct. 17, 2017, which is incorporated herein by reference in its entirety. U.S. Pat. No. 9,789,319 discloses, for example, a subcutaneous device and LPD in communication with each other. As applied to the present disclosure, the leadless pacing device (LPD) would be configured to deliver bundle pacing using an elongated helical tip that is similar or the same as the helical tip, for example, on the Medtronic 3830 lead.

The techniques described in this disclosure, including those attributed to an IMD, such as LPD 616, programmer 670, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

To achieve the best pacing output, bundle pacing may be synchronized with either intrinsic activation or either RV or LV pacing as described herein. In some embodiments, bundle pacing may be terminated only when a normal ventricular pattern with appropriate atrioventricular conduction interval is detected.

When implemented in software, the functionality ascribed to the systems, devices, and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

FIGS. 18A-B show patient's heart 12 implanted with IMD 716 operably coupled to implantable medical electrical lead 723 to deliver bundle branch pacing according to one example of an IMD system 710. FIG. 18B is a close-up view of lead 723 in the patient's heart 12 of FIG. 18A. In some embodiments, electrical lead 723 may be the only lead implanted in the patient's heart 12.

In particular, lead 723 may be configured for dual bundle branch pacing. Lead 723 may be the same as or similar to lead 23 (FIGS. 2A-B), except lead 723 is implanted near the bundle branches instead of, for example, the His bundle 13. As illustrated, lead 723 is implanted in the septal wall from RV 28 toward LV 32. Lead 723 may not pierce through the wall of LV 32 or extend into the LV chamber. Electrode 752 and tissue-piercing electrode assembly 761 may be disposed on a distal end portion of lead 723, which may also be described as a shaft. Electrode 752 and tissue-piercing electrode assembly 761 may be the same as or similar to electrode 652 and tissue-piercing electrode assembly 661 (FIG. 16), except electrode 752 is configured as a cathode electrode to sense or pace the RBB and electrode assembly 761 is configured to sense or pace the LBB, for example, during dual bundle branch pacing. Accordingly, electrode 752 may be implanted near RBB 8b, and electrode assembly 761 may be implanted near LBB 8a.

Electrode assembly 761 may be described as a unipolar cathode electrode, which may be implanted on the left side of the patient's septum. Electrode 752 may be described as a unipolar cathode electrode, which may be implanted on the right side of the patient's septum.

During dual bundle branch pacing, both electrode 752 and electrode assembly 761 (which also includes an electrode) may each deliver a cathodal pulse to achieve synchronized activation, or excitation, of RBB 8b and LBB 8a, which may result in synchronized activation of RV 28 and LV 32. In some embodiments, the pulses may be delivered at the same time to achieve synchrony. In other embodiments, the pulses may be delivered with a delay to achieve synchrony.

Lead 723 may include electrode 770 disposed more proximal to the electrode 752 and electrode assembly 761. Electrode 770 may be positioned in or near RA 26 and may function as an anode for cathodal pulses from electrode 752 and/or electrode assembly 761.

FIGS. 19A-H show electrical signals resulting from various pacing configurations applied to a patient with an LBBB. The electrical signals shown include electrogram (EGM) and electrocardiogram (ECG) information. FIG. 19E is similar to FIG. 8A in that a LBBB is shown without pacing. FIGS. 19F-H show various pacing configurations 800, 801, 802 at a distal His bundle pacing site similar to FIG. 8C. In particular, FIG. 19F shows a pacing configuration 800 that uses an AV delay of 40 ms, which results in the LV activating earlier than the RV as shown in the electrical signals of FIG. 19B. FIG. 19G shows pacing configuration 801 that uses an AV delay of 90 ms, which results in the LV activating simultaneously with the RV as shown in the electrical signals of FIG. 19C. FIG. 19H shows pacing configuration 802 that uses an AV delay of 160 ms, which results in the LV activating later than the RV as shown in the electrical signals of FIG. 19D. FIG. 19A shows resulting electrical signals of a pacing configuration (not shown) that uses an AV delay of 170 ms and looks like a full LBBB pattern, similar to intrinsic LBBB without pacing.

FIG. 20 shows electrical signals resulting from positioning a bundle branch pacing lead (see, for example, FIGS. 18A-B) at various locations in a patient with an LBBB and the resulting QRS duration (QRSd) in milliseconds (ms). In particular, electrical signals correspond to various locations as the bundle branch pacing lead advances from the right side to the left side of the bundle branches. Electrical signals 820A correspond to no pacing lead in the patient's heart (intrinsic) and a resulting QRSd of 102 ms. Electrical signals 820B correspond to the lead near the LBB without pacing resulting in a QRSd of 126 ms. Electrical signals 820C correspond to pacing near the RBB resulting in a QRSd of 140 ms, which may be characterized as a wide QRSd. Electrical signals 820D correspond to pacing in the middle of the RBB and LBB resulting in a QRSd of 138 ms. Electrical signals 820E correspond to pacing near the LBB resulting in a QRSd of 104 ms. Electrical signals 820F correspond to the lead near the LBB without pacing while recording bundle branch potentials, which looks similar to electrical signals 820B.

FIG. 21 shows electrical signals resulting from positioning a bundle branch pacing lead (see, for example, FIGS. 18A-B) at various locations in various patients with an RBBB or an LBBB and the resulting QRSd in milliseconds (ms). Electrical signals 821A, 821B correspond to a patient having an RBBB. Electrical signals 821A correspond to no pacing lead in the patient's heart and a resulting QRSd of 188 ms. Electrical signals 821B correspond to pacing near the RBB resulting in a QRSd of 132 ms, which corrects the RBBB. Electrical signals 821C to 821E correspond to a patient having an LBBB. Electrical signals 821C correspond to no pacing lead in the patient's heart (intrinsic) resulting in a QRSd of 178 ms. Electrical signals 821D correspond to pacing near the LBB resulting in a QRSd of 120 ms, which is a narrow QRS. Electrical signals 821E correspond to recording after implantation during LBB pacing and a resulting QRSd of 123 ms.

FIGS. 22A-B show various aspects of IMD system 710 including implantable medical lead 723 that may be used for bundle pacing, particularly dual bundle branch pacing. As illustrated in FIG. 22A, medical lead 723 may be directly coupled to IMD 716. IMD 716 may function as an electrode 770, for example, using a discrete electrode or a housing of IMD 716. As illustrated in FIG. 22B, lead 723 may include lead connector 790 disposed on a proximal end portion. Lead connector 790 may include contacts 753, 762 operably coupled to electrode 752 and electrode assembly 761, respectively, to operably couple with electronic circuitry of IMD 716, for example, when lead connector 790 is inserted into IMD 716.

Lead 723 may also include protrusion 772 (e.g., a shield or stopper) that may prevent electrode assembly 761 of lead 723 from advancing too far into cardiac tissue. In particular, protrusion 722 may prevent electrode assembly 761 of lead 723 from perforating the LV wall and extending into the LV. Protrusion 722 may extend laterally from a nominal surface of lead 723 to engage a wall of cardiac tissue when being implanted. Protrusion 722 may have a biased shape that facilitates the ease of retracting lead 723 while still preventing further advancement of lead 723 when protrusion 722 engages cardiac tissue. Protrusion 722 may be formed of any suitable material to facilitate its functionality. Protrusion 722 may be formed of a flexible, soft, and/or expansible material.

Protrusion 722 may have a height, or width, 784 extending orthogonally from the nominal surface of lead 723, such as the surface of distal end portion 724 of lead 723. Height 784 may be any suitable range to facilitate preventing further advancement of lead 723 when engaging cardiac tissue while also being small enough to facilitate ease of implantation. In some embodiments, height 784 may be greater than or equal to about 0.5, 1, 1.5, 2, 2.5, or 3 mm. In some embodiments, height 784 may be less than about 3, 2.5, 2, 1.5, 1, or 0.5 mm.

Protrusion 722 may have length 786 extending along, or parallel to, the nominal surface of lead 723, for example, in a longitudinal direction. In some embodiments, length 786 may be greater than or equal to about 0.5, 1, 1.5, 2, 2.5, or 3 mm. In some embodiments, length 786 may be less than or equal to about 3, 2.5, 2, 1.5, 1, or 0.5 mm.

Distal end portion 724 of lead 723 may have length 782 in any suitable range to facilitate positioning electrode assembly 761 near a His bundle or bundle branch region. In some embodiments, length 782 may be greater than or equal to about 4, 5, 6, 7, 8, 9, 10, 11, 12, 13, 14, 15, 16, 17, or 18 mm. In some embodiments, length 782 may be less than about 4, 5, 6, 7, 8, 9, 10, 11, 12, 13, 14, 15, 16, 17, or 18 mm.

Electrode assembly 761 may have length 780 extending out from an end of distal end portion 724 in any suitable range to facilitate positioning electrode assembly 761 near the His bundle or bundle branch region. Some or all of electrode assembly 761 may function as an electrode. In some embodiments, length 780 may be greater than or equal to about 0.5, 1, 1.5, 2, 2.5, 3, 3.5, 3.75, 4, or 10 mm. In some embodiments, length 780 may be less than about 0.5, 1, 1.5, 2, 2.5, 3, 3.5, 3.75, 4, or 10 mm.

In general, lengths of protrusion 722, distal end portion 724, and/or electrode assembly 761 may be selected to facilitate positioning electrode 752, electrode assembly 761, or both electrode 752 and electrode assembly 761 near the His bundle or one or both bundle branches. The various lengths may be determined, for example, based on a septum thickness. Septum thickness may be determined using an echocardiogram.

AV delay may be programmed using sensing from an atrial electrode, such as sensing from electrode 770 of FIG. 18A, which may be used only for sensing in some embodiments. The atrial electrode may be positioned, for example, about 5 to 10 cm proximal to the distal end of lead 723 or electrode assembly 761. In other words, the atrial electrode may be spaced 5 cm or more from one or both cathode electrodes. The AV delay, or time from atrial activation to bundle pacing, may be appropriately set using the atrial electrode.

One embodiment of lead implantation method may incorporate ECG and impedance guided lead placement employing the lead shown in FIG. 22A. In general, the lead may include an ECG transition during implantation that can be used to determine where the pacing lead is located. For example, the ECG QRS morphology may change, which represents a transition from an LBBB pattern or delay to an RBBB pattern or delay, as the pacing lead is used to intermittently pace during implantation from the right side of the ventricular septum to the left side. If the ECG morphology indicates the tip is near the endocardium of the ventricular septum, the lead insertion may be stopped. During the lead insertion through the septum, the pacing impedance may be monitored. If a sudden change in pacing impedance is detected (such as drop by 10-30%), the pacing lead may be pulled back by rotating the lead, for example, counterclockwise about 1-3 turns. As the left bundle branch is located beneath the endocardium, use of these two assessments can avoid the lead perforation into the LV. Once the pacing lead is in place, electrical output may be applied to one or both right and left bundle branches in a synchronized manner, which may excite the ventricles simultaneously, almost simultaneously, or using a short delay.

Synchronized pacing of one or both bundle branches may be based on an atrial event, a ventricular event, or both. In some embodiments, synchronized pacing may deliver two or more pacing pulses within the same cardiac cycle, for example, one to each ventricle.

In some embodiments, a lead including two or more pacing electrodes may be used to deliver differently paced pulses to the bundle of His or one or both bundle branches. Differently paced pulses are not delivered simultaneously or sequentially to the His bundle or bundle branch tissue. Instead, a pulse to a first tissue may be paced at a first time, and a pulse to a second tissue may be pulsed at a second time. A delay may be used between the first pulse and the second pulse.

If the lead shown in FIG. 22B is used, then echocardiography may be performed before implantation to assess the thickness of the ventricular septum. A pacing lead may be selected or chosen with an appropriate distance from electrode assembly, or distal end portion or tip of the lead, to the proximal cathode electrode. The selected pacing lead may also include a stopper to prevent perforation of the LV. Pacing output may be applied to one or both bundle branches in a synchronized manner, simultaneously (or synchronized) so both ventricles can be excited in a synchronized manner, which may excite the ventricles simultaneously, almost simultaneously, or using a short delay.

FIG. 23 is a flow diagram that shows an example of a method of lead implantation for bundle branch pacing for a leaded or leadless IMD. Method 830 may include one or more of the blocks illustrated. Method 830 may begin, for example, once the implantable medical lead makes contact with the septal wall. Method 830 may include block 832 to continuously record a 12-lead ECG and a pacing lead EGM. Method 830 may include block 834 to apply pacing from the pacing lead while analyzing ECG morphology. In some embodiments, the pacing output amplitude may be about 2 to 5 V and a pulse width duration may be about 0.5 ms.

In block 836, the lead may be inserted into the septal wall, which may include rotating the lead. In block 838, the ECG may be analyzed to determine whether an LBBB pattern is present. If the answer to block 838 is YES, method 830 may continue to block 840, whereas if the answer is NO, method 830 may continue to block 846.

In block 840, method 830 may determine that an RBB pacing location has been achieved, for example, based on detecting the LBBB pattern in block 838. In block 842, method 830 may determine whether the patient has RBBB. If the answer to block 842 is NO, then the lead may be fixed in the RBB location in block 844, whereas if the answer is YES, then the lead may continue to be rotated in block 846. For example, in block 846, the lead may advance a short distance, for example, by rotating 1-3 times in a clockwise direction.

After rotation, method 830 may determine whether the ECG shows an RBBB pattern, RBB delay pattern, or a near-normal ECG. If the answer to block 848 is NO, method 830 may continue to block 856, whereas if the answer to block 848 is YES, method 830 may continue to block 850. In block 856, method 830 may determine whether pacing lead impedance has changed greater than or equal to about 10, 20, 30, 40, 50, or 60% compared to a previously measured impedance of the pacing lead. A large change in pacing lead impedance may indicate that the lead has perforated into the LV. If the answer to block 856 is NO, method 830 may return to continuing rotation of the lead in block 846, whereas if the answer is YES, method 830 may continue to block 858.

In block 850, method 830 may determine that an LBB pacing location has been achieved, for example, based on detecting the RBBB pattern, RBB delay pattern, or near-normal ECG. In block 852, method 830 may determine whether pacing lead impedance has changed greater than or equal to about 10, 20, 30, 40, 50, or 60% compared to a previously measured impedance of the pacing lead. If the answer to block 852 is NO, the impedance change may be within a normal range, and the lead may be fixed in the LBB location in block 854, whereas if the answer is YES, method 830 may continue to block 858.

In block 858, method 830 may pull back or retract the lead a short distance, for example, by rotating 1-3 times in the counterclockwise direction. In block 860, method 830 may determine whether that the pacing impedance is in a normal range. If the answer to block 860 is YES, the lead may be fixed in block 862, whereas if the answer is NO, method 830 may return to block 858 to continue pulling back or retracting the lead a short distance.

During method 830, the IMD may memorize the pattern of LBBB or RBBB/D (e.g., RBBB or RBB delay). Post implantation, the device may adjust pacing to the LBB or RBB, for example, if LBBB or RBBB/D is detected.

FIG. 24 shows various aspects of one example of LPD 916 for His bundle or bundle pacing, which may be similar to LPD 616 (FIG. 16), except instead of a helical electrode assembly, LPD 916 may include a relatively straight, needle-like, or dart-type electrode assembly 961 for piercing tissue. In other embodiments, electrode assembly 961 may be a screw or helix-type. Electrode assembly 961 may be described as a cathode electrode for pacing on the left side of the patient's septum. LPD 916 may include electrode 952, which may be described as a cathode electrode for pacing on the right side of the patient's septum. LPD 916 may include an electrode 970, which may be described as an anode electrode.

LPD 916 may include fixation elements 962 that are different, separate, or independent from electrode assembly 961. Fixation elements 962 may attach LPD 916 to cardiac tissue. Fixation elements 962 may include any suitable mechanisms, such as active fixation tines, screws, clamps, adhesive members, or any other types of attaching a device to tissue. As shown, fixation elements 962 may be constructed of a memory material that retains a preformed shape. During implantation, fixation elements 962 may be flexed forward to pierce tissue and allowed to flex back towards a case of housing of LPD 916. In this manner, fixation elements 962 may be embedded within the target tissue.

FIGS. 25-27 show various locations to position electrode 952. FIG. 25 shows electrode 952 as a ring electrode around electrode assembly 961. FIG. 26 shows electrode 952 as a discrete contact adjacent to electrode assembly 961. FIG. 27 shows electrode 952 as multiple discrete contacts adjacent to electrode assembly 961, such as two discrete contacts on opposite sides of electrode assembly 961. Electrode 952 may be described as leadlessly coupled to the housing. Electrode assembly 961 may also be described as being, or including, an electrode leadlessly coupled to a piercing element.

FIGS. 28A-B show a lead, such as implantable medical lead 723 (FIG. 22B), having a lead connector 790 with contacts 753, 762 operably coupled to cathode electrodes on lead 723. IMD 716 may be configured to receive lead connector 790 in a lead connector receptacle. One example of IMD 716 includes a Medtronic ADAPTAT™ MRI SureScan. When inserted, contacts 753, 762 may operably couple to cathode connections 793, 792 of IMD 716, respectively, for sensing or electrical pulse delivery.

FIGS. 29-31 show various methods for updating pacing configurations based on ECG and/or EGM information. In general, if measured AV interval prolongation is detected, the methods may shorten AV pacing intervals until measured AV interval prolongation is corrected. Output pacing amplitude may be adjusted, for example, if AV pacing intervals adjustment cannot correct the prolongation. Further, in general, if an LBBB pattern or LBB delay is detected, AV pacing intervals and/or pacing output amplitude may be adjusted in a similar manner.

In some embodiments, upon detecting dyssynchrony during a patient's intrinsic rhythm or during pacing, delivery of His-bundle or bundle-branch stimulation pulses may be adjusted based on the dyssynchrony detected. RV-LV dyssynchrony, such as an LBB or RBB delay or LBBB or RBBB pattern, may be the result of one bundle branch not being activated by bundle pacing. Increasing pacing output may reactivate both bundle branches at an appropriate AV interval. In some embodiments, if an RBB delay or RBBB pattern is detected, pacing output amplitude may be adjusted.

FIG. 29 shows one example of method 1001 for updating a current pacing configuration when an ECG changes post implantation in block 1012 after achieving normal AV conduction in an ECG upon implantation in block 1010. Upon detecting a change in an ECG post implantation, method 1001 may determine whether an EGM is normal in block 1014. If the EGM is normal, method 1001 may continue to block 1016. Otherwise, if the EGM is abnormal, method 1001 may continue to block 1030.

In block 1016, method 1001 may determine whether a measured AV interval is prolongated. If NO, method 1001 may continue to block 1018 to take no action to change the current pacing configuration. If YES, method 1001 may continue to block 1020 to shorten an AV pacing interval.

In block 1022, method 1001 may determine whether a measured AV interval shows correction in response to the shortened AV pacing interval. If YES, method 1001 may continue to block 1024 to update the pacing configuration based on the corresponding shortened AV pacing interval. If NO, method 1001 may continue to block 1026.

In block 1026, method 1001 may determine whether adjustments to the AV pacing interval have been exhausted. If NO, method 1001 may return to block 1020 to continue shortening the AV pacing interval, for example, in an iterative manner. If YES, method 1001 may continue to block 1028 to increase a pacing output amplitude (e.g., voltage) until the measured AV interval is corrected or output pacing adjustments have been exhausted, upon which method 1001 may continue to block 1024 to update the pacing configuration after correcting or exhausting the pacing output adjustments based on, for example, an optimal AV pacing interval and/or optimal pacing output.

In block 1030, after determining that an EGM is not normal in block 1014, method 1001 may determine whether an RBB or LBB delay is represented in the EGM. If there is an LBB delay, method 1001 may continue to block 1034, whereas if there is an RBB delay, method 1001 may continue to block 1042.

In block 1034, method 1001 may determine that only the RBB is being paced by the implanted IMD. In block 1036, pacing timing may be adjusted such that RBB pacing may be delayed (e.g., later) or LV pacing may be advanced (e.g., earlier). Method 1001 may continue to determine whether RV-LV dyssynchrony has been corrected in block 1038. If YES, method 1001 may continue to block 1024 to update the pacing configuration. If NO, method 1001 may continue to block 1040.

In block 1040, method 1001 may determine whether adjustments to RBB pacing or LV pacing timing have been exhausted. If NO, method 1001 may return to block 1036 to continue adjusting pacing timing, for example, in an iterative manner. If YES, method 1001 may continue to block 1028 to increase pacing output amplitude (e.g., voltage) until RV-LV dyssynchrony is corrected or output pacing adjustments have been exhausted. Method 1001 may continue to block 1024 to update the pacing configuration based on, for example, an optimal AV pacing interval and/or optimal pacing output.

In block 1042, method 1001 may determine that only the LBB is being paced by the implanted IMD. In block 1044, pacing timing may be adjusted such that LBB pacing may be delayed (e.g., later) or RV pacing may be advanced (e.g., earlier). Method 1001 may continue to determine whether RV-LV dyssynchrony has been corrected in block 1046. If YES, method may continue to block 1024 to update the pacing configuration. If NO, method 1001 may continue to block 1048.

In block 1048, method 1001 may determine whether adjustments to LBB pacing or RV pacing timing have been exhausted. If NO, method 1001 may return to block 1044 to continue adjusting pacing timing, for example, in an iterative manner. If YES, method 1001 may continue to block 1028 to increase pacing output amplitude (e.g., voltage) until RV-LV dyssynchrony is corrected or output pacing adjustments have been exhausted. Method 1001 may continue to block 1024 to update the pacing configuration after correcting or exhausting the pacing output adjustments based on, for example, an optimal AV pacing interval and/or optimal pacing output.

FIG. 30 shows one example of method 1002 for updating a current pacing configuration when an ECG changes post implantation in block 1052 after achieving correction of an abnormal LBBB ECG upon implantation in block 1050. Upon detecting a change in ECG post implantation, method 1002 may determine whether an EGM is normal in block 1054. If the EGM is normal, method 1002 may continue to block 1056. Otherwise, if the EGM is abnormal, method 1002 may continue to block 1068.

In block 1056, method 1002 may determine whether a measured AV interval is prolonged. If NO, method 1002 may continue to block 1058 to take no action to change the current pacing configuration. If YES, method 1002 may continue to block 1060 to shorten an AV pacing interval.

In block 1062, method 1002 may determine whether a measured AV interval shows correction in response to the shortened AV pacing interval. If YES, method 1002 may continue to block 1064 to update the pacing configuration based on the corresponding shortened AV pacing interval. If NO, method 1002 may continue to block 1066.

In block 1066, method 1002 may determine whether adjustments to the AV pacing interval have been exhausted. If NO, method 1002 may return to block 1060 to continue shortening the AV pacing interval, for example, in an iterative manner. If YES, method 1002 may continue to update pacing configuration in block 1064 based on, for example, an optimal AV pacing interval and/or optimal pacing output.

In block 1068, after determining that an EGM is not normal in block 1054, method 1002 may determine whether an RBB or LBB delay is represented in the EGM. If there is an LBB delay, method 1002 may continue to block 1070, whereas if there is an RBB delay, method 1002 may continue to block 1078.

In block 1070, method 1002 may determine that LBBB has returned. In block 1072, pacing output amplitude (e.g., voltage) may be increased. In block 1074, method 1002 may determine whether LBBB has been corrected in response to the increased pacing output. If YES, method 1002 may continue to block 1064. If NO, method 1002 may continue to block 1076.

In block 1076, method 1002 may determine whether pacing output adjustments have been exhausted. If YES, method 1002 may continue to block 1064 to update the pacing configuration based on, for example, an optimal AV pacing interval and/or optimal pacing output. If NO, method 1002 may return to block 1072 to continue increasing pacing output, for example, in an iterative manner.

In block 1078, after determining that an RBB delay is represented in the EGM in block 1068, method 1002 may determine that an RBBB pattern or RBB delay has been detected. In block 1080, method 1002 may shorten an AV pacing interval. Method 1002 may determine whether the RBBB pattern or RBB delay has been corrected in response to shortening the AV pacing interval in block 1082. If YES, method 1002 may continue to block 1064 to update the pacing configuration based on, for example, the optimal AV pacing interval and/or optimal pacing output. If NO, method 1002 may continue to block 1084.

In block 1084, method 1002 may determine whether AV pacing interval adjustments have been exhausted. If NO, method 1002 may return to block 1080 to continue shortening the AV pacing interval, for example, in an iterative manner. If YES, method 1002 may continue to block 1086 to increase pacing output until the RBBB pattern or RBB has been corrected or output pacing adjustments have been exhausted. Method 1002 may continue to block 1064 to update the pacing configuration based on, for example, an optimal AV pacing interval and/or optimal pacing output.

FIG. 31 shows one example of method 1003 for updating a current pacing configuration when an ECG changes in block 1104 after implanting an IMD for LBB or dual bundle branch pacing in 1102. Method 1003 may include determining whether an RBBB or LBBB pattern is represented in an EGM. If an RBBB pattern is represented, method 1003 may continue to block 1108. If an LBBB pattern is represented, method 1003 may continue to block 1118.

In block 1108, method 1003 may adjust an AV pacing interval. In block 1110, method 1003 may determine whether the RBBB pattern has been corrected in response to adjusting the AV pacing interval. If YES, method 1003 may continue to block 1112 to update the pacing configuration based on, for example, an optimal AV pacing interval and/or optimal pacing output. If NO, method 1003 may continue to block 1114.

In block 1114, method 1003 may determine whether AV pacing interval adjustments have been exhausted. If NO, method 1003 may return to block 1108 to adjust AV pacing interval, for example, in an iterative manner. If YES, method 1003 may continue to block 1116 to increase pacing output until the RBBB pattern is corrected or AV pacing interval adjustments have been exhausted. Method 1003 may continue to block 112 to update the current pacing configuration based on, for example, an optimal AV pacing interval and/or an optimal pacing output.

In block 1118, after determining that an LBBB pattern is represented in block 1106, method 1003 may increase pacing output amplitude (e.g., voltage). Method 1003 may determine whether the LBBB pattern has been corrected in block 1120. If YES, method 1003 may continue to block 1112. If NO, method may continue to block 1122.

In block 1122, method 1003 may determine whether pacing output adjustments have been exhausted. If NO, method 1003 may return to block 1118 to continue increasing pacing output, for example, in an iterative manner. If YES, method 1003 may continue to block 1112 to update the pacing configuration based on, for example, an optimal AV pacing interval and/or an optimal pacing output.

Various examples have been described. These and other examples are within the scope of the following claims. For example, a single chamber, dual chamber, or triple chamber pacemakers (e.g., CRT-P) or ICDs (e.g., CRT-D) devices can be used to implement the illustrative methods described herein.

ILLUSTRATIVE EMBODIMENTS

While the present disclosure is not so limited, an appreciation of various aspects of the disclosure will be gained through a discussion of the specific illustrative embodiments provided below, which provide alloys with superior mechanical and corrosion properties. Various modifications of the illustrative embodiments, as well as additional embodiments of the disclosure, will become apparent herein.

Embodiment A1 is a method of using a pacemaker for His-bundle or bundle-branch pacing of a patient's heart comprising sensing heart activity using a set of electrodes associated with the pacemaker; using a processor in the pacemaker to determine whether one of a QRS parameter and an activation interval acquired from the sensed heart activity is greater than a first threshold; in response to determining whether the QRS parameter or activation interval is greater than the first threshold, using the processor to determine whether bundle pacing should be delivered earlier or later; and in response to determining whether bundle pacing should be delivered earlier or later, using the processor to adjust a time interval for bundle pacing.

Embodiment A2 is a method of any A embodiment, wherein using the processor to determine whether bundle pacing should be delivered earlier or later comprises determining whether a bundle-pacing to ventricular-activation interval reaches a second threshold.

Embodiment A3 is a method of any A embodiment, wherein using the processor to adjust the time interval for bundle pacing comprises adjusting an atrial-activation to bundle-pacing interval or adjusting a bundle-pacing to left- or right-ventricular-activation interval.

Embodiment A4 is a method of any A embodiment, wherein the sensed heart activity comprises one or more of: an intraventricular interval, a QRS duration, a QRS morphology, a QRS vector, an R-wave timing, a bundle-pacing to left- or right-ventricular-activation interval, and an atrial-sensing to left- or right-ventricular-activation interval.

Embodiment A5 is a method of any A embodiment, wherein the processor is contained in a housing of the pacemaker.

Embodiment A6 is a method of any A embodiment, further comprising: using the processor to determine whether another QRS parameter acquired from the sensed heart activity is greater than the first threshold; and in response to determining that the another QRS parameter is greater than or equal to the first threshold, using the processor to determine whether the another QRS parameter is greater than the QRS parameter.

Embodiment A7 is a method of embodiment A6, further comprising: in response to determining that the another QRS parameter is greater than the QRS parameter, using the processor to increase a bundle pacing output level.

Embodiment A8 is a method of embodiment A7, further comprising: using the processor to determine whether yet another QRS parameter acquired from the sensed heart activity is greater than the first threshold; and in response to determining that the yet another QRS parameter is greater than the another QRS parameter, using the processor to select an optimal time interval or an optimal pacing output level for bundle pacing corresponding to a minimal QRS parameter.

Embodiment A9 is a method of any A embodiment, wherein the first threshold is equal to or less than 130 ms.

Embodiment A10 is a method of any A embodiment, wherein the time interval for bundle pacing is adjusted by increasing up to 10 ms or decreasing down to 10 ms.

Embodiment A11 is a method of using an implantable medical device having a processor and an electrical pulse generator comprising: using the processor to control the electrical pulse generator to adjust delivery of bundle pacing. The processor is configured to: measure a QRS parameter and determine whether the QRS parameter is larger than a threshold; in response to determining that the QRS parameter is greater than or equal to the threshold, adjust a bundle-pacing to ventricular-activation interval or a bundle pacing output level; and deliver bundle pacing using the adjusted bundle-pacing to ventricular-activation interval or using the adjusted bundle pacing output level.

Embodiment A12 is an implantable medical device for His-bundle or bundle-branch pacing of a patient's heart comprising: a sensing circuit configured to sense an atrial event (As) and a ventricular event (Vs); an electrical pulse generator configured to generate and deliver electrical His-bundle or bundle-branch stimulation pulses (Vp); a processor coupled to the sensing circuit and the electrical pulse generator and configured to control the electrical pulse generator to deliver said Vp on expiration of a defined AV interval or Vp-Vs interval following a said As or Vs. The processor is further configured to: determine whether Vp timing should be adjusted; in response to determining that the Vp timing should be adjusted, determine whether Vp should be delivered earlier or later; in response to determining whether the Vp should be delivered earlier or later, decrease an AV delay if the Vp should be delivered earlier or increase the AV delay in response to determining Vp should be delivered later; generate a set of AV delays that are stored in memory based on iterating through decreases or increases in the AV delay; select an optimal AV delay from the set of AV delays stored in memory; and use the optimal AV delay when delivering His-bundle or bundle-branch pacing.

Embodiment A13 is a device of any A embodiment, wherein the processor is further configured to: in response to determining that the Vp timing should be adjusted, advance or delay Vp in response to whether Vp should be delivered earlier or later to adjust Vp timing.

Embodiment A14 is a device of any A embodiment, wherein the processor is further configured to determine whether Vp timing should be adjusted based on dyssynchrony.

Embodiment A15 is a device of embodiment A14, wherein the processor is further configured to detect dyssynchrony using one or both of: a comparison of a Vp to RV-sensing interval with a Vp to LV-sensing interval, and a QRS morphology change.

Embodiment A16 is a device of embodiment A15, wherein to detect dyssynchrony using a QRS morphology change comprises comparing a current QRS morphology to a predetermined QRS morphology representative of an RBBB or LBBB pattern.

Embodiment A17 is a device of any of embodiments A14 to A16, wherein the processor is further configured to: in response to determining that the Vp timing should be adjusted using dyssynchrony, determining that the Vp output should be adjusted.

Embodiment A18 is a device of any A embodiment, wherein to determine whether Vp timing should be adjusted is based on one or more criteria comprising one or both of a QRS parameter and an activation interval.

Embodiment A19 is a device of embodiment A18, wherein the criterion comprises one or more of: a QRS duration, a QRS morphology change, a QRS vector change, an RBBB pattern, an LBBB pattern, and a bundle-pacing to RV- or LV-activation interval.

Embodiment A20 is a device of embodiment A18 or A19, wherein to determine whether the Vp timing should be adjusted is based on a QRS parameter being greater than a threshold.

Embodiment A21 is a device of any A embodiment, wherein the implantable medical device comprises one or more of: a pacemaker with a medical lead, an implantable cardioverter-defibrillator (ICD), an intracardiac device, a leadless pacing device (LPD), a subcutaneous ICD, and a subcutaneous medical device.

Embodiment A22 is a device of any A embodiment, wherein the implantable medical device comprises a triple chamber device, a dual chamber device, or a single chamber device.

Embodiment A23 is a device of embodiment A22, wherein the single chamber device only employs a bundle pacing lead.

Embodiment A24 is a device of embodiment A22 or A23, wherein the dual chamber device requires at least a bundle pacing lead disposed in the His bundle or bundle branch region and another lead in one of the right ventricle, left ventricle, or right atrium.

Embodiment A25 is a device of any of embodiments A22 to A24, further comprising: a housing for containing the sensing circuit, the electrical pulse generator, and the processor; and a connector interface coupled to the housing, the connector interface comprising a set of ports for receiving a set of leads. The set of ports includes: a right atrial port for receiving a right atrial lead, and a left ventricular port for receiving a left ventricular lead, wherein the bundle pacing lead is configured to be coupled to the right ventricular port.

Embodiment A26 is a device of embodiment A25, wherein when the patient is experiencing atrial fibrillation, the bundle pacing lead is inserted through the device right atrial port, the right ventricular lead is inserted through the device right ventricular port, and the left ventricular lead is inserted through the device left ventricular port.

Embodiment A27 is a device of embodiment A25 or A26, wherein when a patient is not experiencing atrial fibrillation, the bundle pacing lead is inserted through either the right or left ventricular port of the device, and the right or left ventricular lead is inserted through the other of the right or left ventricular port of the device.

Embodiment A28 is a device of any of embodiments A25 to A27, wherein the right atrial port is configured to receive a Y-adaptor, the Y-adaptor configured to receive connections to the tip and ring electrodes of the bundle pacing lead.

Embodiment A29 is a device of embodiment A28, wherein the right ventricular lead is inserted through the right ventricular port of the device and the left ventricular lead is inserted through the left ventricular port of the device.

Embodiment A30 is a device of any of embodiments A25 to A29, further comprising at least two electrodes on the housing.

Embodiment A31 is a device of embodiment A30, wherein the implantable medical device comprises an intracardiac device.

Embodiment A32 is an implantable medical device for His-bundle or bundle-branch pacing of a patient's heart comprising: a sensing circuit configured to sense an atrial event (As) and a ventricular event (Vs); an electrical pulse generator configured to generate and deliver electrical His-bundle or bundle-branch stimulation pulses (Vp); a processor coupled to the sensing circuit and the electrical pulse generator and configured to control the electrical pulse generator to deliver said Vp on expiration of a defined AV interval or Vp-Vs interval following a said As or Vs. The processor is further configured to: determine whether RV activation occurs earlier than LV activation; and in response to determining RV activation occurs earlier than LV activation, adjust Vp timing to deliver His-bundle or bundle-branch pacing based on an LV activation time.

Embodiment A33 is an implantable medical device for His-bundle or bundle-branch pacing of a patient's heart comprising: a sensing circuit configured to sense an atrial event (As) and a ventricular event (Vs); an electrical pulse generator configured to generate and deliver electrical His-bundle or bundle-branch stimulation pulses (Vp); and a processor coupled to the sensing circuit and the electrical pulse generator and configured to control the electrical pulse generator to deliver said Vp on expiration of a defined AV interval or Vp-Vs interval following a said As or Vs. The processor is further configured to: determine whether RV activation occurs earlier than LV activation; in response to determining that RV activation does not occur earlier than LV activation, determine whether RV activation occurs later than LV activation; and in response to determining RV activation occurs later than LV activation, adjust Vp timing to deliver His-bundle or bundle-branch pacing based on an RV activation time.

Embodiment A34 is a method of using a pacemaker for His-bundle or bundle-branch pacing of a patient's heart comprising: sensing electrical activity of the patient's heart including an atrial event (As) and a ventricular event (Vs); detecting dyssynchrony based on the sensed electrical activity of the patient's heart during the patient's intrinsic rhythm or during pacing; and adjusting delivery of His-bundle or bundle-branch stimulation pulses (Vp) based on the dyssynchrony detected.

Embodiment A35 is a method of any A embodiment, further comprising: in response to detecting dyssynchrony in the sensed electrical activity, determining whether the sensed electrical activity represents a right bundle branch (RBB) delay, and in response to determining that the sensed electrical activity represents an RBB delay, delivering Vp to the left bundle branch (LBB) of the patient's heart earlier or deliver right ventricular (RV) pacing earlier.

Embodiment A36 is a method of any A embodiment, further comprising: in response to detecting dyssynchrony in the sensed electrical activity, determining whether the sensed electrical activity represents a right bundle branch (RBB) delay; and in response to determining that the sensed electrical activity does not represent an RBB delay, delivering Vp to the right bundle branch (RBB) of the patient's heart earlier or delivering left ventricular (LV) pacing earlier.

Embodiment A37 is a method of any A embodiment, further comprising: in response to detecting dyssynchrony in the sensed electrical activity, determining whether the sensed electrical activity represents a right bundle branch (RBB) delay; and in response to determining that the sensed electrical activity represents an RBB delay, adjusting an As-Vp interval.

Embodiment A38 is a method of any of embodiments A34 to A37, further comprising: in response to detecting dyssynchrony in the sensed electrical activity, determining whether the sensed electrical activity represents a right bundle branch (RBB) delay; and in response to determining that the sensed electrical activity does not represent an RBB delay, increasing Vp output.

Embodiment A39 is a method of using a pacemaker for His-bundle or bundle-branch pacing of a patient's heart comprising sensing electrical activity of the patient's heart including an atrial event (As) and a ventricular event (Vs); detecting a right bundle branch block (RBBB) pattern or left bundle branch block (LBBB) pattern in the sensed electrical activity of the patient's heart during the patient's intrinsic rhythm or during pacing; and adjusting the delivery of His-bundle or bundle-branch stimulation pulses (Vp) based on the detected bundle-branch-block pattern.

Embodiment A40 is a method of any A embodiment, further comprising in response to detecting an RBBB pattern in the sensed electrical activity, adjusting an As-Vp interval.

Embodiment A41 is a method of any A embodiment, further comprising in response to detecting an LBBB pattern in the sensed electrical activity, increasing Vp output.

Embodiment B1 is an implantable medical device for bundle-branch pacing of a patient's heart comprising a plurality of electrodes. The plurality of electrodes a left bundle branch (LBB) cathode electrode positionable, when implanted, on a left side of the septum of the patient's heart proximate to the LBB, and a right bundle branch (RBB) cathode electrode positionable, when implanted, implantable on a right side of the septum of the patient's heart proximate to the RBB. The device includes an electrical pulse generating circuit coupled to the plurality of electrodes to generate and deliver electrical bundle-branch stimulation pulses (Vp); and a processor coupled to the electrical pulse generating circuit, the processor configured to control the electrical pulse generating circuit to deliver synchronized left and right bundle-branch Vp using the plurality of electrodes based on one or both of an atrial event (As) and a ventricular event (Vs).

Embodiment B2 is a device of any B embodiment, further comprising a sensing circuit operably coupled to the processor and the plurality of electrodes to sense electrical activity of the patient's heart including As or Vs using at least one of the plurality of electrodes.

Embodiment B3 is a device of any B embodiment, wherein the LBB cathode electrode does not pierce or extend into the left ventricle.

Embodiment B4 is a device of any B embodiment, wherein the synchronized left and right bundle-branch Vp are delivered simultaneously.

Embodiment B5 is a device of any B embodiment, wherein the synchronized left and right bundle-branch Vp are delivered sequentially or with a delay between the left bundle-branch Vp and the right bundle-branch Vp.

Embodiment B6 is a device of any B embodiment, further comprising a medical electrical lead to deliver Vp, the medical electrical lead comprising a lead body, the plurality of electrodes disposed on the lead body to deliver pacing pulses within a single cardiac cycle.

Embodiment B7 is a device of embodiment B6, wherein the lead body comprises a shaft extending longitudinally and a stopper protruding radially outward from the shaft configured to prevent the left bundle-branch electrode from perforating into the left ventricle.

Embodiment B8 is a device of embodiment B6 or B7, wherein the plurality of electrodes comprises an atrial electrode coupled to the lead body and implantable in the patient's heart to sense As.

Embodiment B9 is a device of embodiment B8, wherein the atrial electrode is spaced at least 5 cm from one of the bundle-branch cathode electrodes.

Embodiment B10 is a device of any B embodiment, wherein the implantable medical device is a leadless pacing device (LPD) comprising a housing and at least one of the plurality of electrodes is leadlessly connected to the housing.

Embodiment B11 is a device of embodiment B10, wherein the at least one electrode leadlessly connected to the housing is in the shape of a ring electrode.

Embodiment B12 is a device of any B embodiment, wherein the implantable medical device is a leadless pacing device (LPD) comprising a housing and at least one of the plurality of electrodes is leadlessly connected to a piercing element extending axially from the housing.

Embodiment B13 is a device of embodiment B12, further comprising a fixation element different than the piercing element extending axially from the housing.

Embodiment B14 is a method of using a pacemaker for bundle-branch pacing of a patient's heart comprising: sensing electrical activity of the patient's heart including an atrial event (As) and a ventricular event (Vs); and delivering synchronized left and right bundle-branch stimulation pulses (Vp) using left and right bundle-branch cathode electrodes based on one or both of As and Vs, wherein the left bundle branch (LBB) cathode electrode is implantable on a left side of the septum of the patient's heart proximate to the LBB of the patient's heart, wherein the right bundle branch (RBB) cathode electrode is implantable on a right side of the septum of the patient's heart proximate to the RBB.

Embodiment B15 is a method of positioning a bundle pacing electrode in a patient's heart comprising: monitoring electrical activity of the patient's heart using one or both of an external electrode and a bundle pacing electrode on a bundle pacing lead or leadless device; rotating or advancing the bundle pacing lead or leadless device toward the His bundle or bundle branch of the patient's heart while intermittently applying pacing with the bundle pacing electrode; determining whether an RBBB pattern is present based on the monitored electrical activity; determining whether the patient's heart has a right bundle branch block (RBBB); and in response to determining that an RBBB pattern is present during applied pacing and that the patient's heart does not have a RBBB, fixing the bundle pacing lead or leadless device for left bundle branch pacing.

Embodiment B16 is a method of any B embodiment, further comprising in response to determining that an LBBB pattern is present and the patient's heart has a RBBB, continuing to rotate or advance the bundle pacing lead or leadless device toward the left bundle branch of the patient's heart.

Embodiment B17 is a method of embodiment B16, further comprising: in response to continuing to rotate or advance the bundle pacing lead or leadless device, determining whether the monitored electrical activity represents an RBBB pattern, RBB delay, or near-normal electrocardiogram (ECG); and in response to determining that an RBBB pattern, RBB delay, or near-normal ECG is present, fixing the bundle pacing lead or leadless device.

Embodiment B18 is a method of embodiment B17, further comprising: determining whether an impedance change of the bundle pacing electrode falls below a threshold; in response to determining that the impedance change of the bundle pacing electrode does not fall below a threshold, continuing to rotate or advance the bundle pacing lead or leadless device or fixing the bundle pacing lead or leadless device; and in response to determining that the impedance change of the bundle pacing electrode does fall below the threshold, reversing rotation or advancement of the bundle pacing lead or leadless device.

Embodiment B19 is a method of embodiment B18, wherein the threshold is less than 50% of a previously measured impedance of the bundle pacing electrode.

Embodiment B20 is a method of embodiment B18 or B19, further comprising fixing the bundle pacing lead or leadless device in response to an impedance of the bundle pacing electrode being within a normal range.

Embodiment C1 is a leadless pacing device (LPD) for His-bundle or bundle-branch pacing in a patient's heart comprising: an intracardiac housing; a plurality of electrodes comprising a bundle pacing electrode leadlessly connected to the housing and implantable proximate to or in the His bundle or bundle branch of the patient's heart; a sensing circuit operably coupled to the plurality of electrodes and configured to sense one or both of an atrial event (As) and a ventricular event (Vs) using at least one of the plurality of electrodes; and an electrical pulse generator coupled to the bundle pacing electrode, the electrical pulse generator configured to generate and deliver electrical His-bundle or bundle-branch stimulation pulses (Vp) based on one or both of As and Vs to the patient's heart using the bundle pacing electrode.

Embodiment C2 is a device of any C embodiment, further comprising a processor coupled to the sensing circuit and the electrical pulse generator, the processor configured to adjust a time interval or a pacing output level for His-bundle or bundle-branch pacing based on one or both of As and Vs sensed by the sensing circuit.

Embodiment C3 is a device of any C embodiment, wherein when the plurality of electrodes is positioned proximate to the His bundle or bundle branch, wherein the plurality of electrodes is configured to not pierce or extend into the left ventricle.

Embodiment C4 is a device of any C embodiment, wherein the plurality of electrodes comprises an atrial cathode electrode leadlessly connected to the housing and implantable in the patient's heart to sense As.

Embodiment C5 is a device of any C embodiment, wherein the bundle pacing electrode is leadlessly connected to a piercing element extending axially from the housing.

Embodiment C6 is a device of embodiment C5, wherein the piercing element is also configured as a fixation element.

Embodiment C7 is a device of embodiment C5 or C6, further comprising a fixation element different than the piercing element extending axially from the housing.

Embodiment C8 is a leadless pacing device (LPD) for His-bundle or bundle-branch pacing in a patient's heart comprising: an intracardiac housing; a communication interface disposed in the housing configured to receive signals from a subcutaneously implanted device (SD); and a controller disposed in the housing operatively coupled to at least one electrode configured to deliver His-bundle or bundle-branch pacing pulses to the patient's heart in response to the received signals.

Embodiment C9 is an LPD of any C embodiment, wherein the controller is further configured to deliver His-bundle or bundle-branch pacing pulses adapted to achieve synchrony of the patient's heart in a manner manifested in a plurality of far-field electrical signals as: a narrowed QRS duration, or a correction of left branch bundle block (LBBB) or right branch bundle block (RBBB) patterns in QRS morphology.

Embodiment C10 is an LPD of any C embodiment, wherein the controller is further configured to adapt His-bundle or bundle-branch pacing pulse timing or pacing output level based on a detected A-V dyssynchrony.

Embodiment C11 is an LPD of any C embodiment, wherein the controller is further configured to adapt His-bundle or bundle-branch pacing pulse timing or pacing output level based on a detected V-V dyssynchrony.

Embodiment C12 is an LPD of any C embodiment, wherein the controller is further configured to adapt His-bundle or bundle-branch pacing pulse timing or pacing output level based on dyssynchrony detected by the SD.

Embodiment C13 is an LPD of any C embodiment, further comprising the SD, wherein the SD is configured to deliver electrical pulses to cardiac tissue, the electrical pulses being related to a different therapy than therapy provided by the LPD.

Embodiment C14 is an LPD of embodiment C13, wherein the different therapy comprises cardiac resynchronization therapy.

Embodiment C15 is an LPD of any C embodiment, wherein a subcutaneous electrode associated with the SD is employed to sense electrical signals from the patient's heart to determine the timings of atrial and ventricular activations.

Embodiment C16 is an LPD of any C embodiment, wherein the at least one electrode of the LPD is positioned within 10 mm of the His bundle or left bundle branch of the patient's heart.

Embodiment C17 is an LPD of any C embodiment, wherein the LPD comprises an elongated helical tip to extend proximate to the His bundle or bundle branch.

Embodiment C18 is an LPD of any C embodiment, wherein the LPD comprises an elongated needle to extend near the His bundle or bundle branch.

Embodiment C19 is an LPD of any C embodiment, wherein the LPD comprises a fixation element to attach the LPD to the patient's heart.

Embodiment C20 is an LPD of any C embodiment, wherein the LPD comprises a medical electrical lead, the lead comprising a stopper to prevent the at least one electrode of the LPD from perforating into the left ventricle of the patient's heart.

Embodiment C21 is a method of His-bundle or bundle-branch pacing comprising: using a subcutaneously implanted device (SD) to sense far-field electrical signals; determining a QRS parameter or activation based on the far-field electrical signals; and communicating a timing to a leadless pacing device (LPD) to deliver His-bundle or bundle-branch pacing using an atrial-activation to bundle-pacing interval.

Thus, various embodiments of BUNDLE BRANCH PACING DEVICES AND METHODS are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a mobile user device may be operatively coupled to a cellular network transmit data to or receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

The invention claimed is:

1. An implantable medical device for bundle-branch pacing of a patient's heart, the device comprising:
   a plurality of electrodes comprising:
      a left bundle branch (LBB) cathode electrode positionable, when implanted, on a left side of a septum of the patient's heart proximate to the LBB, and
      a right bundle branch (RBB) cathode electrode positionable, when implanted, on a right side of the septum of the patient's heart proximate to the RBB;
   an electrical pulse generating circuit coupled to the plurality of electrodes to generate and deliver electrical bundle-branch stimulation pulses (Vp); and
   a processor coupled to the electrical pulse generating circuit, the processor configured to:
      sense heart activity using the plurality of electrodes;
      control the electrical pulse generating circuit to deliver synchronized left and right bundle-branch stimulation pulses (Vp) using the plurality of electrodes based on one or both of an atrial event (As) and a ventricular event (Vs) of the sensed heart activity and based on an interventricular (VV) delay; and
      adjust the VV delay based on the sensed heart activity, wherein the sensed heart activity comprises sensed activations of the patient's left (LV) and right (RV) ventricles following delivery of the left and right bundle-branch stimulation pulses (Vp); and
      wherein the processor is further configured to determine whether the sensed RV activation occurs earlier than the sensed LV activation and wherein adjusting the VV delay comprises:
         adjusting the VV delay in response to the sensed RV activation occurring earlier than the LV activation.

2. The device of claim 1, further comprising a sensing circuit operably coupled to the processor and the plurality of electrodes to sense electrical activity of the patient's heart including As or Vs using at least one of the plurality of electrodes.

3. The device of claim 1, wherein the LBB cathode electrode does not pierce or extend into the left ventricle.

4. The device of claim 1, wherein the synchronized left and right bundle-branch Vp are delivered simultaneously.

5. The device of claim 1, wherein the synchronized left and right bundle-branch Vp are delivered sequentially or with a delay between the left bundle-branch Vp and the right bundle-branch Vp.

6. The device of claim 1, further comprising a medical electrical lead to deliver Vp, the medical electrical lead comprising a lead body, the plurality of electrodes disposed on the lead body to deliver pacing pulses within a single cardiac cycle.

7. The device of claim 6, wherein the lead body comprises a shaft extending longitudinally and a stopper protruding radially outward from the shaft configured to prevent the left bundle-branch electrode from perforating into the left ventricle.

8. The device of claim 6, wherein the plurality of electrodes comprises an atrial electrode coupled to the lead body and implantable in the patient's heart to sense As.

9. The device of claim 8, wherein the atrial electrode is spaced at least 5 cm from one of the bundle-branch cathode electrodes.

10. The device of claim 1, wherein the implantable medical device is a leadless pacing device (LPD) comprising a housing and at least one of the plurality of electrodes is leadlessly connected to the housing.

11. The device of claim 10, wherein the at least one electrode leadlessly connected to the housing is in the shape of a ring electrode.

12. The device of claim 1, wherein the implantable medical device is a leadless pacing device (LPD) comprising a housing and at least one of the plurality of electrodes is leadlessly connected to a piercing element extending axially from the housing.

13. The device of claim 12, further comprising a fixation element different than the piercing element extending axially from the housing.

14. The device of claim 1, wherein adjusting the VV delay in response to the sensed RV activation occurring earlier than the sensed LV activation comprises adjusting the VV delay to stimulate the left bundle branch at a time earlier relative to stimulation of the right bundle branch than prior to adjustment.

15. The device of claim 1, wherein the processor is further configured to:
   determine whether the adjusted VV delay results in an interval between a subsequent sensed RV activation and a subsequent sensed LV activation meeting a predetermined interval criterion; and
   further adjust the VV delay in response to the adjusted VV delay not resulting in the interval between the subsequent sensed RV activation and the subsequent sensed LV activation not meeting the predetermined interval criterion.

16. The device of claim 15, wherein the interval criterion comprises a predetermined maximum interval duration.

17. The device of claim 15, wherein the interval criterion comprises a predetermined optimal interval duration.

18. A method of using a pacemaker for bundle-branch pacing of a patient's heart, the method comprising:
   sensing electrical activity of the patient's heart including an atrial event (As) and a ventricular event (Vs);
   delivering synchronized left and right bundle-branch stimulation pulses (Vp) using left and right bundle-branch cathode electrodes based on one or both of As and Vs and based on an interventricular (VV) delay, wherein the left bundle branch (LBB) cathode electrode is implantable on a left side of the septum of the patient's heart proximate to the LBB of the patient's heart, wherein the right bundle branch (RBB) cathode electrode is implantable on a right side of the septum of the patient's heart proximate to the RBB; and
   adjusting the VV delay based on the sensed electrical activity of the patient's heart wherein the sensed electrical activity comprises sensed activations of the patient's left (LV) and right (RV) ventricles following delivery of the left and right bundle-branch stimulation pulses (Vp); and determining whether the sensed RV activation occurs earlier than the sensed LV activation and wherein adjusting the VV delay comprises:
adjusting the VV delay in response to the sensed RV activation occurring earlier than the LV activation.

19. The method of claim 18, wherein adjusting the VV delay in response to the sensed RV activation occurring earlier than the sensed LV activation comprises adjusting the VV delay to stimulate the left bundle branch at a time earlier relative to stimulation of the right bundle branch than prior to adjustment.

20. The method of claim 18, further comprising determining whether the adjusted VV delay results in an interval between a subsequent sensed RV activation and a subsequent LV activation meeting a predetermined interval criterion and further adjusting the adjusting the VV delay in response to the adjusted VV delay not resulting in the interval between the subsequent sensed RV activation and the subsequent sensed LV activation not meeting the predetermined interval criterion.

21. The method of claim 20, wherein the interval criterion comprises a predetermined maximum interval duration.

22. The method of claim 20, wherein the interval criterion comprises a predetermined optimal interval duration.

* * * * *